(12) United States Patent
Goldberg

(10) Patent No.: US 11,007,064 B2
(45) Date of Patent: May 18, 2021

(54) ARTHROPLASTY PROSTHESES WITH MULTI-AXIS FIXATION

(71) Applicant: CATALYST ORTHOSCIENCE INC., Naples, FL (US)

(72) Inventor: Steven S. Goldberg, Naples, FL (US)

(73) Assignee: CATALYST ORTHOSCIENCE INC., Naples, FL (US)

( * ) Notice: Subject to any disclaimer, the term of this patent is extended or adjusted under 35 U.S.C. 154(b) by 0 days.

(21) Appl. No.: 16/377,093

(22) Filed: Apr. 5, 2019

(65) Prior Publication Data

US 2019/0231545 A1 Aug. 1, 2019

Related U.S. Application Data

(63) Continuation of application No. 15/653,305, filed on Jul. 18, 2017, now abandoned, which is a (Continued)

(51) Int. Cl.
*A61F 2/40* (2006.01)
*A61F 2/30* (2006.01)

(52) U.S. Cl.
CPC .. *A61F 2/4081* (2013.01); *A61F 2002/30156* (2013.01); *A61F 2002/30878* (2013.01);
(Continued)

(58) Field of Classification Search
CPC ............... A61F 2/4081; A61F 2/4612; A61F 2002/30878; A61F 2002/30889; A61F 2002/30891; A61F 2002/30894; A61F 2/4202; A61F 2002/3412; A61F 2220/0016; A61F 2002/30433; A61F 2002/3863; A61F 2/3872; A61F 2/3868; A61F 2/3877; A61F 2/40; A61F 2002/30881;
(Continued)

(56) References Cited

U.S. PATENT DOCUMENTS 4,106,130 A 8/1978 Scales
4,206,517 A 6/1980 Pappas
(Continued)

FOREIGN PATENT DOCUMENTS

DE 10130796 1/2003
DE 10134511 2/2003
(Continued)

*Primary Examiner* — Alvin J Stewart
(74) *Attorney, Agent, or Firm* — David Meibos; Maywood IP Law

(57) ABSTRACT

Arthroplasty components include an articular surface and a bone-facing surface. In some examples, the bone-facing surface bears at least one anchoring element adapted for an oblique implantation trajectory. The anchoring element includes a reinforcement plate, a dowel, and surface features. Each surface feature resists forces acting along a different direction. In other examples, the bone-facing surface bears anchoring elements that deform along the primary or longest axis of the anchoring element during insertion. In yet other examples, the bone-facing surface is enlarged relative to the articular surface so that at least a portion of the perimeter of the articular surface is circumscribed by the perimeter of the bone-facing surface.

25 Claims, 32 Drawing Sheets

Related U.S. Application Data continuation-in-part of application No. 15/228,443, filed on Aug. 4, 2016, now Pat. No. 9,814,588.

(60) Provisional application No. 62/363,607, filed on Jul. 18, 2016, provisional application No. 62/203,255, filed on Aug. 10, 2015.

(52) U.S. Cl.
CPC .............. *A61F 2002/30881* (2013.01); *A61F 2002/30884* (2013.01); *A61F 2002/30892* (2013.01); *A61F 2002/30902* (2013.01); *A61F 2002/30904* (2013.01); *A61F 2220/0016* (2013.01)

(58) Field of Classification Search
CPC .. A61F 2002/30897; A61F 2002/30902; A61F 2002/30904; A61F 2002/30843; A61F 2002/30841; A61F 2002/30845
See application file for complete search history.

(56) References Cited

U.S. PATENT DOCUMENTS

| | | | |
|---|---|---|---|
| 4,550,450 A | 11/1985 | Kinnett | |
| 4,795,468 A | 1/1989 | Hodorek | |
| 4,865,605 A | 9/1989 | Dines | |
| 4,936,853 A | 6/1990 | Fabian | |
| 4,964,865 A | 10/1990 | Burkhead | |
| 4,986,833 A * | 1/1991 | Worland | A61F 2/40 623/19.11 |
| 5,030,219 A | 7/1991 | Matsen, III | |
| 5,032,132 A | 7/1991 | Matsen, III | |
| 5,383,936 A | 1/1995 | Kubein-Meesenburg | |
| 5,489,309 A | 2/1996 | Lackey | |
| 5,489,310 A | 2/1996 | Mikhail | |
| 5,593,448 A * | 1/1997 | Dong | A61F 2/4081 606/86 R |
| 5,702,447 A | 12/1997 | Walch | |
| 5,723,018 A | 3/1998 | Cyprien | |
| 5,769,856 A | 6/1998 | Dong | |
| 5,800,551 A | 9/1998 | Williamson | |
| 5,814,049 A | 9/1998 | Pratt | |
| 5,851,207 A | 12/1998 | Cesarone | |
| 5,919,195 A | 7/1999 | Wilson | |
| 5,928,285 A | 7/1999 | Bigliani | |
| 5,944,758 A | 8/1999 | Mansat | |
| 5,976,144 A | 11/1999 | Fishbein | |
| 6,045,582 A | 4/2000 | Prybyla | |
| 6,129,732 A | 10/2000 | Lechot | |
| 6,245,074 B1 | 6/2001 | Allard | |
| 6,364,910 B1 | 4/2002 | Shultz | |
| 6,379,386 B1 * | 4/2002 | Resch | A61B 17/1604 623/19.13 |
| 6,406,495 B1 * | 6/2002 | Schoch | A61F 2/4081 623/19.13 |
| 6,475,221 B1 | 11/2002 | White | |
| 6,673,115 B2 | 1/2004 | Resch | |
| 6,679,916 B1 | 1/2004 | Frankle | |
| 6,699,289 B2 * | 3/2004 | Iannotti | A61B 17/1684 623/19.13 |
| 6,783,549 B1 | 8/2004 | Stone | |
| 6,875,234 B2 | 4/2005 | Lipman | |
| 6,911,047 B2 | 6/2005 | Rockwood, Jr. | |
| 7,008,430 B2 | 3/2006 | Dong | |
| 7,048,740 B2 | 5/2006 | White | |
| 7,160,328 B2 | 1/2007 | Rockwood, Jr. | |
| 7,204,854 B2 | 4/2007 | Guederian | |
| 7,217,272 B2 | 5/2007 | Salyer | |
| 7,294,149 B2 * | 11/2007 | Hozack | A61F 2/389 623/20.34 |
| 7,329,284 B2 | 2/2008 | Maroney | |
| 7,588,572 B2 | 9/2009 | White | |
| 7,621,962 B2 | 11/2009 | Lakin | |
| 7,670,382 B2 | 3/2010 | Parrott | |
| 7,780,669 B2 | 8/2010 | Lechot | |
| 7,815,685 B2 | 10/2010 | Farrar | |
| 7,867,234 B2 | 1/2011 | Collazo | |
| 8,007,538 B2 | 8/2011 | Gunther | |
| 8,038,719 B2 | 10/2011 | Gunther | |
| 8,048,161 B2 * | 11/2011 | Guederian | A61F 2/4081 623/17.11 |
| 8,080,063 B2 * | 12/2011 | Ferrand | A61F 2/4081 623/19.13 |
| 8,157,866 B2 | 4/2012 | Winslow | |
| 8,308,809 B2 | 11/2012 | Bishop | |
| 8,425,614 B2 * | 4/2013 | Winslow | A61F 2/4003 623/19.11 |
| 8,444,646 B2 | 5/2013 | Long | |
| 8,465,548 B2 * | 6/2013 | Long | A61F 2/4081 623/19.11 |
| 8,475,460 B1 | 7/2013 | Roger | |
| 8,480,674 B1 | 7/2013 | Roger | |
| 8,540,778 B2 | 9/2013 | Rhodes | |
| 8,556,980 B2 | 10/2013 | Deffenbaugh | |
| 8,591,592 B2 | 11/2013 | Dreyfuss | |
| 8,673,015 B2 | 3/2014 | Maroney | |
| 8,764,836 B2 | 7/2014 | De Wilde | |
| 8,778,028 B2 * | 7/2014 | Gunther | A61B 17/1659 623/19.11 |
| 8,870,962 B2 | 10/2014 | Roche | |
| 8,876,907 B2 * | 11/2014 | Baptista | A61F 2/4081 623/19.11 |
| 8,974,537 B2 | 3/2015 | Dreyfuss | |
| 8,986,309 B1 | 3/2015 | Murphy | |
| D730,522 S * | 5/2015 | Goldberg | A61B 17/1684 D24/155 |
| 9,119,643 B2 | 9/2015 | Winslow | |
| 9,132,016 B2 * | 9/2015 | Flaherty | A61F 2/30749 |
| 9,180,016 B2 | 11/2015 | Maroney | |
| 9,233,003 B2 | 1/2016 | Roche | |
| 9,237,894 B2 | 1/2016 | Hernandez | |
| 9,283,076 B2 | 3/2016 | Sikora | |
| 9,289,306 B2 * | 3/2016 | Goldberg | A61F 2/4003 |
| 9,345,578 B2 | 5/2016 | Collazo | A61B 17/157 |
| 9,351,844 B2 * | 5/2016 | Walch | A61F 2/4081 |
| D759,819 S * | 6/2016 | Goldberg | A61B 17/1778 D24/155 |
| 9,370,428 B2 | 6/2016 | Winslow | |
| 9,381,085 B2 * | 7/2016 | Axelson, Jr. | A61F 2/389 |
| 9,433,507 B2 | 9/2016 | Reubelt | |
| 9,474,619 B2 * | 10/2016 | Reubelt | A61F 2/4081 |
| 9,610,166 B2 | 4/2017 | Gunther | |
| 9,775,716 B2 | 10/2017 | Goldberg | |
| 9,814,471 B2 | 11/2017 | Goldberg | |
| 9,814,588 B2 * | 11/2017 | Goldberg | A61F 2/4081 |
| D810,940 S | 2/2018 | Goldberg | |
| D835,276 S * | 12/2018 | Humphrey | A61F 2/4081 D24/155 |
| 10,524,922 B2 * | 1/2020 | Courtney, Jr. | A61F 2/4081 |
| 2002/0077702 A1 * | 6/2002 | Castro | A61F 2/442 623/17.16 |
| 2003/0134252 A1 | 7/2003 | Sussman | |
| 2003/0187449 A1 | 10/2003 | McCleary | |
| 2003/0204263 A1 | 10/2003 | Justin | |
| 2004/0117027 A1 * | 6/2004 | Reiley | A61B 17/1682 623/21.18 |
| 2005/0015093 A1 | 1/2005 | Suh | |
| 2005/0038444 A1 | 2/2005 | Binder | |
| 2005/0049709 A1 | 3/2005 | Tornier | |
| 2005/0060039 A1 * | 3/2005 | Cyprien | A61B 17/1684 623/19.13 |
| 2005/0222572 A1 | 10/2005 | Chana | |
| 2005/0261775 A1 | 11/2005 | Baum | |
| 2006/0030946 A1 | 2/2006 | Ball | |
| 2006/0069443 A1 | 3/2006 | Deffenbaugh | |
| 2006/0074430 A1 | 4/2006 | Deffenbaugh | |
| 2006/0094958 A1 | 5/2006 | Marquart | |
| 2006/0100637 A1 | 5/2006 | Rathbun | |
| 2006/0111787 A1 * | 5/2006 | Bailie | A61F 2/4081 623/19.13 |

(56) References Cited

U.S. PATENT DOCUMENTS

| | | | |
|---|---|---|---|
| 2007/0055380 A1* | 3/2007 | Berelsman | A61F 2/4081 623/19.11 |
| 2007/0100461 A1 | 5/2007 | Incavo | |
| 2007/0142917 A1 | 6/2007 | Roche | |
| 2007/0219637 A1 | 9/2007 | Berelsman | |
| 2007/0219638 A1* | 9/2007 | Jones | A61F 2/4081 623/19.11 |
| 2007/0244564 A1* | 10/2007 | Ferrand | A61F 2/4081 623/19.13 |
| 2008/0058948 A1* | 3/2008 | Biegun | A61F 2/3859 623/20.35 |
| 2008/0109000 A1 | 5/2008 | Maroney | |
| 2008/0147070 A1 | 6/2008 | Michel | |
| 2008/0188855 A1* | 8/2008 | Brown | A61F 2/3877 606/88 |
| 2008/0287952 A1 | 11/2008 | Mcminn | |
| 2008/0294266 A1 | 11/2008 | Steinberg | |
| 2009/0005798 A1 | 1/2009 | Brunner | |
| 2009/0018664 A1 | 1/2009 | Kropf | |
| 2009/0125113 A1* | 5/2009 | Guederian | A61F 2/4081 623/19.11 |
| 2009/0138016 A1 | 5/2009 | Berthusen | |
| 2009/0192621 A1 | 7/2009 | Winslow | |
| 2009/0226068 A1 | 9/2009 | Fitz | |
| 2009/0228114 A1* | 9/2009 | Clark | A61F 2/389 623/20.36 |
| 2009/0240333 A1* | 9/2009 | Trudeau | A61F 2/4684 623/17.13 |
| 2009/0312839 A1 | 12/2009 | Scheker | |
| 2010/0009964 A1 | 1/2010 | Berry et al. | |
| 2010/0049327 A1 | 2/2010 | Isch | |
| 2010/0087876 A1 | 4/2010 | Gunther | |
| 2010/0087877 A1 | 4/2010 | Gunther | |
| 2010/0094429 A1* | 4/2010 | Otto | A61F 2/3877 623/20.14 |
| 2010/0161065 A1 | 6/2010 | Williams, Jr. | |
| 2010/0228352 A1 | 9/2010 | Courtney, Jr. | |
| 2010/0241235 A1* | 9/2010 | Basamania | A61F 2/4612 623/19.11 |
| 2010/0268239 A1 | 10/2010 | Sikora | |
| 2011/0106266 A1 | 5/2011 | Schwyzer | |
| 2011/0144760 A1* | 6/2011 | Wong | A61F 2/38 623/20.14 |
| 2011/0190898 A1* | 8/2011 | Lenz | A61F 2/38 623/20.32 |
| 2011/0230972 A1 | 9/2011 | Katrana | |
| 2011/0276144 A1 | 11/2011 | Wirth | |
| 2012/0130500 A1 | 5/2012 | Maroney | |
| 2012/0179147 A1 | 7/2012 | Geebelen | |
| 2012/0191204 A1* | 7/2012 | Bae | A61F 2/389 623/20.31 |
| 2012/0209392 A1 | 8/2012 | Angibaud | |
| 2012/0221112 A1* | 8/2012 | Lappin | A61F 2/4603 623/19.11 |
| 2012/0239156 A1 | 9/2012 | De Wilde | |
| 2012/0310360 A1 | 12/2012 | Parrott | |
| 2012/0330429 A1* | 12/2012 | Axelson, Jr. | A61F 2/30771 623/20.19 |
| 2013/0024000 A1 | 1/2013 | Bojarski | |
| 2013/0090737 A1 | 4/2013 | Flaherty | |
| 2013/0144393 A1 | 6/2013 | Mutchler | |
| 2013/0145609 A1 | 6/2013 | Sperling | |
| 2013/0166033 A1 | 6/2013 | Gunther | |
| 2013/0190827 A1* | 7/2013 | Butters | A61B 17/8061 606/286 |
| 2013/0204254 A1 | 8/2013 | Slone | |
| 2013/0309030 A1 | 11/2013 | Winslow | |
| 2014/0128983 A1* | 5/2014 | Flaherty | A61B 17/842 623/19.13 |
| 2014/0163565 A1 | 6/2014 | Bollinger | |
| 2014/0228860 A1 | 8/2014 | Steines | |
| 2014/0257495 A1* | 9/2014 | Goldberg | A61F 2/4657 623/19.11 |
| 2015/0320567 A1 | 11/2015 | Terrill | |
| 2015/0335440 A1 | 11/2015 | Linares | |
| 2016/0051367 A1 | 2/2016 | Gervasi | |
| 2016/0089164 A1 | 3/2016 | Winslow | |
| 2016/0095607 A1 | 4/2016 | Hernandez | |
| 2016/0143637 A1* | 5/2016 | Nering | A61B 17/068 606/151 |
| 2016/0242921 A1* | 8/2016 | Walch | A61F 2/4081 |
| 2016/0287266 A1 | 10/2016 | Sikora | |
| 2017/0014238 A1 | 1/2017 | Reubelt | |
| 2017/0042689 A1 | 2/2017 | Goldberg | |
| 2017/0151061 A1* | 6/2017 | Lavi | A61F 2/4225 |
| 2017/0231642 A1 | 8/2017 | Chaney | |
| 2017/0239058 A1 | 8/2017 | Goldberg | |
| 2017/0273795 A1 | 9/2017 | Neichel | |
| 2017/0319348 A1 | 11/2017 | Goldberg | |
| 2017/0348112 A1 | 12/2017 | Goldberg | |
| 2018/0028323 A1* | 2/2018 | Servidio | A61F 2/389 |
| 2018/0200068 A1 | 7/2018 | Goldberg | |
| 2018/0303619 A1* | 10/2018 | Kehres | A61F 2/30 |
| 2019/0350717 A1* | 11/2019 | Tuttle | A61F 2/30767 |
| 2020/0038194 A1* | 2/2020 | Kester | A61F 2/3877 |

FOREIGN PATENT DOCUMENTS

| | | |
|---|---|---|
| EP | 1159939 | 7/2005 |
| EP | 2446859 | 5/2012 |
| FR | 2825263 | 12/2002 |
| FR | 2836821 | 5/2004 |
| GB | 2308068 | 9/1999 |
| IN | 201508960 | 7/2016 |
| WO | WO2002017822 | 3/2002 |

* cited by examiner

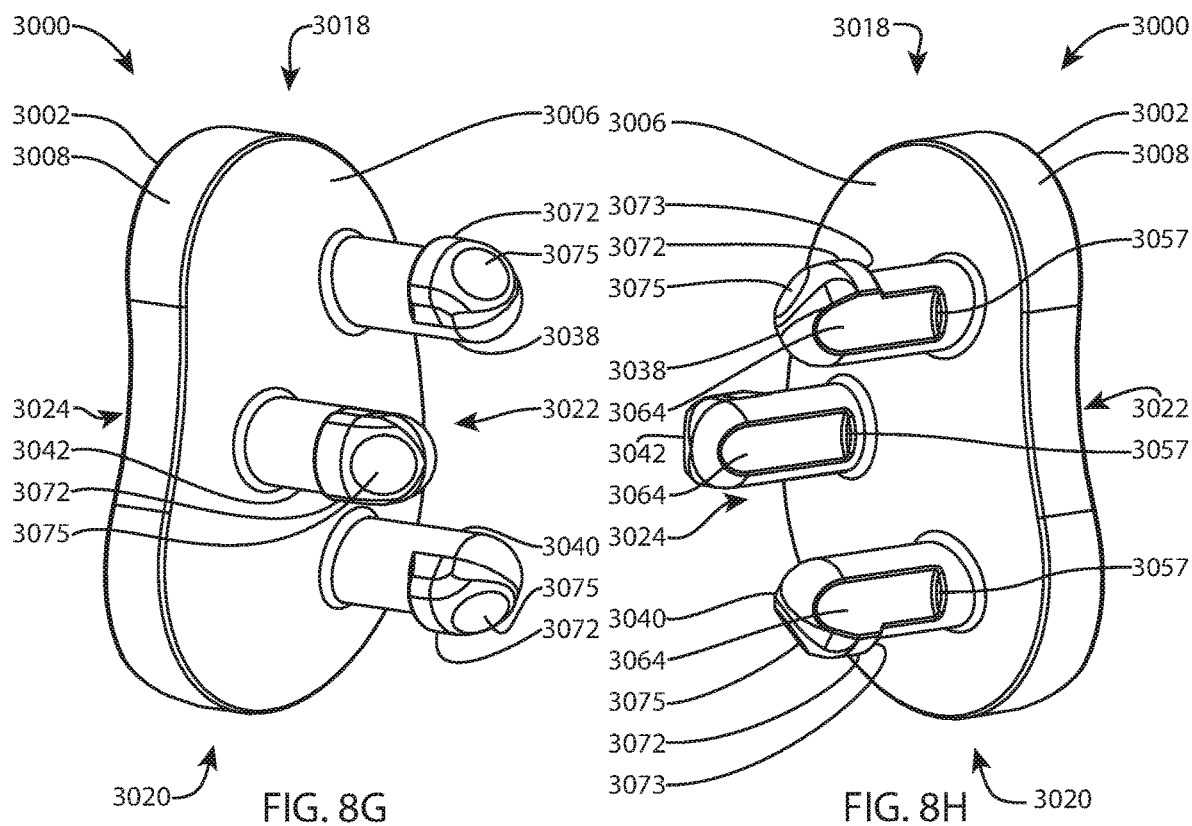
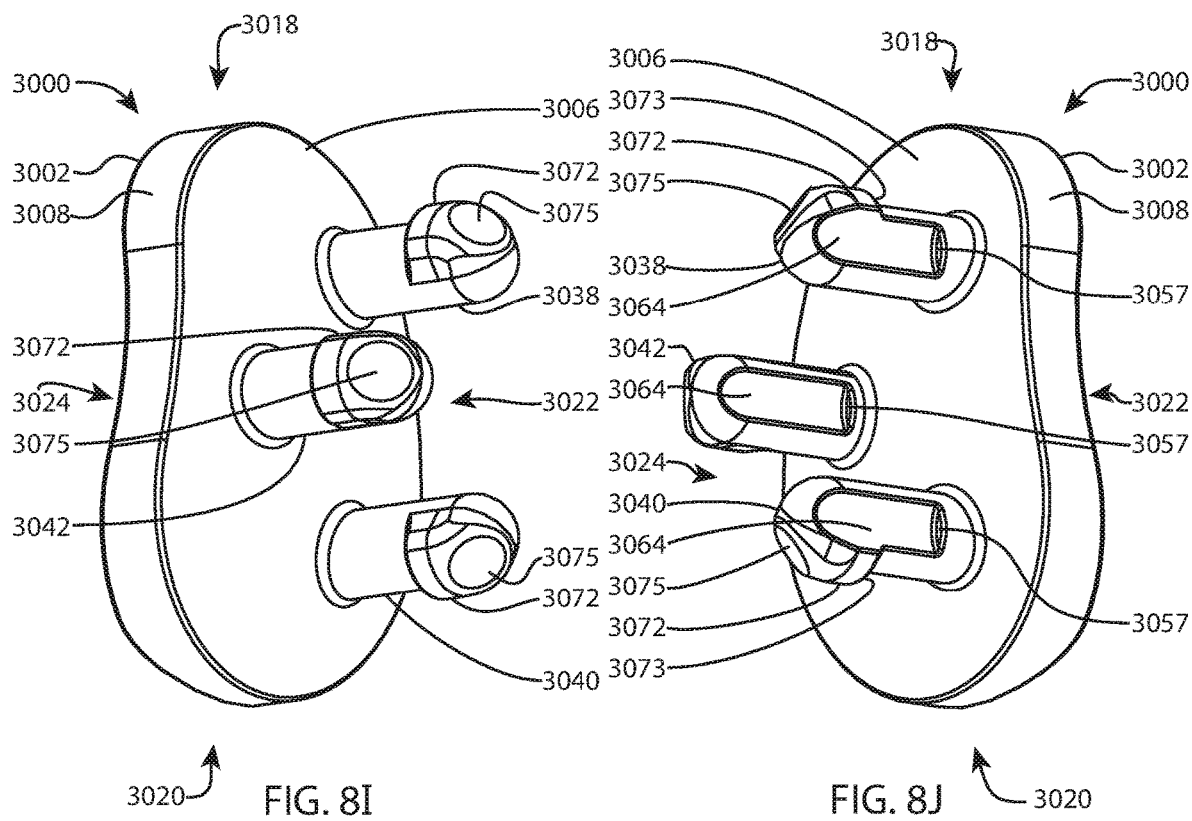

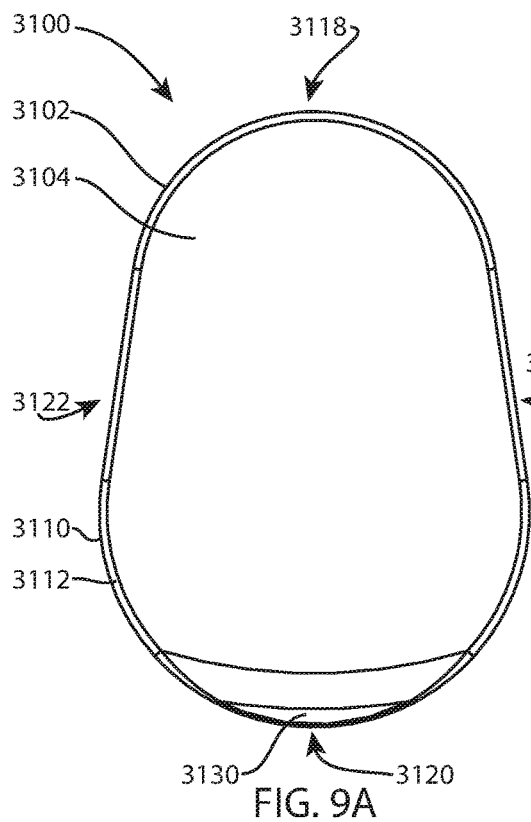
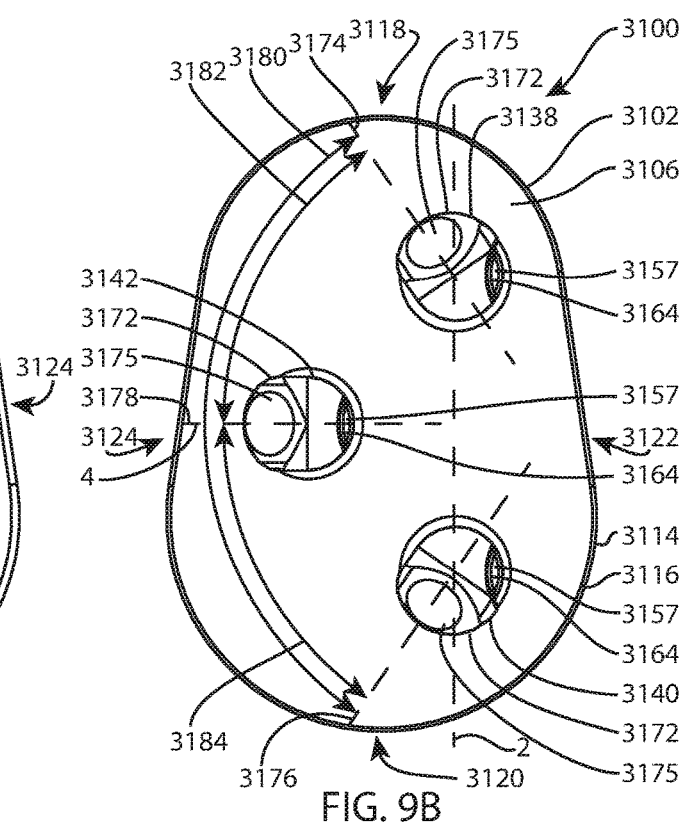
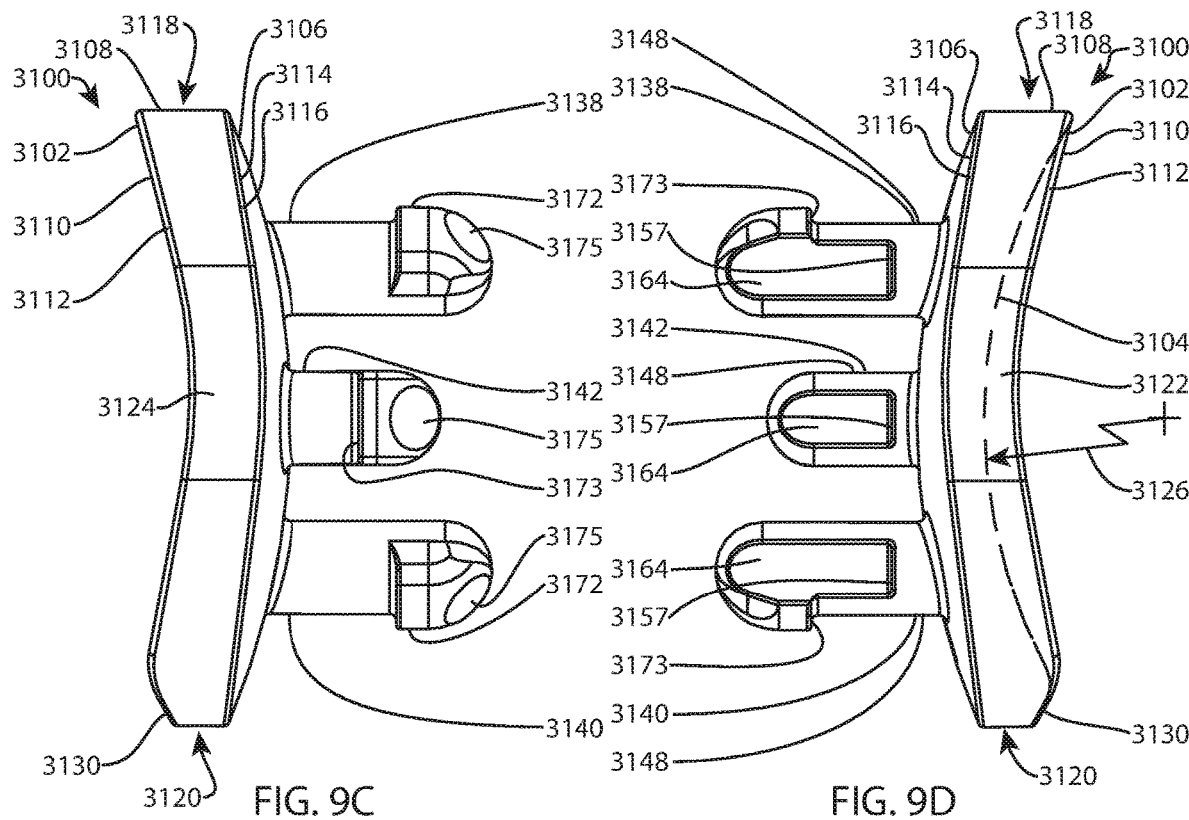

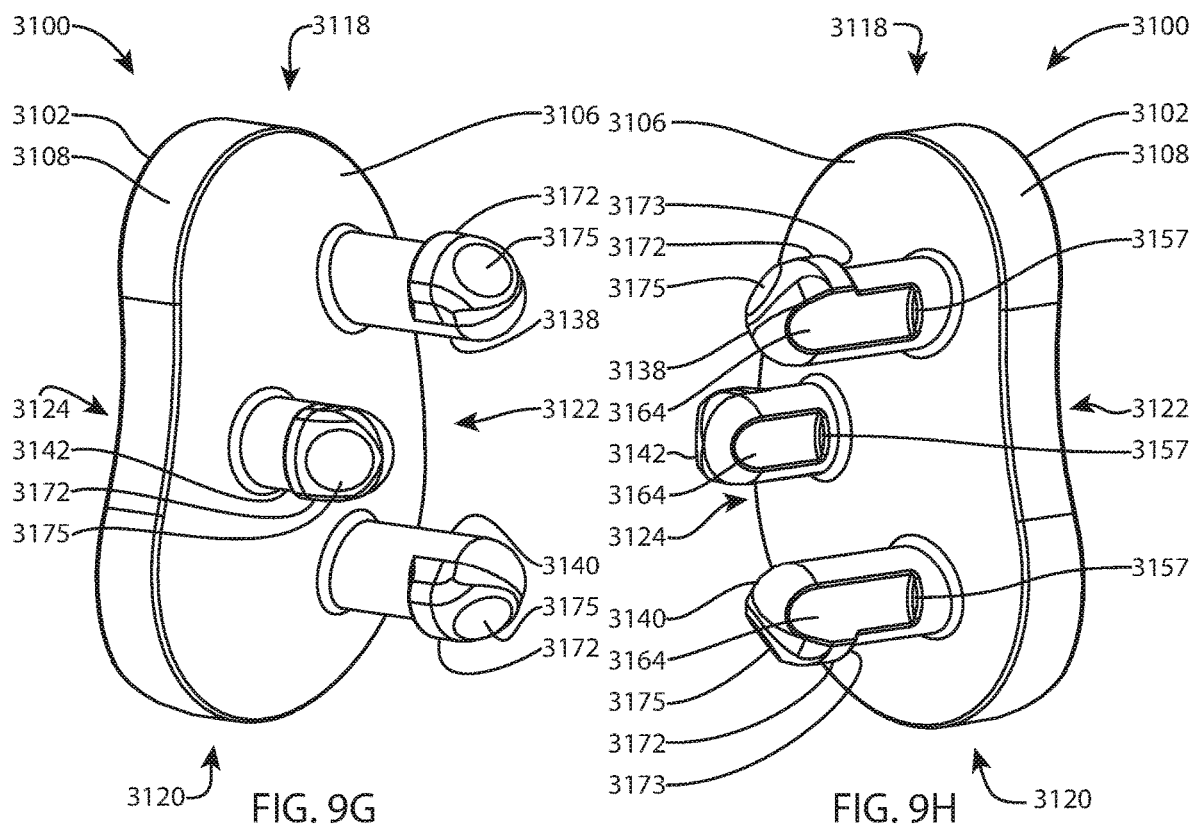
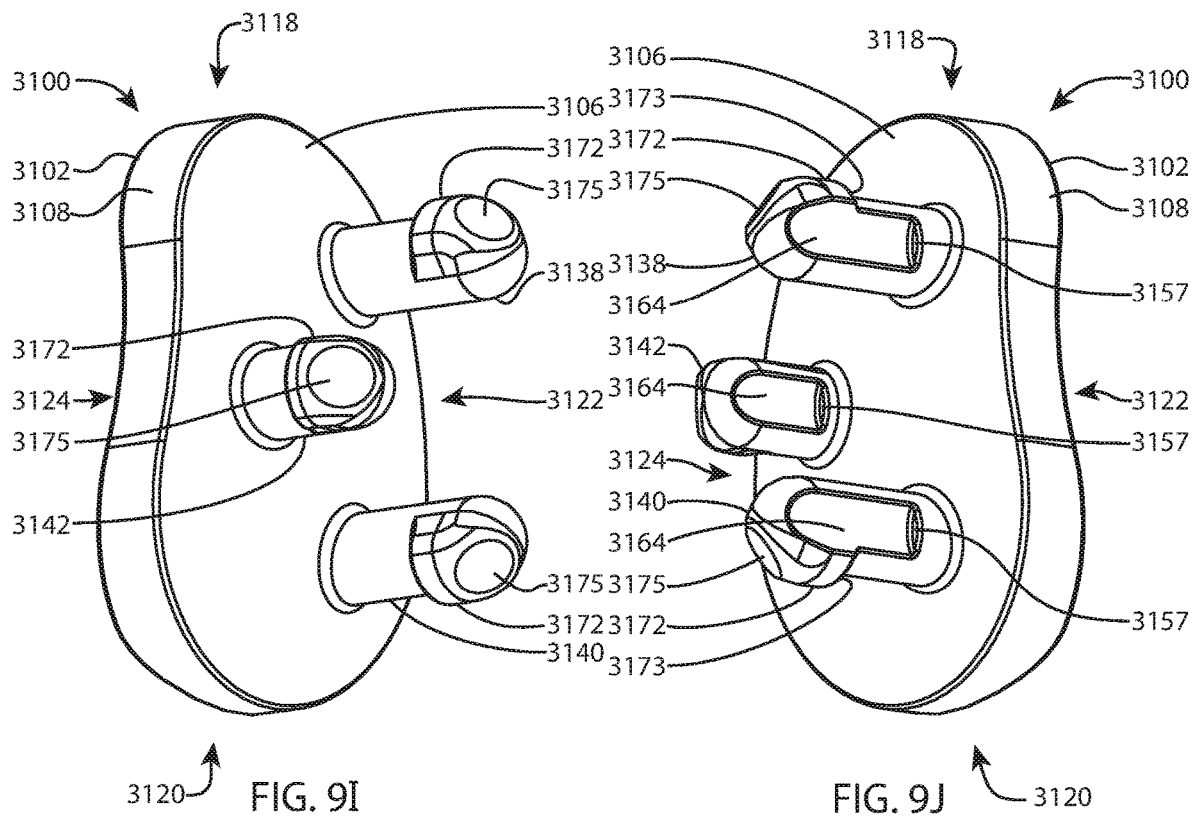

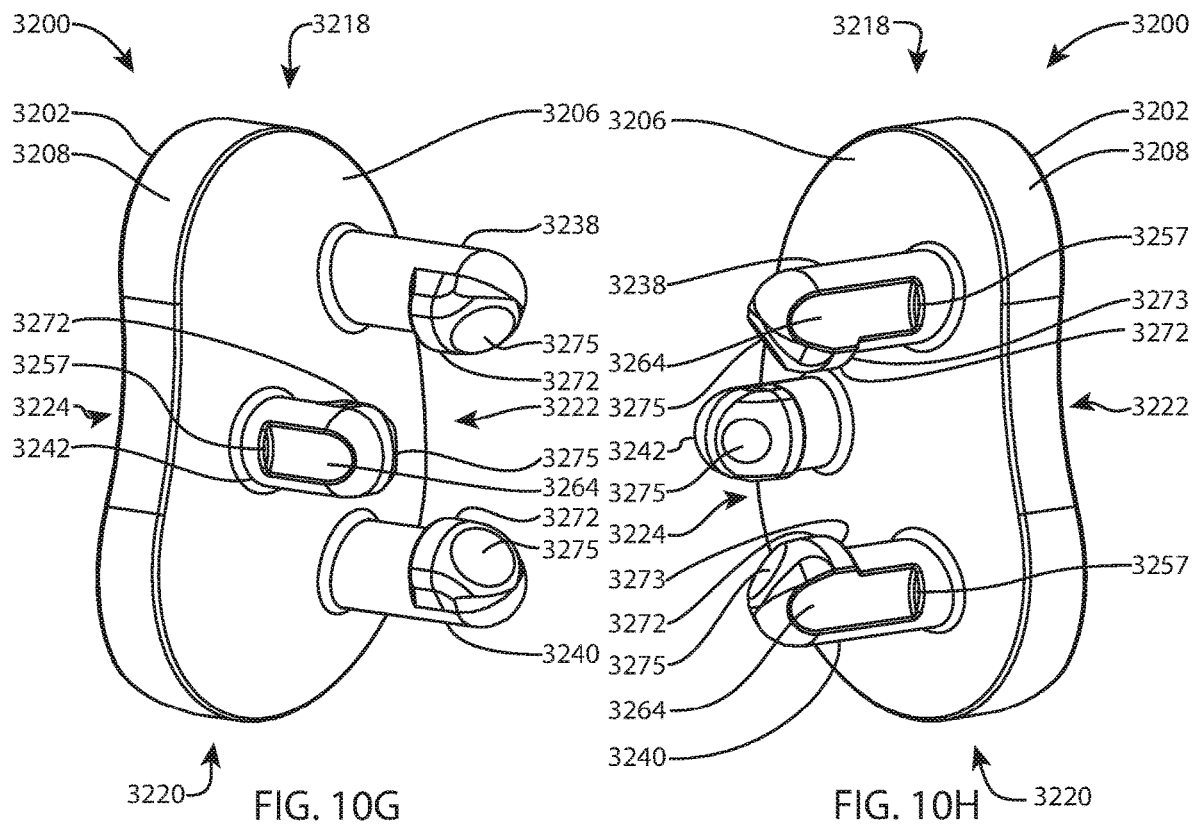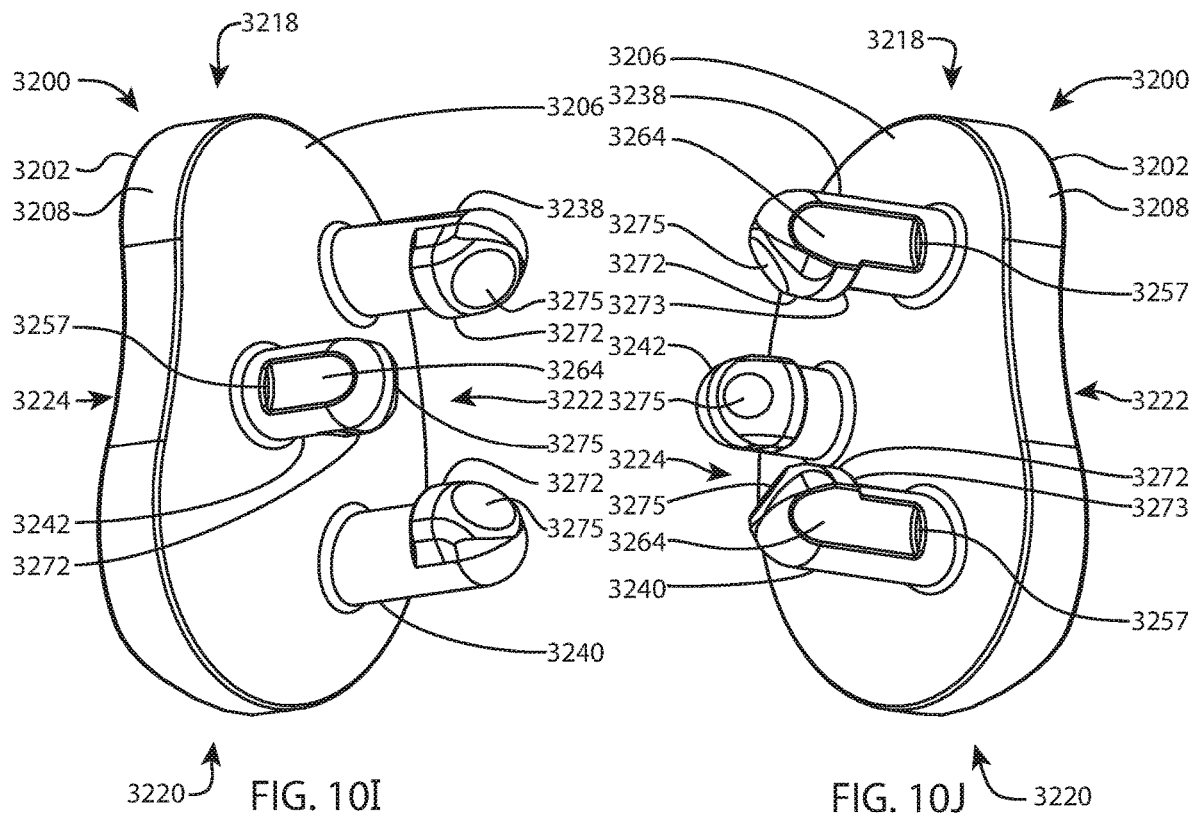

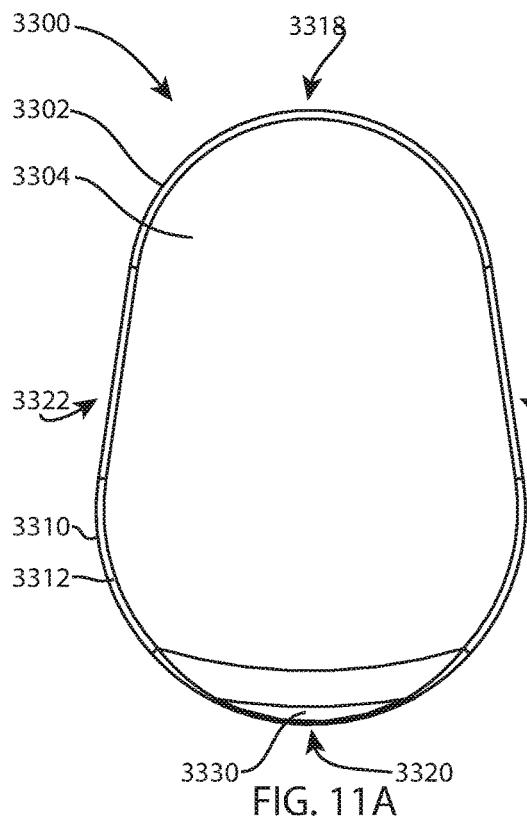
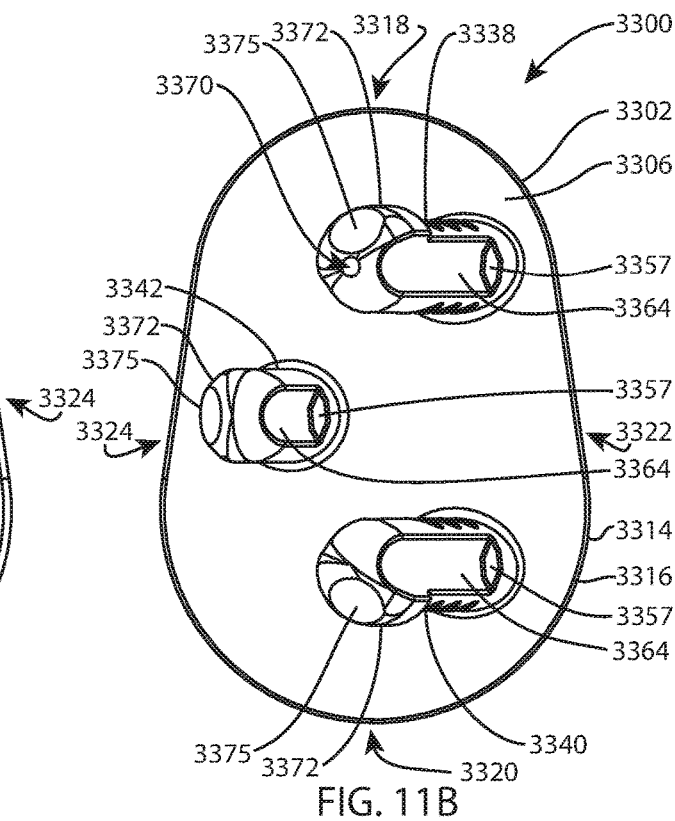
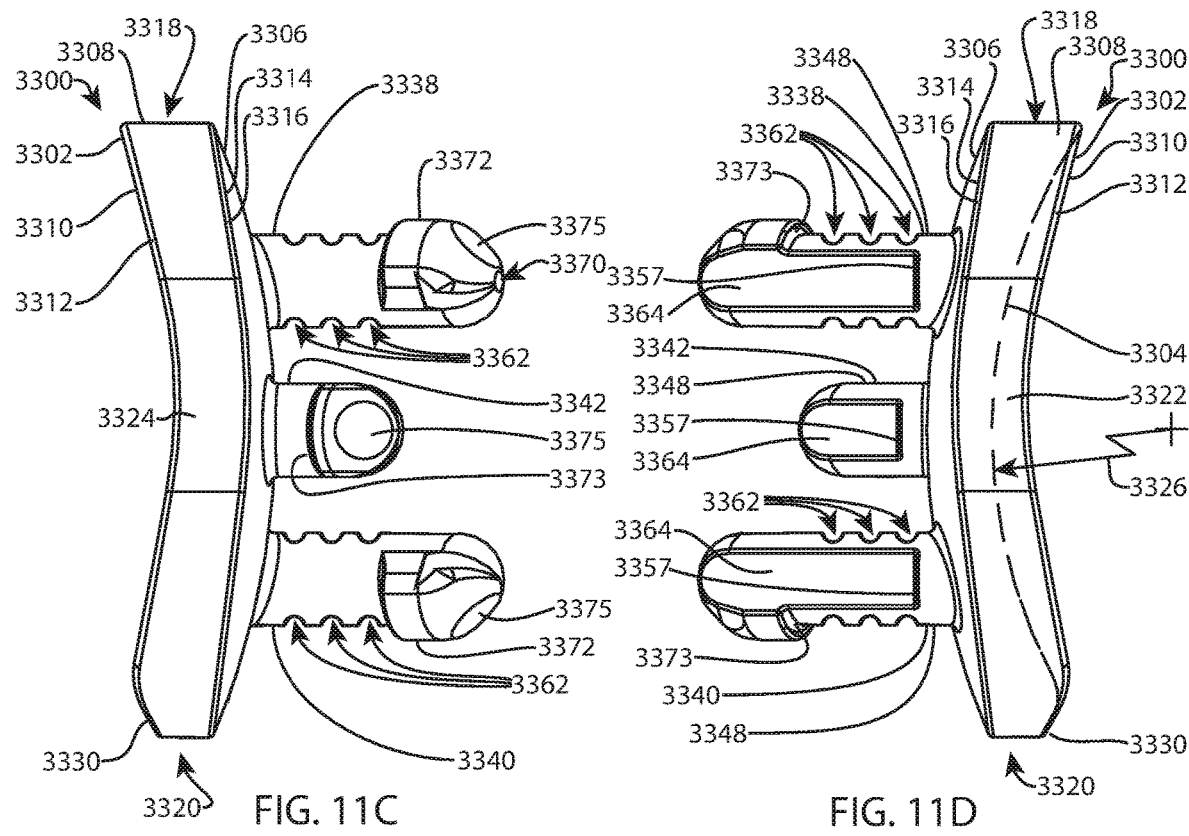
FIG. 11A    FIG. 11B    FIG. 11C    FIG. 11D

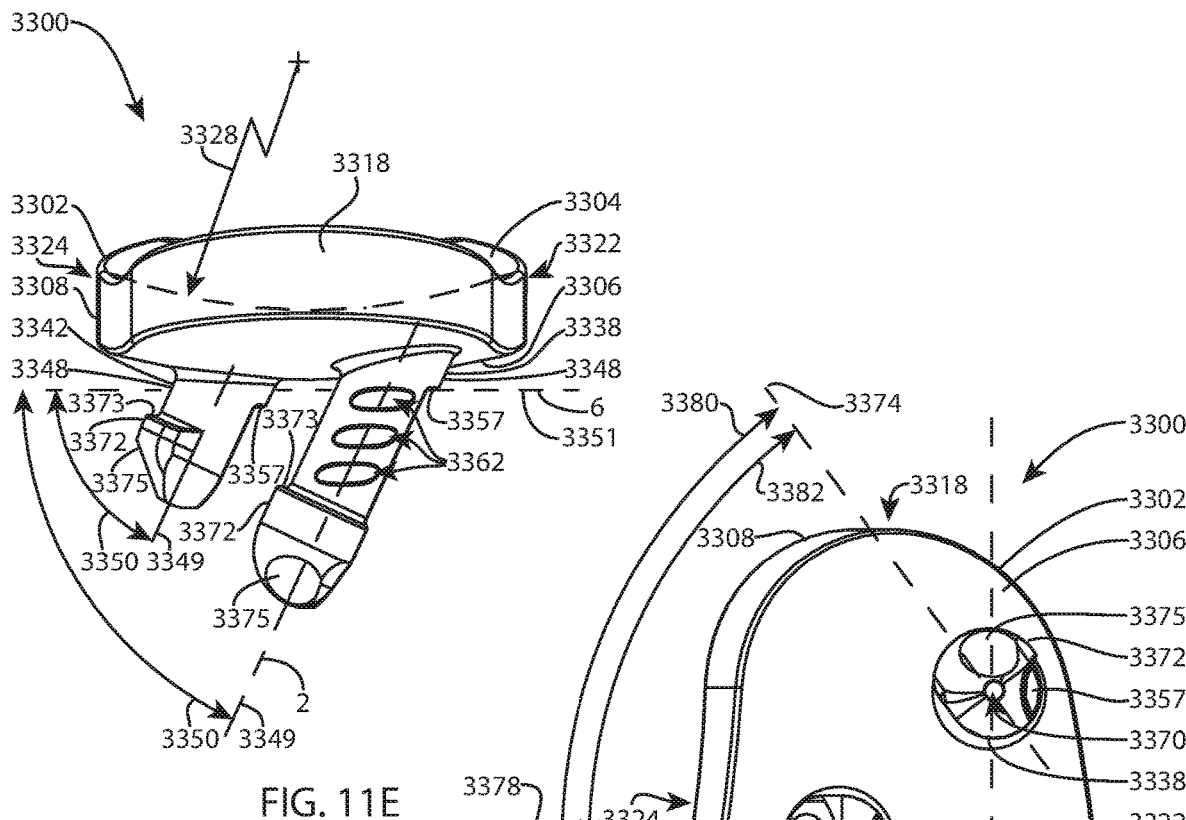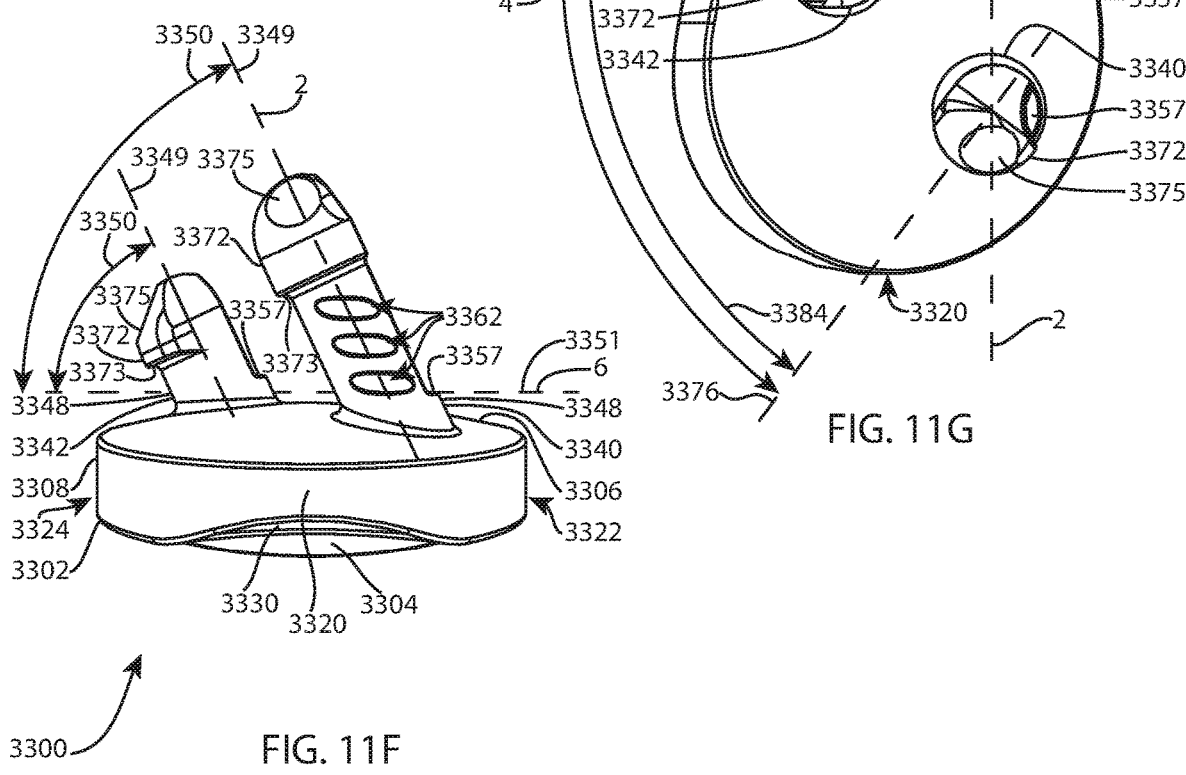
FIG. 11E
FIG. 11F
FIG. 11G

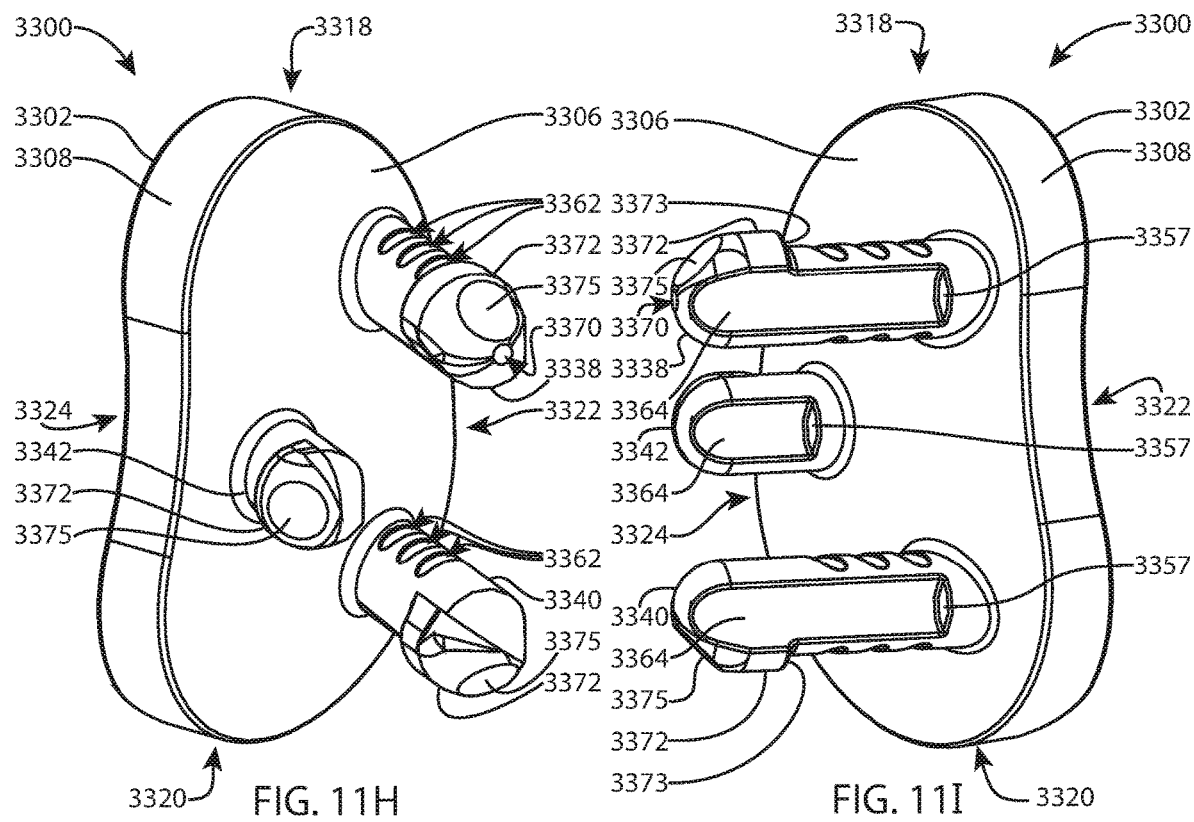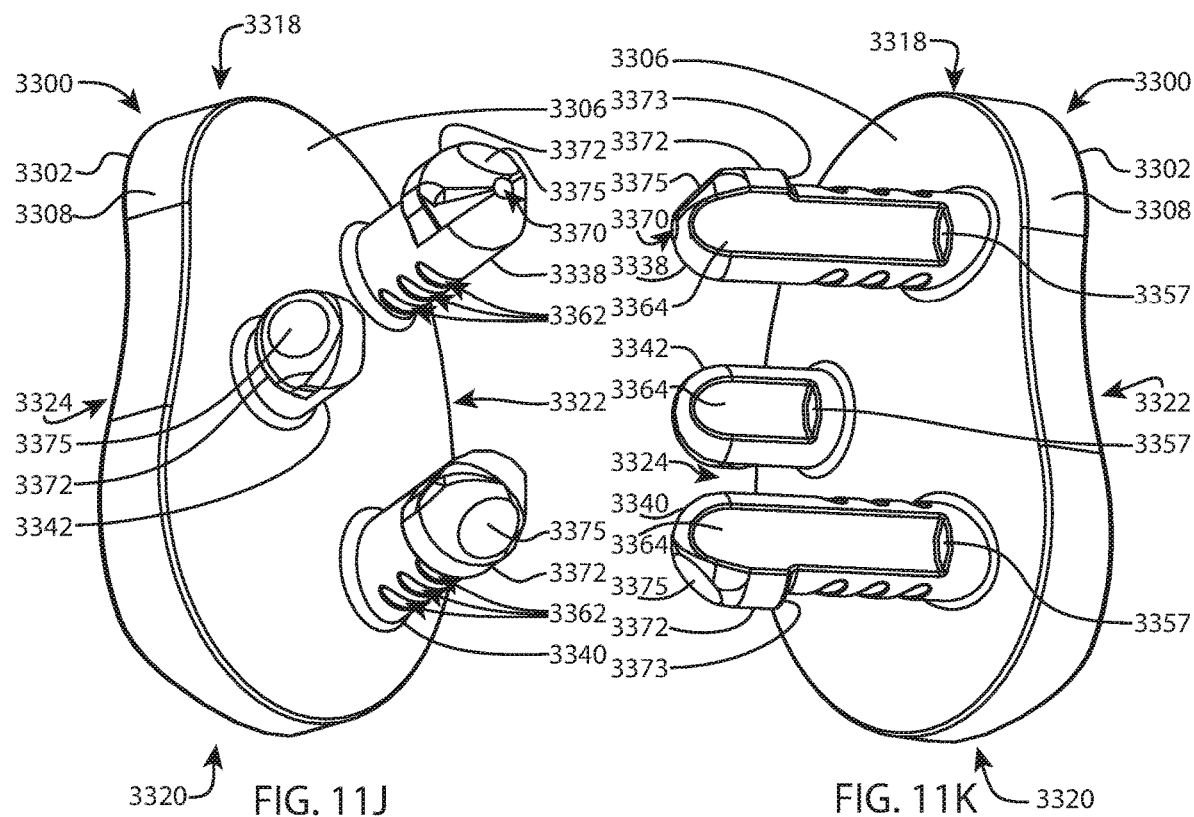

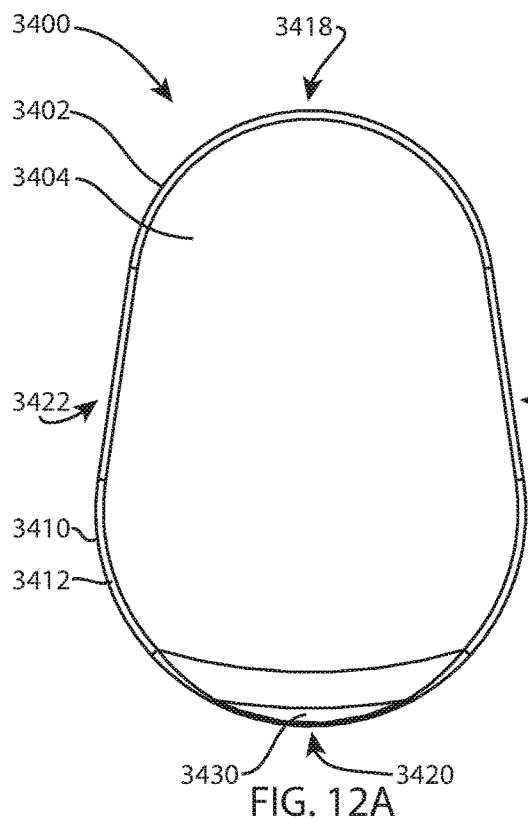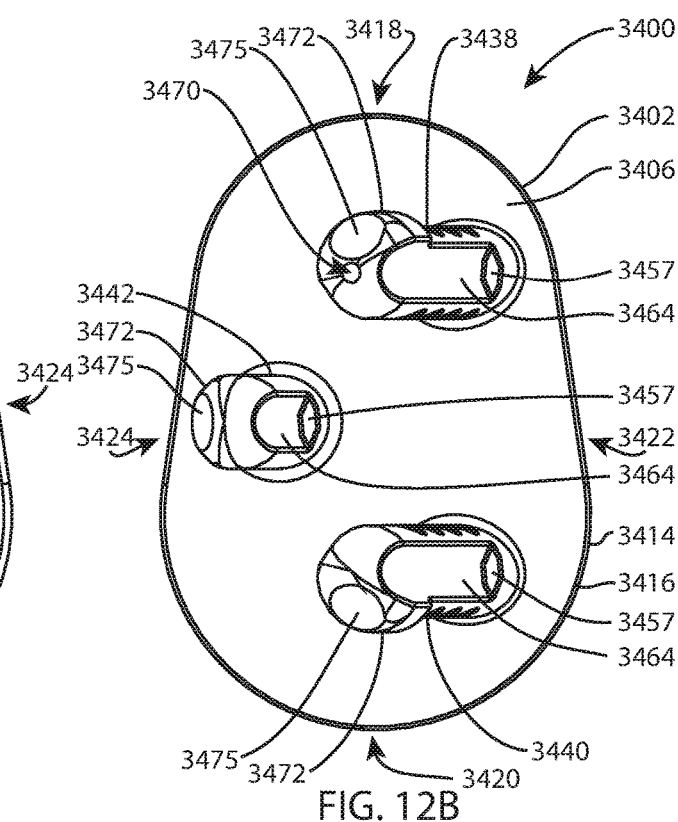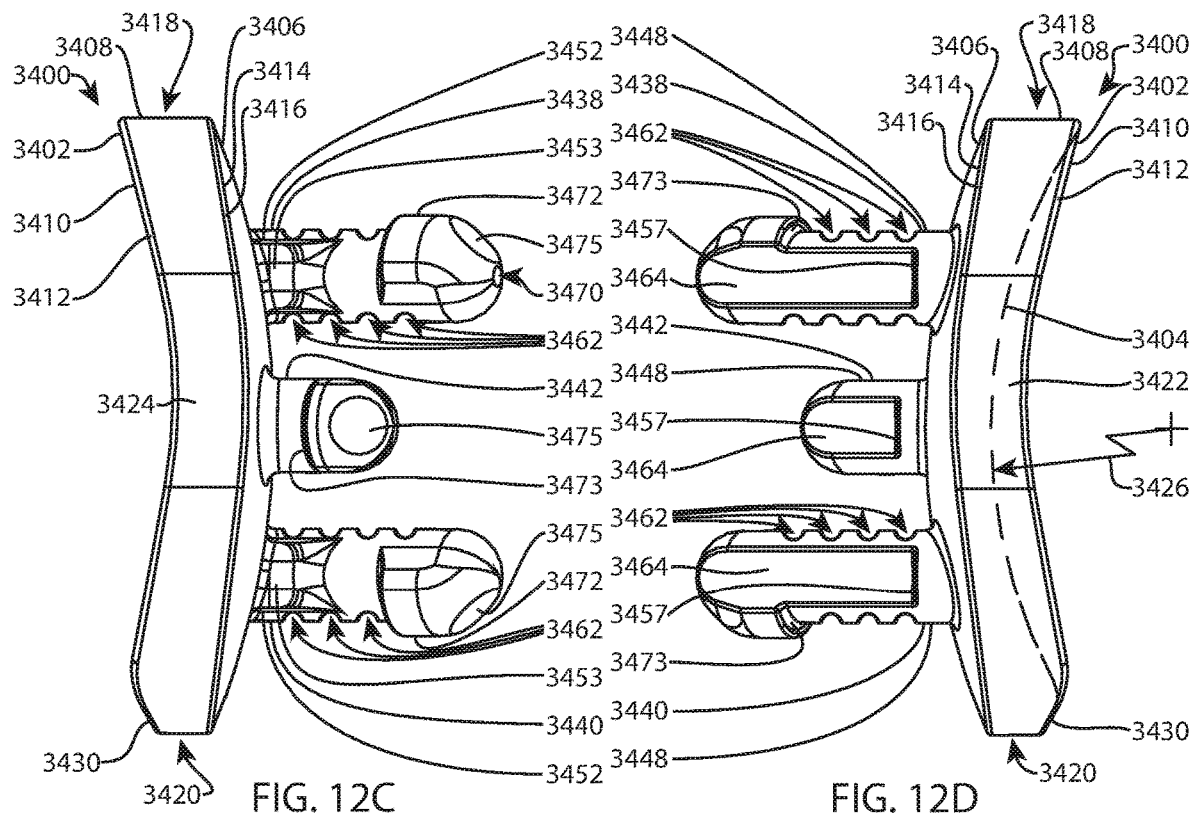

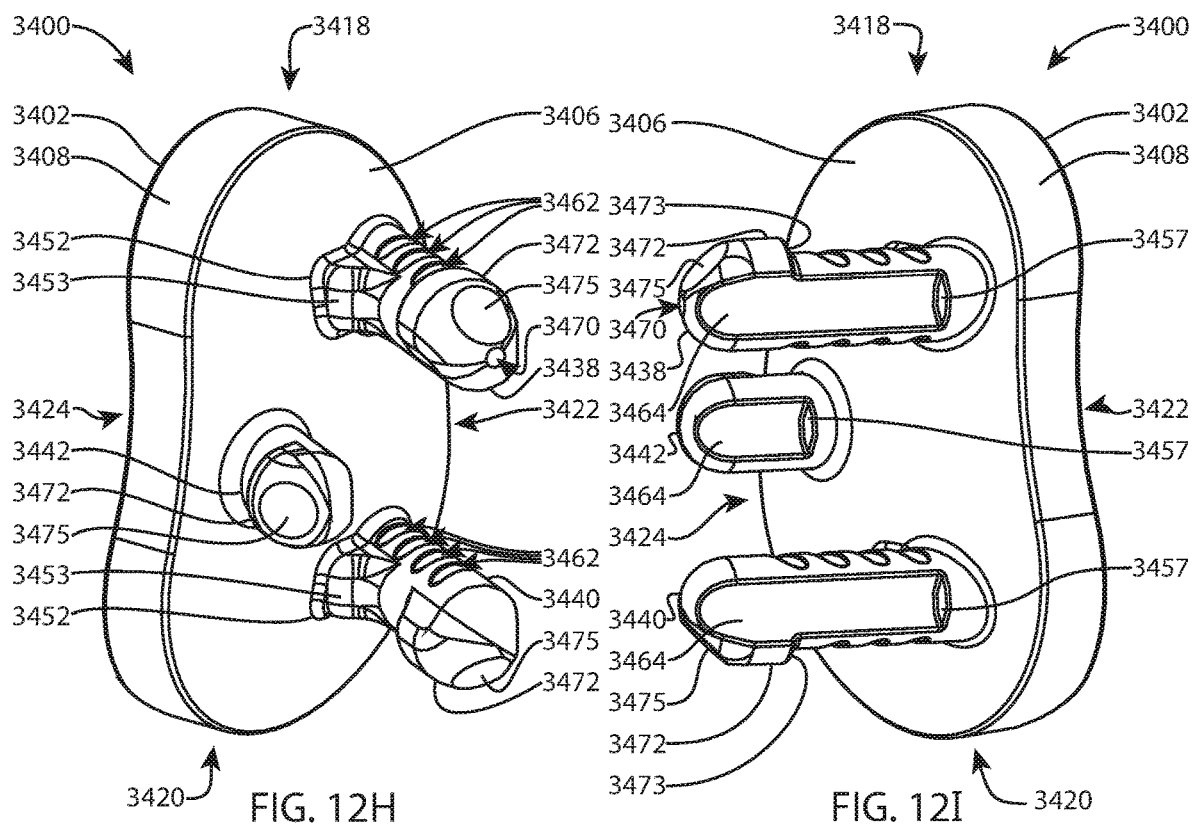
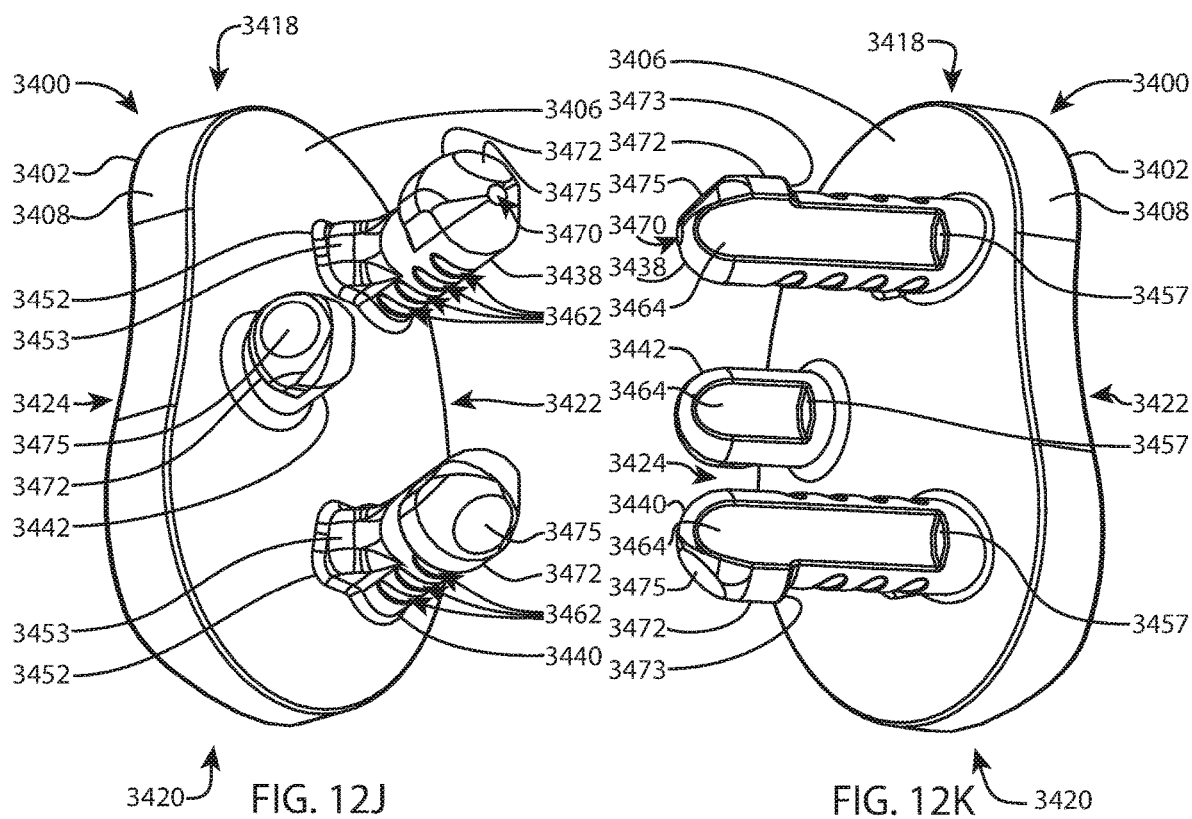

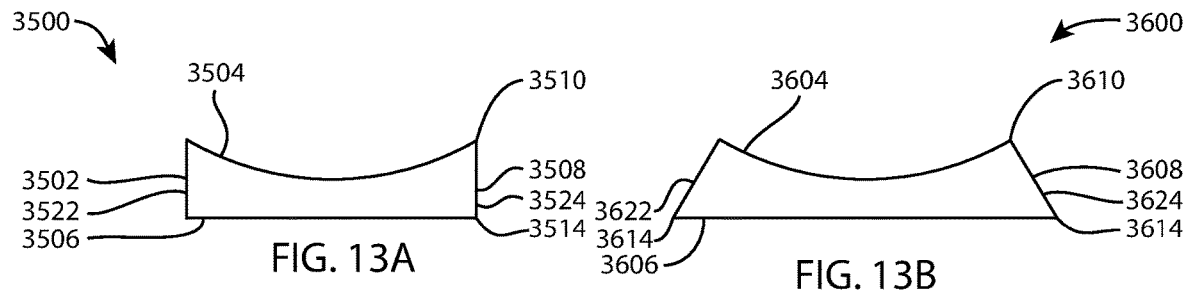
FIG. 13A
FIG. 13B
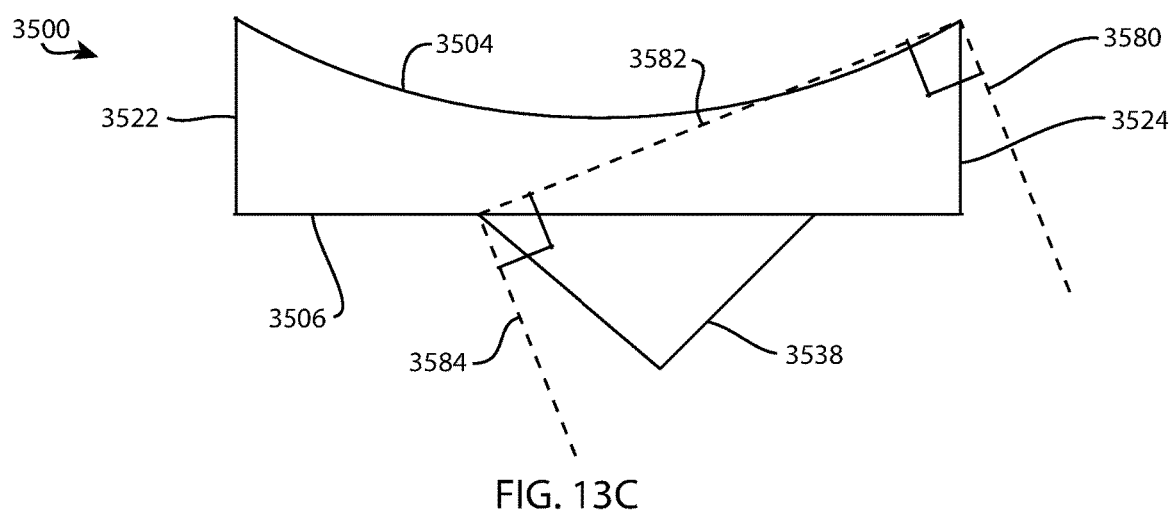
FIG. 13C
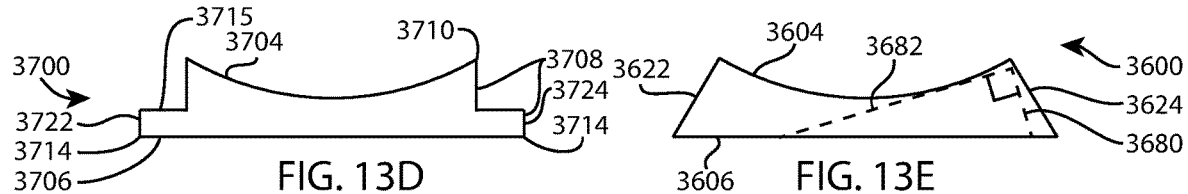
FIG. 13D
FIG. 13E
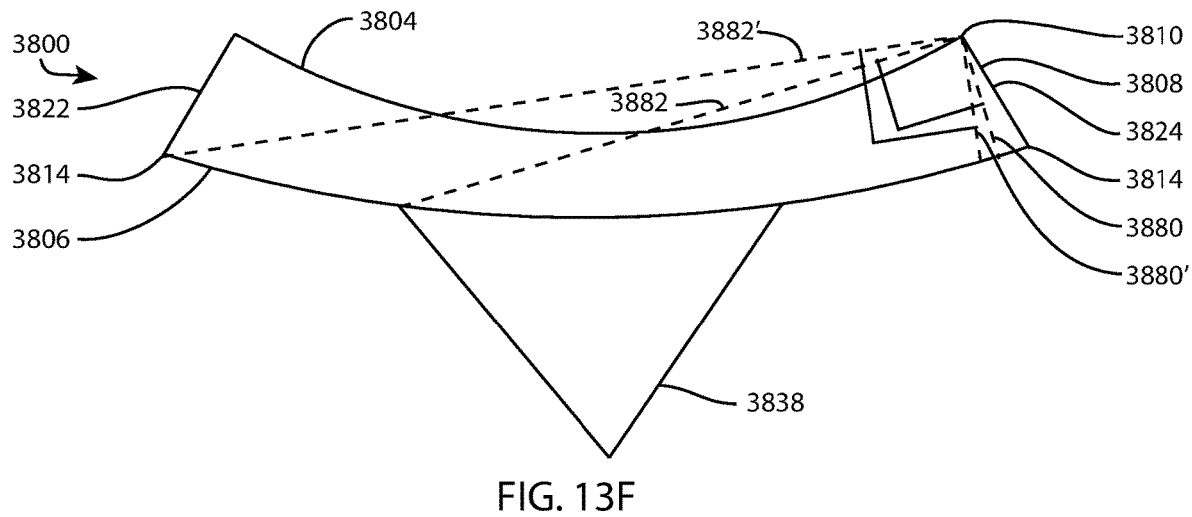
FIG. 13F

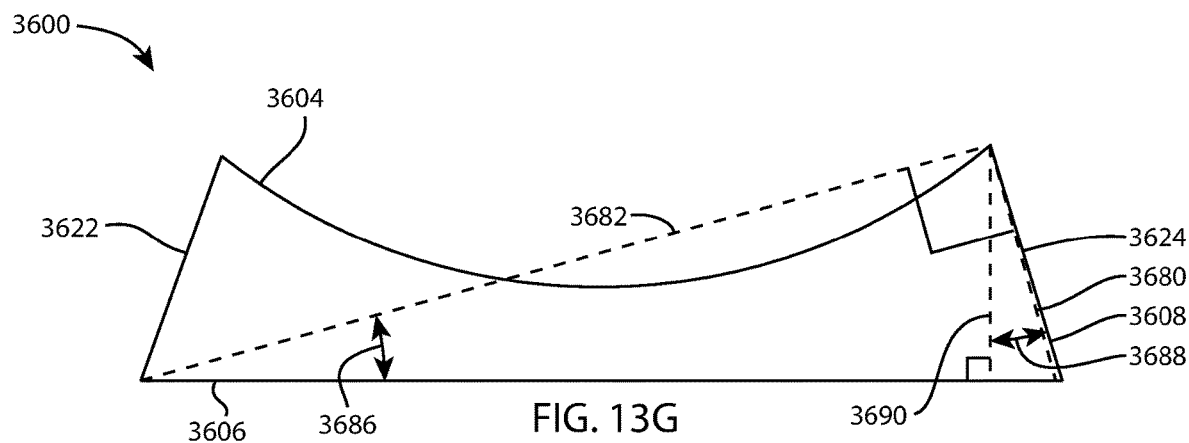
FIG. 13G
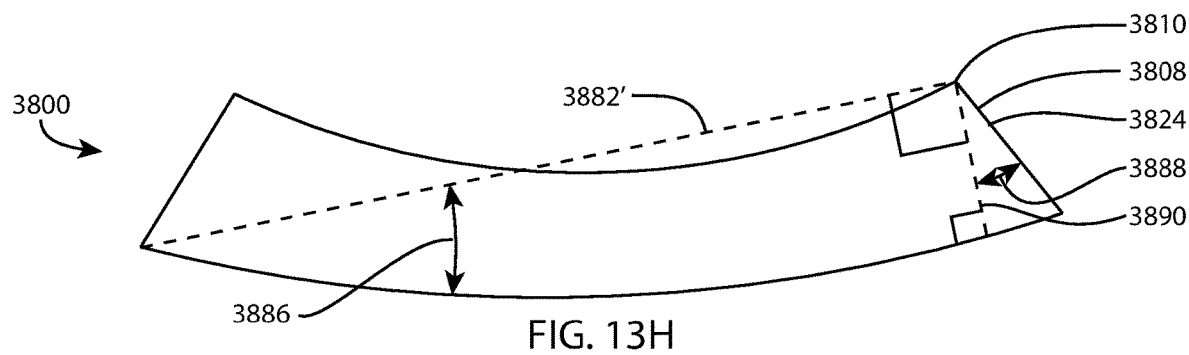
FIG. 13H
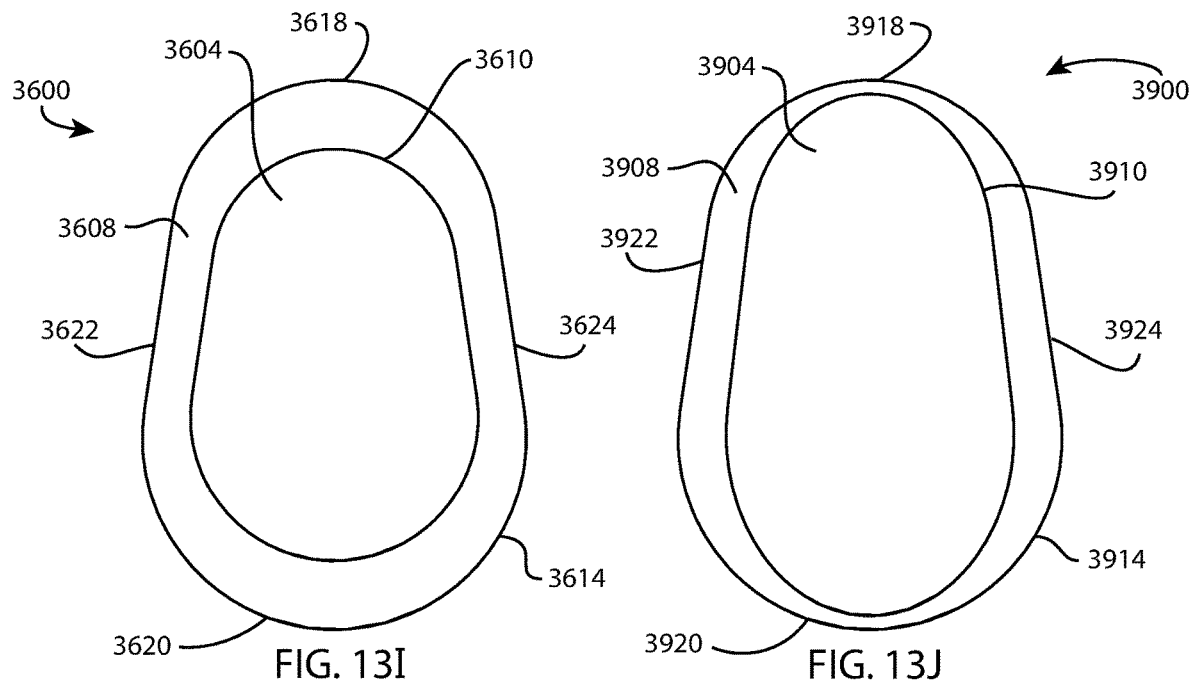
FIG. 13I
FIG. 13J

ARTHROPLASTY PROSTHESES WITH MULTI-AXIS FIXATION

RELATED APPLICATIONS

The present application is a continuation of:

U.S. patent application Ser. No. 15/653,305, filed Jul. 18, 2017, entitled ARTHROPLASTY PROSTHESES WITH MULTI-AXIS FIXATION, which is pending.

U.S. patent application Ser. No. 15/653,305 claims the benefit of:

U.S. Provisional Patent Application No. 62/363,607, filed Jul. 18, 2016, entitled ARTHROPLASTY PROSTHESES WITH MULTI-AXIS FIXATION, which is expired.

U.S. patent application Ser. No. 15/653,305 is a continuation-in-part of:

U.S. patent application Ser. No. 15/228,443, filed Aug. 4, 2016, entitled GLENOID ARTHROPLASTY WITH MULTI-DIRECTIONAL FIXATION, which issued on Nov. 14, 2017 as U.S. Pat. No. 9,814,588.

U.S. patent application Ser. No. 15/228,443 claims the benefit of:

U.S. Provisional Patent Application No. 62/203,255, filed Aug. 10, 2015, entitled GLENOID ARTHROPLASTY WITH MULTI-DIRECTIONAL FIXATION, which is expired.

The foregoing are incorporated by reference as though set forth herein in their entirety.

TECHNICAL FIELD

The present disclosure relates to anchoring elements and articular surfaces for human or veterinary arthroplasty implants. The anchoring elements in this disclosure incorporate multi-directional fixation, also referred to as multi-directional resistance to pull-out or multi-axis fixation. The disclosed anchoring elements are useful in situations where exposure is difficult, the implantation trajectory is oblique to the implantation site, or the implantation site is tapered, conical, or wedge-shaped. For example, the disclosed anchoring elements are useful in the context of a glenoid component for shoulder arthroplasty, so that the preparation of the glenoid and implantation of the glenoid component take place along an oblique surgical access and implantation trajectory. An oblique approach, or an antero-lateral approach, to the glenoid is technically simpler and less invasive than a lateral trajectory to the glenoid. This disclosure is made in the context of glenoid components for shoulder arthroplasty for the purpose of illustrating the relevant principles of the technology. However, the principles disclosed herein are applicable to arthroplasty components for other joints in human or animal skeletons, wherever an oblique implantation trajectory would simplify and reduce the invasiveness of the surgical technique or whenever multi-directional or multi-axis fixation is desired.

In total shoulder arthroplasty, a glenoid implant is attached to a prepared glenoid or scapula, and a humeral implant is attached to a prepared humerus. The humeral implant usually includes a ball or convex articular surface at a proximal end thereof which engages and moves relative to a socket or concave articular surface formed in a lateral aspect of the glenoid implant, although this arrangement is sometimes reversed so that the humeral implant includes the convex articular surface and the glenoid implant includes the convex articular surface. The ligaments and muscles of the shoulder surround the implants and maintain the humeral implant against the glenoid implant, while at the same time allowing relative movement therebetween.

BACKGROUND

Some existing glenoid components include a fixation peg or a fixation keel on the medial bone-facing surface. Some designs include multiple parallel pegs. The peg or keel may include surface features to enhance fixation, such as alternating ridges and grooves, flanges, and the like. The surface features frequently extend perpendicular to the axis of the peg or keel, because the primary direction of pull-out occurs along that axis. Glenoid components may experience failure by pull-out along the peg or keel axis, but other failure modes occur as well. The humerus, or humeral component, contacts the glenoid component in multiple locations on the glenoid lateral articular surface in vivo. Thus, forces which may cause loosening occur in multiple locations and along multiple vectors.

Glenoid components may experience forceful loading applied to the peripheral edge of the implant, which may cause the opposite side of the component to lift up. Forceful loading of the far posterior peripheral edge is a known common failure mechanism of glenoid components. This failure mode may be referred to as lever-out failure or rotational pull-out.

Glenoid components may also experience side-to-side translation in the superior-inferior direction or in the anterior-posterior direction. The most common direction is superior-inferior. Side-to-side translation is minimized when the implant peg, keel, or anchoring element is at least the same size as the bone tunnel into which it is inserted. However, the implant peg, keel, or anchoring element may be smaller than the bone tunnel, especially if the glenoid component will be fixed with bone cement. In this situation, the glenoid component is free to translate side-to-side, at least until the bone cement has hardened.

There is a need for an implant which resists axial pull-out, rotational pull-out (or lever-out), and translation.

The fundamental geometry of the anchoring elements disclosed herein provides inherent resistance to axial pull-out, rotational pull-out, and translation. The surface features disclosed herein are oriented in multiple planes to provide additional resistance to axial pull-out perpendicular to the back side of the glenoid component, pull-out along the axis of the dowel, and side-to-side translation in the superior-inferior or anterior-posterior directions.

SUMMARY

The various systems and methods of the present technology have been developed in response to the present state of the art, and in particular, in response to the problems and needs in the art that have not yet been fully solved by currently available arthroplasty implants. The systems and methods of the present technology may provide multi-directional resistance to pull-out and translation forces acting on the implants. The systems and methods of the present technology may provide arthroplasty prostheses or components with bone facing anchoring elements, in which at least one of the anchoring elements deforms along its long axis to provide resistance to motion in three orthogonal planes.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 8G is a medial-superior-posterior view of the glenoid component of FIG. 8A; FIG. 8H is a medial-superior-anterior view of the glenoid component of FIG. 8A; FIG. 8I is a medial-inferior-posterior view of the glenoid component of FIG. 8A; FIG. 8J is a medial-inferior-anterior view of the glenoid component of FIG. 8A.

FIG. 9A is a lateral view of another glenoid component; FIG. 9B is a medial view of the glenoid component of FIG. 9A; FIG. 9C is a posterior view of the glenoid component of FIG. 9A; FIG. 9D is an anterior view of the glenoid component of FIG. 9A; FIG. 9G is a medial-superior-posterior view of the glenoid component of FIG. 9A; FIG. 9H is a medial-superior-anterior view of the glenoid component of FIG. 9A; FIG. 9I is a medial-inferior-posterior view of the glenoid component of FIG. 9A; and FIG. 9J is a medial-inferior-anterior view of the glenoid component of FIG. 9A;

FIG. 10G is a medial-superior-posterior view of the glenoid component of FIG. 10A; FIG. 10H is a medial-superior-anterior view of the glenoid component of FIG. 10A; FIG. 10I is a medial-inferior-posterior view of the glenoid component of FIG. 10A; and FIG. 10J is a medial-inferior-anterior view of the glenoid component of FIG. 10A;

FIG. 11A is a lateral view of yet another glenoid component; FIG. 11B is a medial view of the glenoid component of FIG. 11A; FIG. 11C is a posterior view of the glenoid component of FIG. 11A; FIG. 11D is an anterior view of the glenoid component of FIG. 11A; FIG. 11E is a superior view of the glenoid component of FIG. 11A; FIG. 11F is an inferior view of the glenoid component of FIG. 11A; FIG. 11G is a medial-posterior view of the glenoid component of FIG. 11A; FIG. 11H is a medial-superior-posterior view of the glenoid component of FIG. 11A; FIG. 11I is a medial-superior-anterior view of the glenoid component of FIG. 11A; FIG. 11J is a medial-inferior-posterior view of the glenoid component of FIG. 11A; and FIG. 11K is a medial-inferior-anterior view of the glenoid component of FIG. 11A;

FIG. 12A is a lateral view of yet another glenoid component; FIG. 12B is a medial view of the glenoid component of FIG. 12A; FIG. 12C is a posterior view of the glenoid component of FIG. 12A; FIG. 12D is an anterior view of the glenoid component of FIG. 12A; FIG. 12H is a medial-superior-posterior view of the glenoid component of FIG. 12A; FIG. 12I is a medial-superior-anterior view of the glenoid component of FIG. 12A; FIG. 12J is a medial-inferior-posterior view of the glenoid component of FIG. 12A; and FIG. 12K is a medial-inferior-anterior view of the glenoid component of FIG. 12A; and FIG. 13A is a cross section of yet another glenoid component, taken across the anterior-poster width of the glenoid component; FIG. 13B is a cross section of yet another glenoid component, taken across the anterior-poster width of the glenoid component; FIG. 13C is a cross section of the glenoid component of FIG. 13A, taken across the anterior-poster width of the glenoid component, and showing a fixation element; FIG. 13D is a cross section of yet another glenoid component, taken across the anterior-poster width of the glenoid component; FIG. 13E is a cross section of the glenoid component of FIG. 13B, taken across the anterior-poster width of the glenoid component; FIG. 13F is a cross section of yet another glenoid component, taken across the anterior-poster width of the glenoid component; FIG. 13G is a cross section of the glenoid component of FIG. 13B, taken across the anterior-poster width of the glenoid component; FIG. 13H is a cross section of the glenoid component of FIG. 13F, taken across the anterior-posterior width of the glenoid component, omitting a fixation element shown in FIG. 13F; FIG. 13I is a lateral view of yet another glenoid component; and FIG. 13J is a lateral view of yet another glenoid component.

DETAILED DESCRIPTION

Figure 1A:
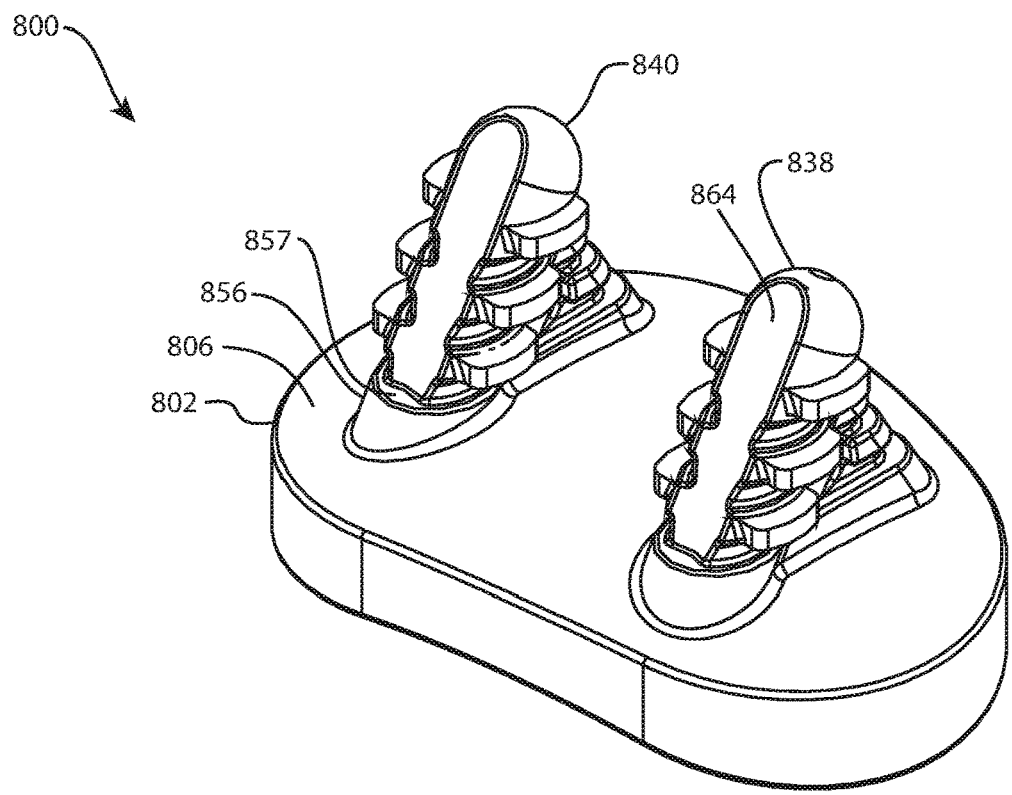
FIG. 1A is an isometric view of a left glenoid component.
Figure 1B:
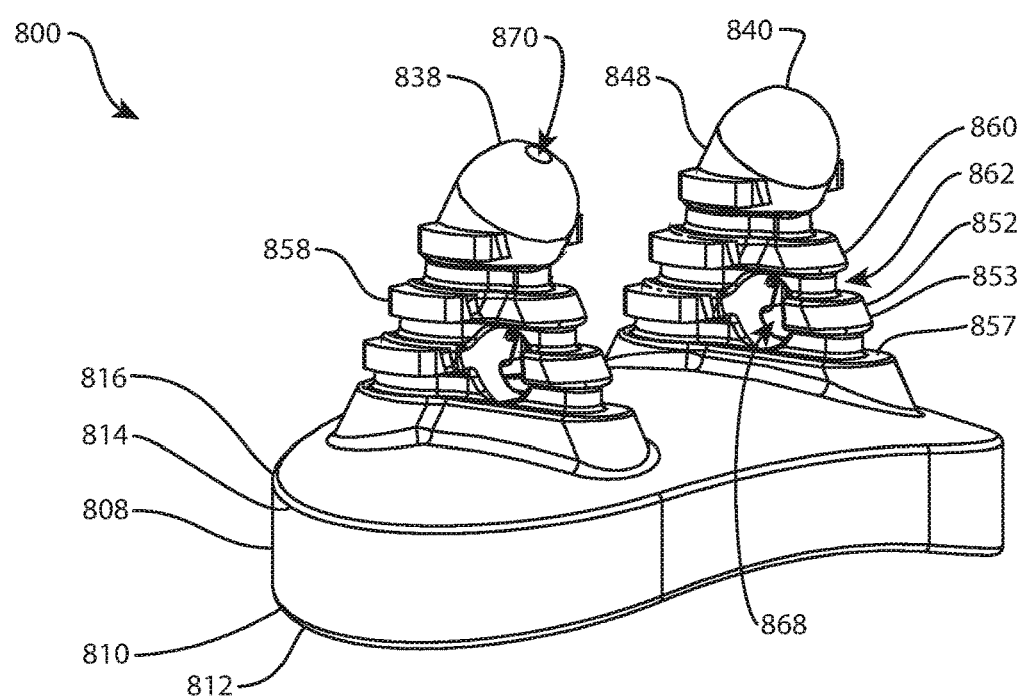
FIG. 1B is an oblique view of the glenoid component of FIG. 1A.
Figure 1C:
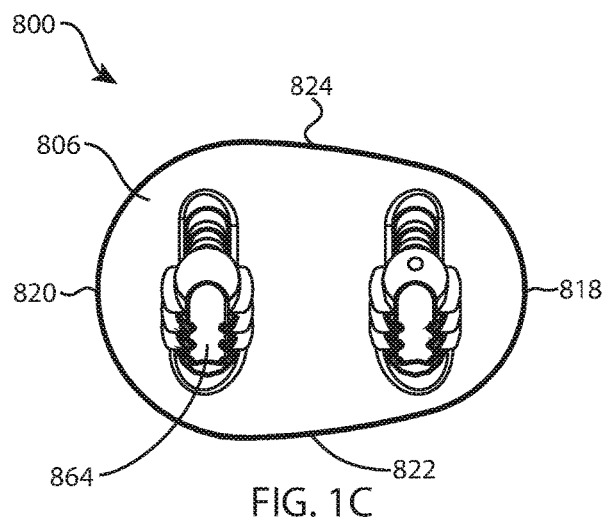
FIG. 1C is a medial view of the glenoid component of FIG. 1A.
Figure 1E:
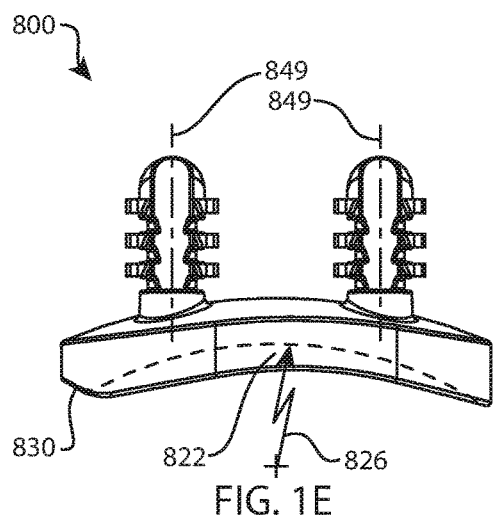
FIG. 1E is an anterior view of the glenoid component of FIG. 1A.
Figure 1D:
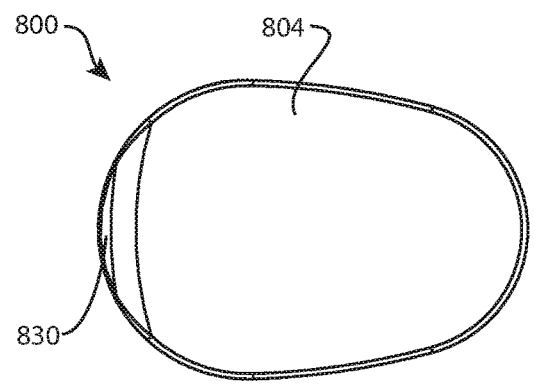
FIG. 1D is a lateral view of the glenoid component of FIG. 1A.
Figure 1F:
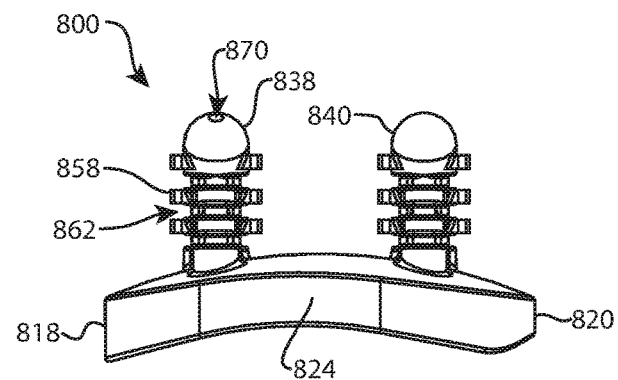
FIG. 1F is a posterior view of the glenoid component of FIG. 1A.
Figure 1G:
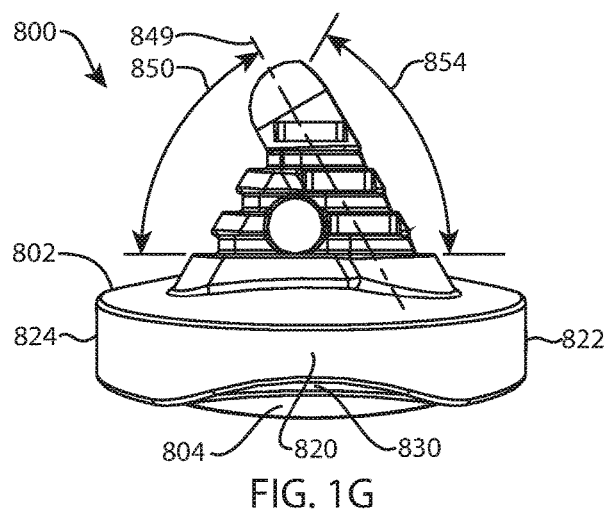
FIG. 1G is an inferior view of the glenoid component of FIG. 1A.
Figure 1H:
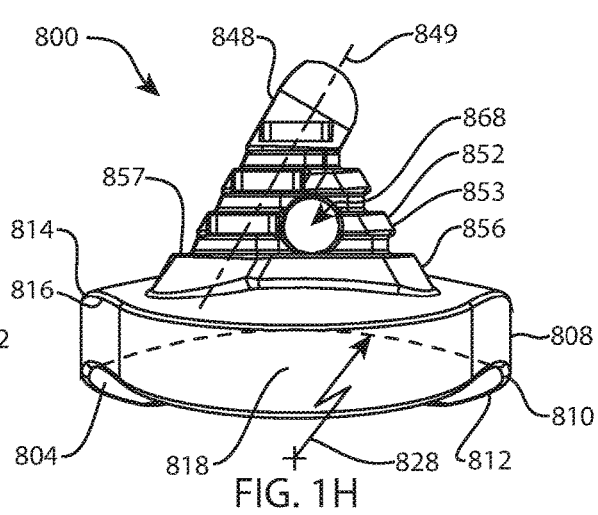
FIG. 1H is a superior view of the glenoid component of FIG. 1A.
Figure 2A:
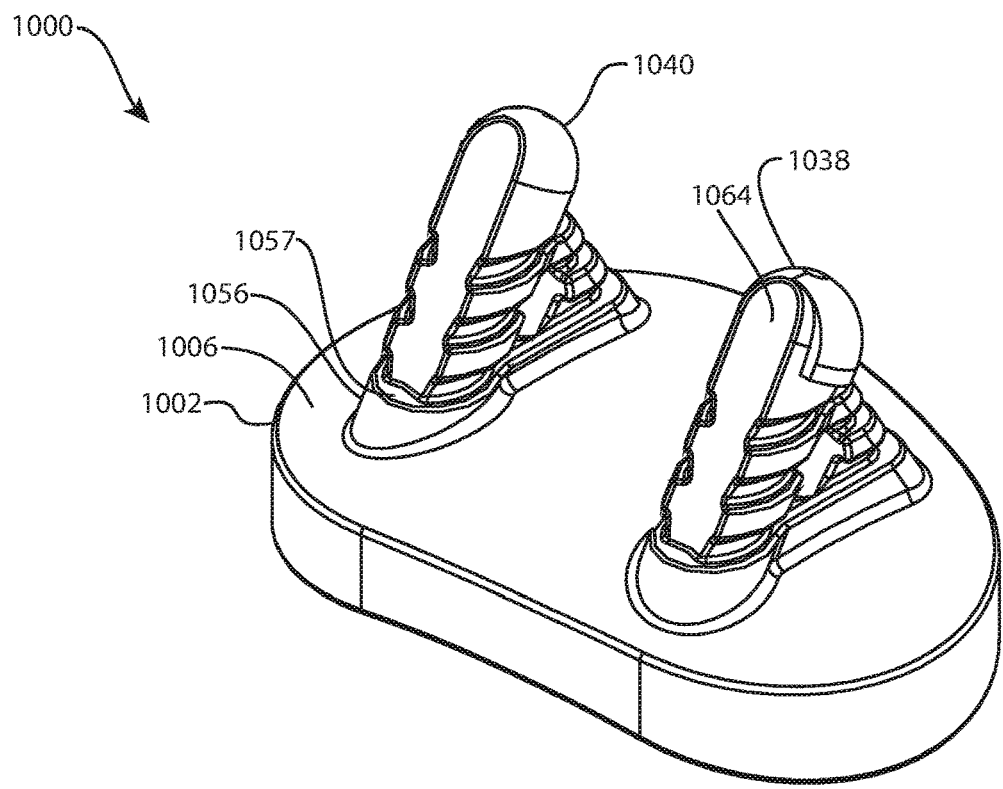
FIG. 2A is an isometric view of another left glenoid component.
Figure 2B:
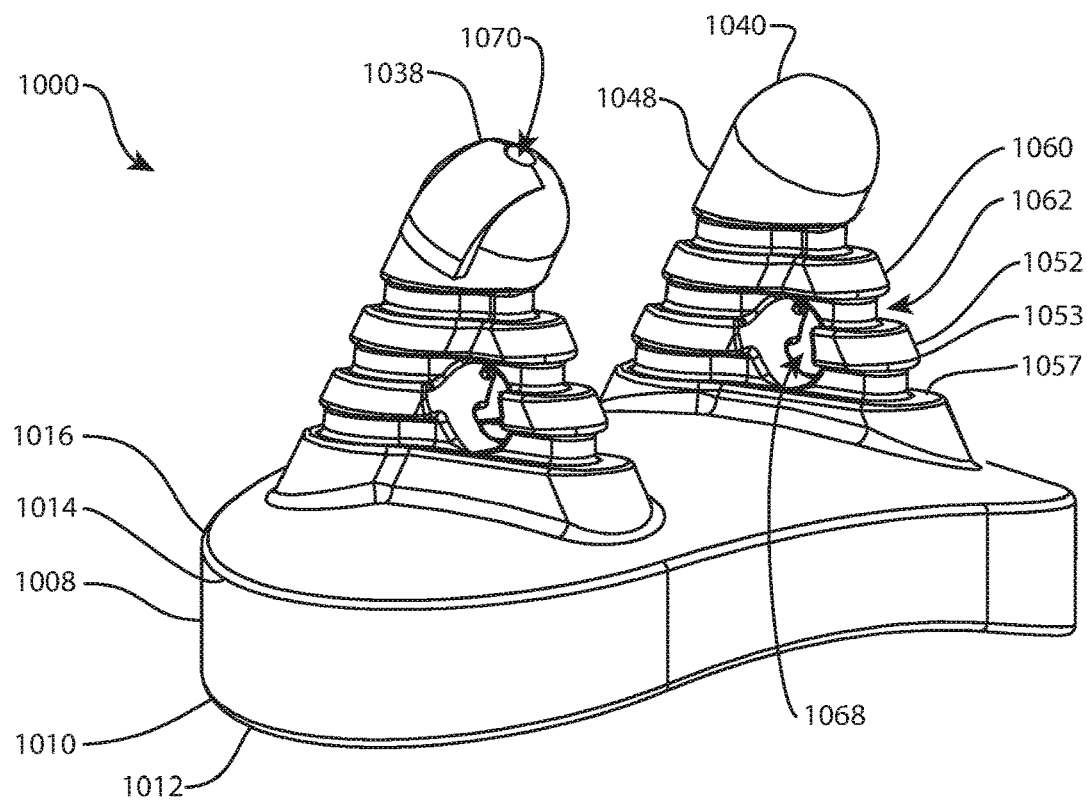
FIG. 2B is an oblique view of the glenoid component of FIG. 2A.
Figure 2C:
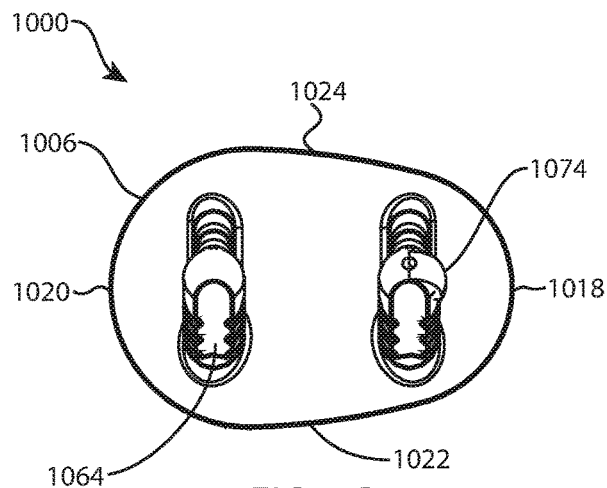
FIG. 2C is a medial view of the glenoid component of FIG. 2A.
Figure 2E:
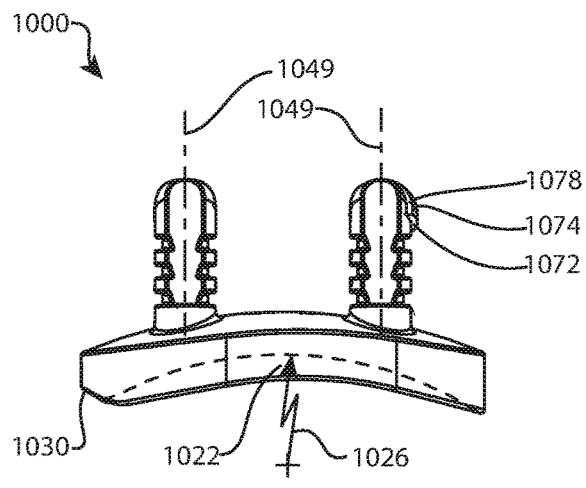
FIG. 2E is an anterior view of the glenoid component of FIG. 2A.
Figure 2D:
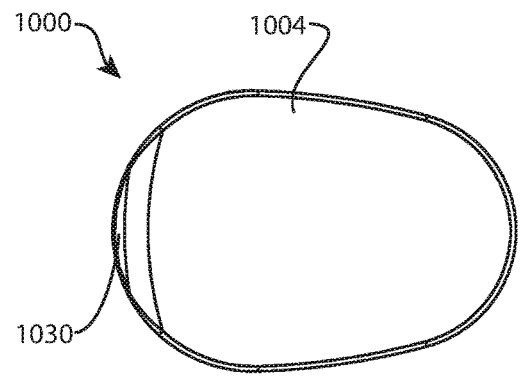
FIG. 2D is a lateral view of the glenoid component of FIG. 2A.
Figure 2F:
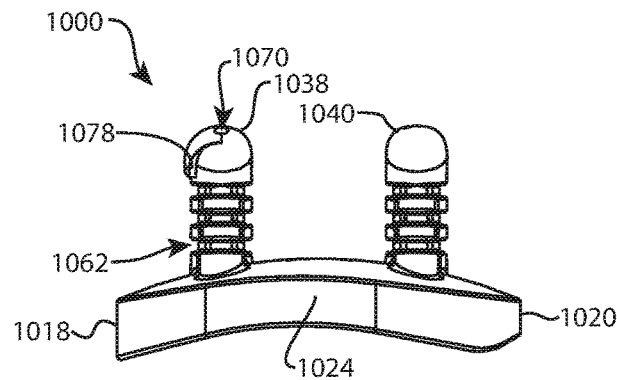
FIG. 2F is a posterior view of the glenoid component of FIG. 2A.
Figure 2G:
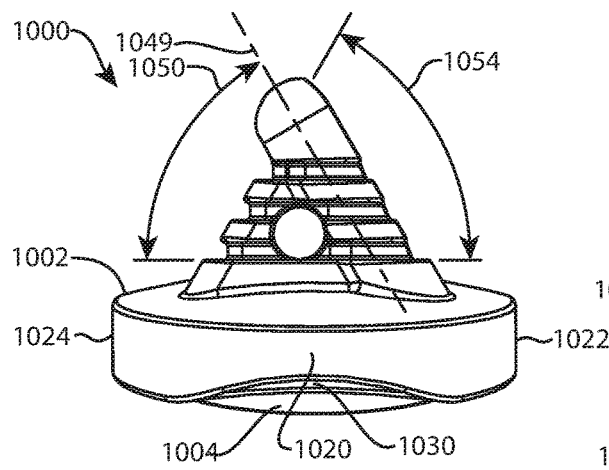
FIG. 2G is an inferior view of the glenoid component of FIG. 2A.
Figure 2H:
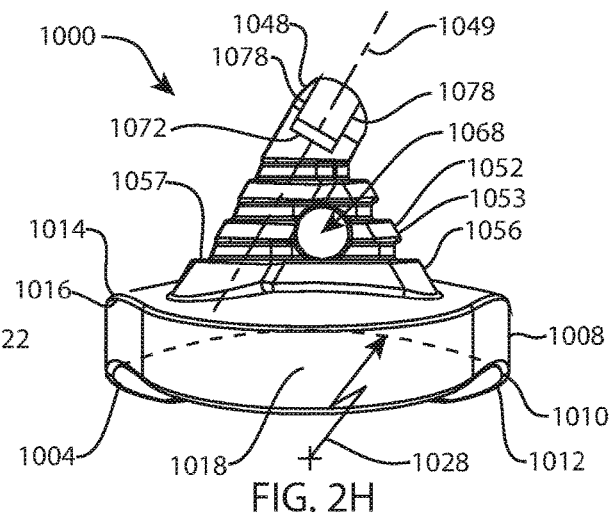
FIG. 2H is a superior view of the glenoid component of FIG. 2A.
Figure 3A:
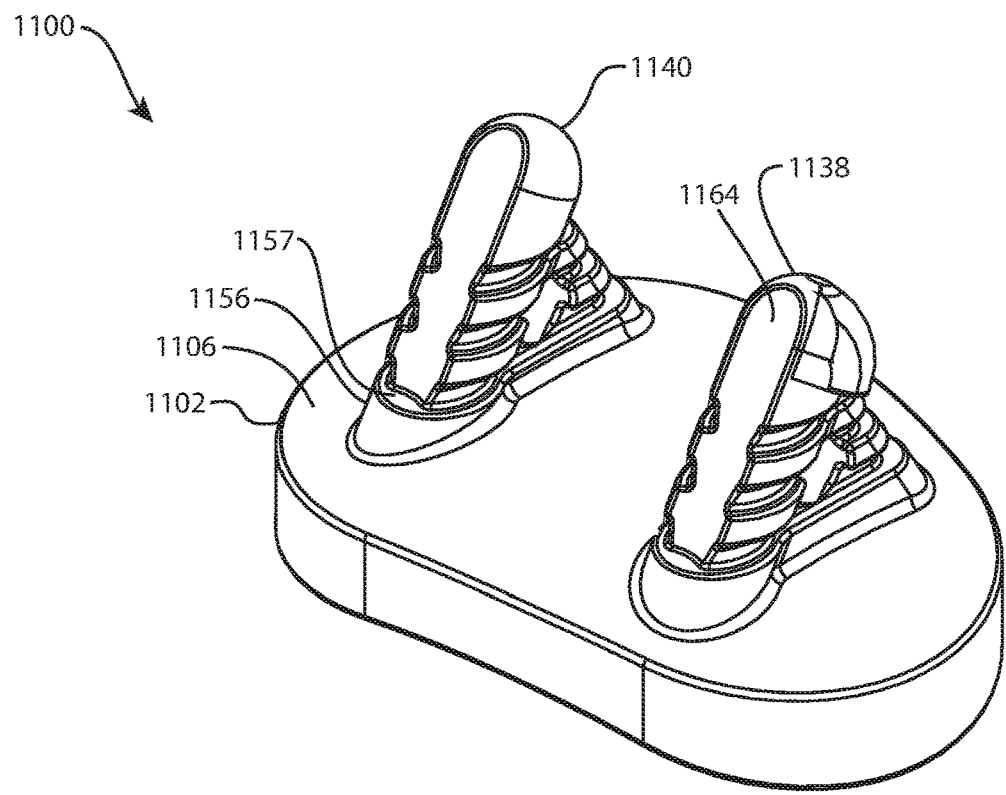
FIG. 3A is an isometric view of yet another left glenoid component.
Figure 3B:
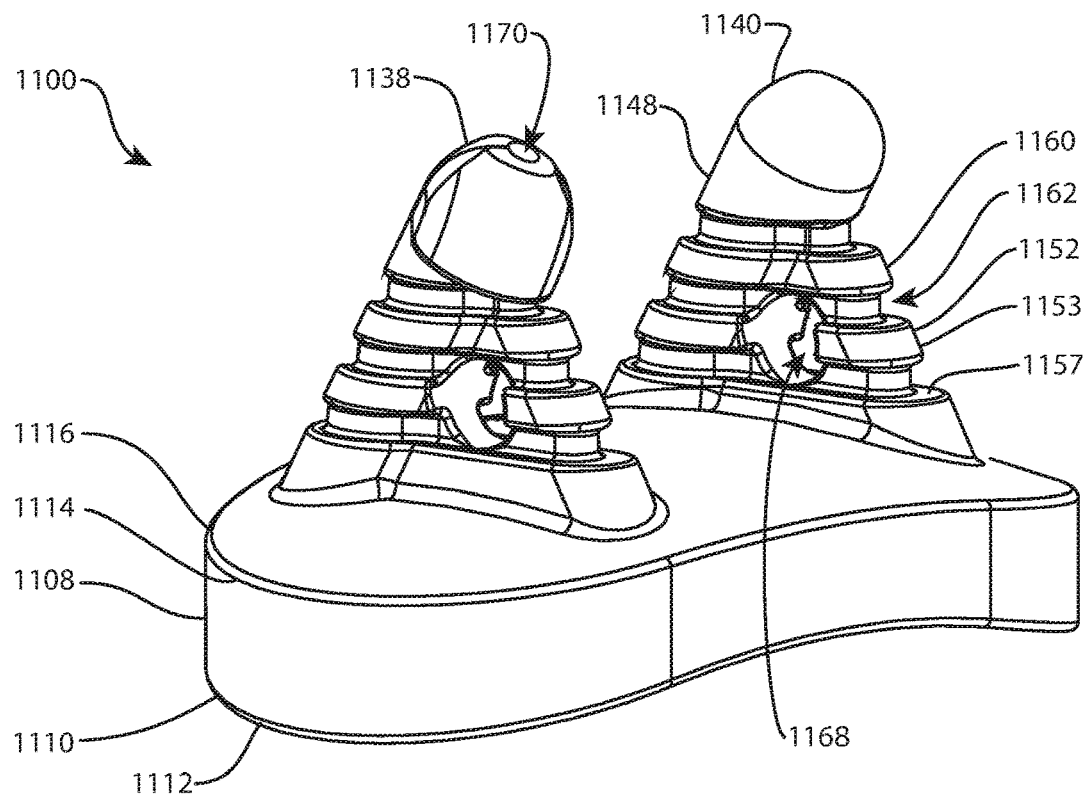
FIG. 3B is an oblique view of the glenoid component of FIG. 3A.
Figure 3C:
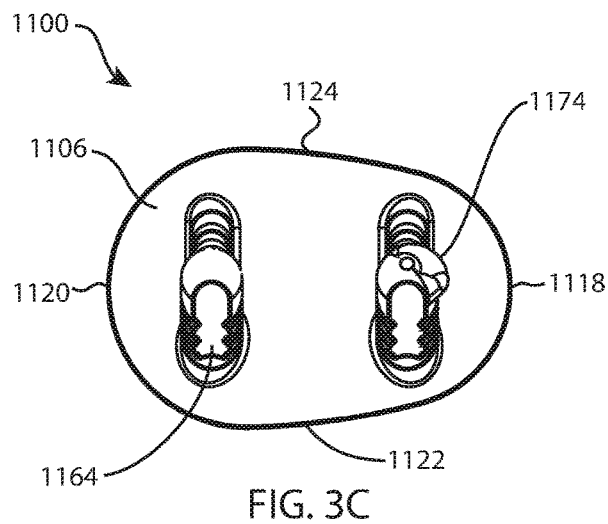
FIG. 3C is a medial view of the glenoid component of FIG. 3A.
Figure 3E:
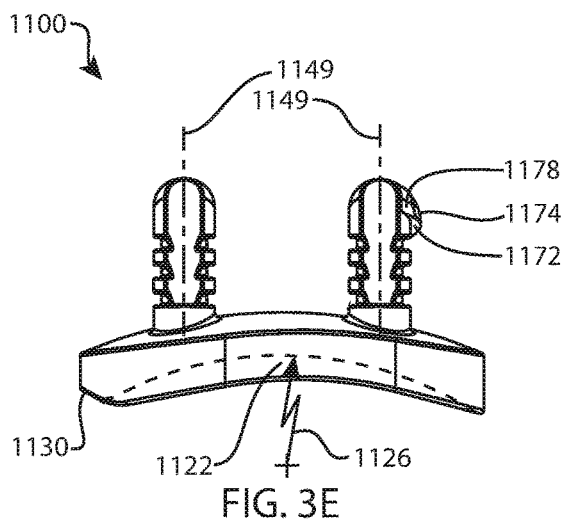
FIG. 3E is an anterior view of the glenoid component of FIG. 3A.
Figure 3D:
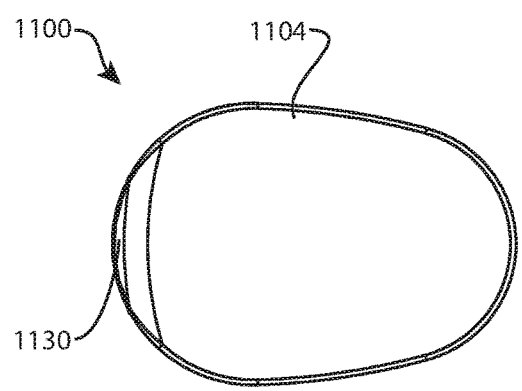
FIG. 3D is a lateral view of the glenoid component of FIG. 3A.
Figure 3F:
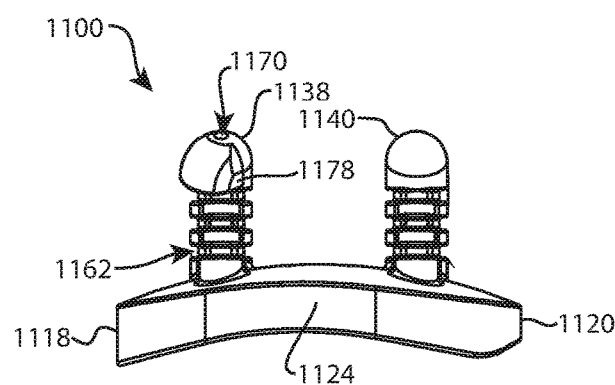
FIG. 3F is a posterior view of the glenoid component of FIG. 3A.
Figure 3G:
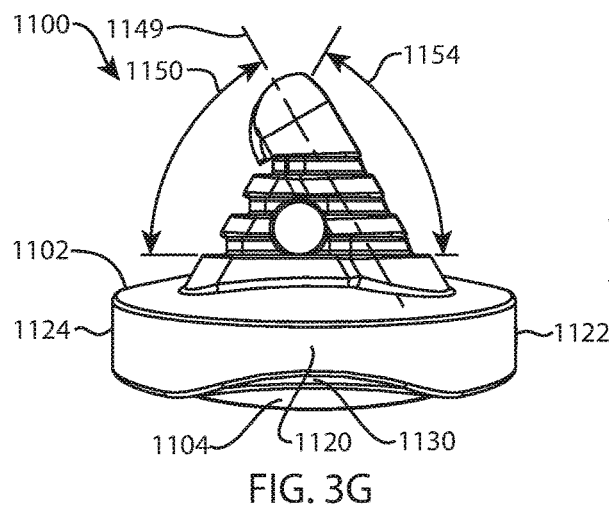
FIG. 3G is an inferior view of the glenoid component of FIG. 3A.
Figure 3H:
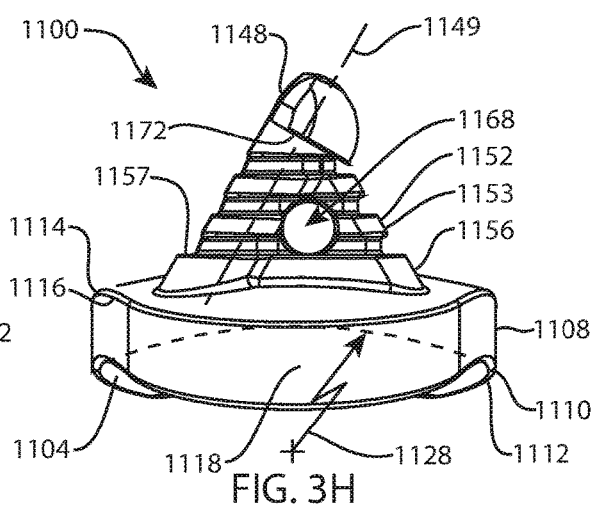
FIG. 3H is a superior view of the glenoid component of FIG. 3A.
Figure 4A:
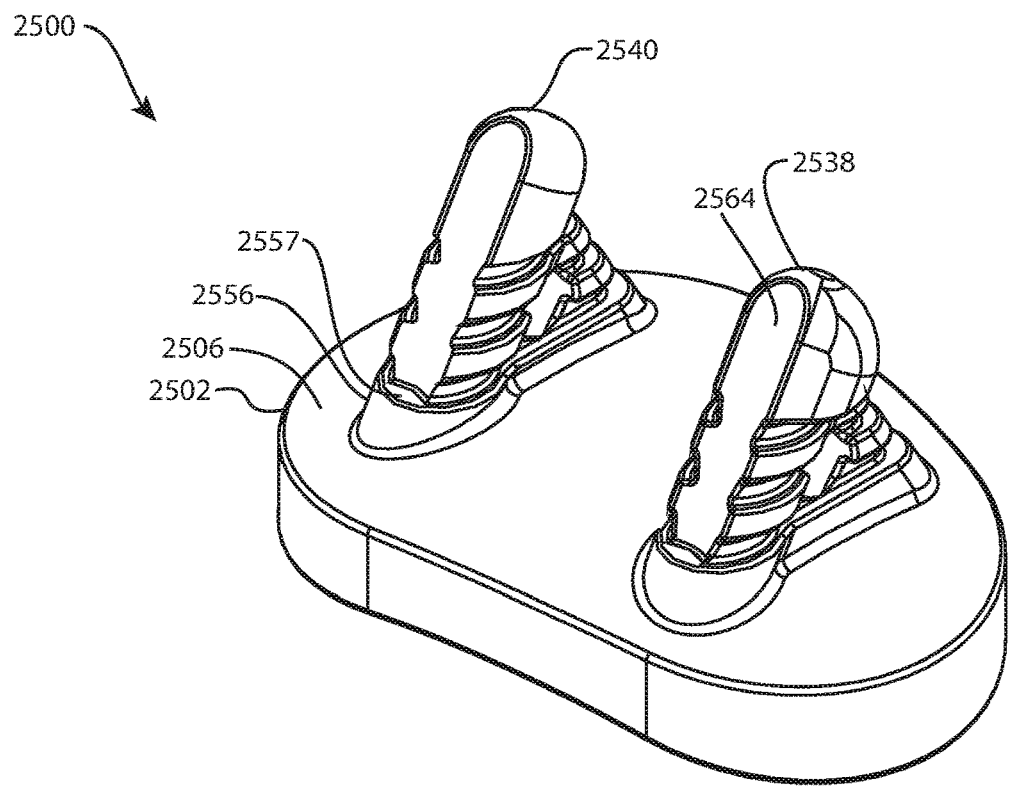
FIG. 4A is an isometric view of yet another left glenoid component.
Figure 4B:
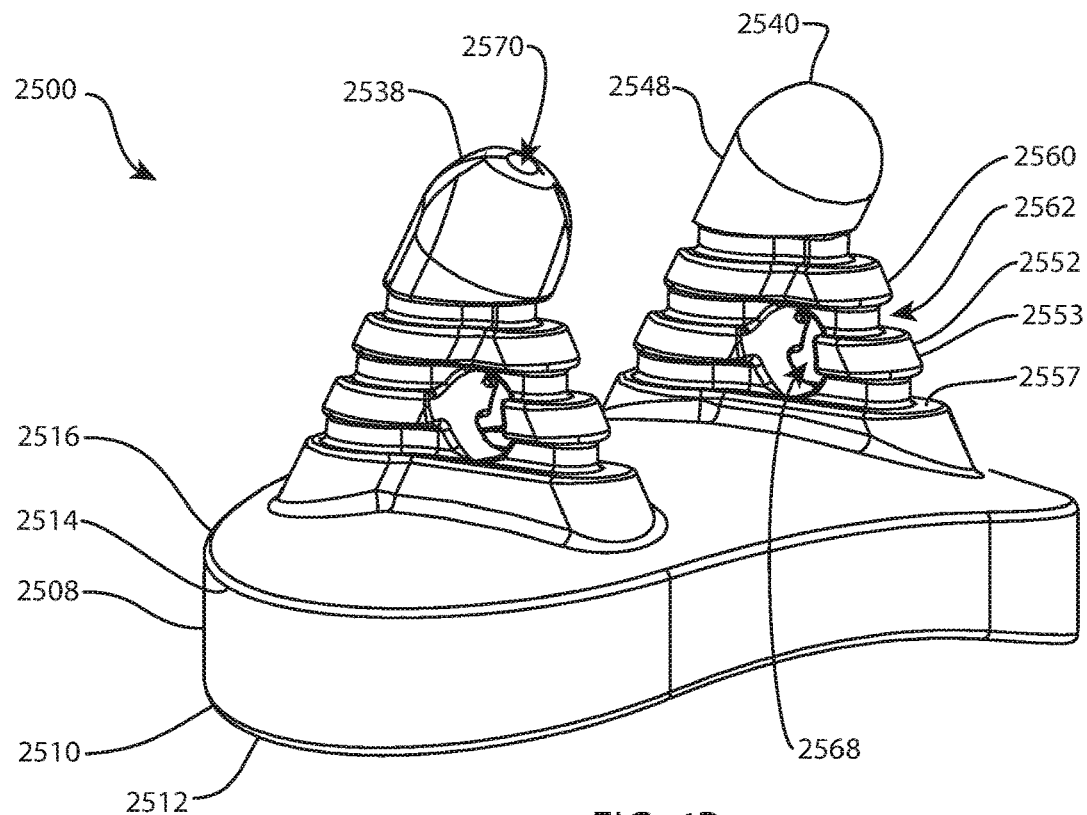
FIG. 4B is an oblique view of the glenoid component of FIG. 4A.
Figure 4C:
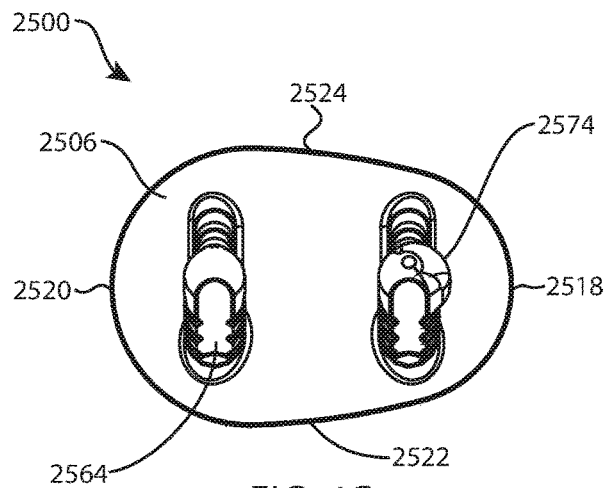
FIG. 4C is a medial view of the glenoid component of FIG. 4A.
Figure 4E:
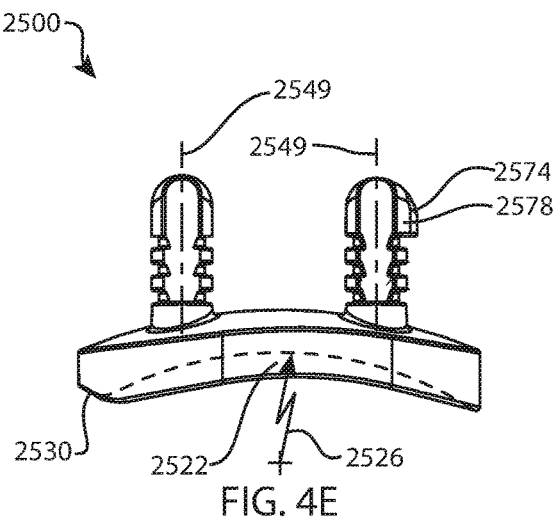
FIG. 4E is an anterior view of the glenoid component of FIG. 4A.
Figure 4D:
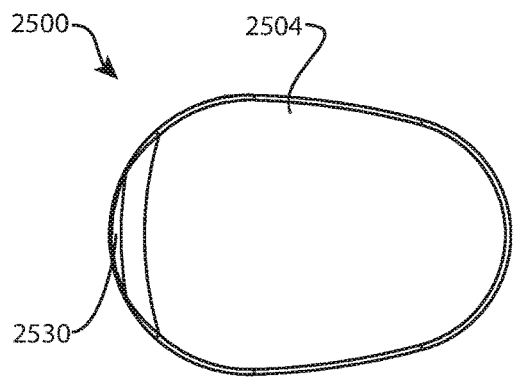
FIG. 4D is a lateral view of the glenoid component of FIG. 4A.
Figure 4F:
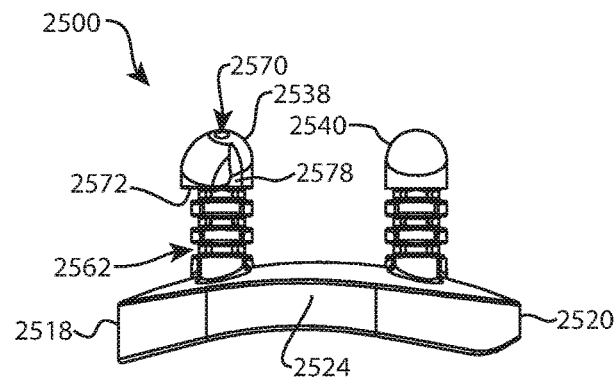
FIG. 4F is a posterior view of the glenoid component of FIG. 4A.
Figure 4G:
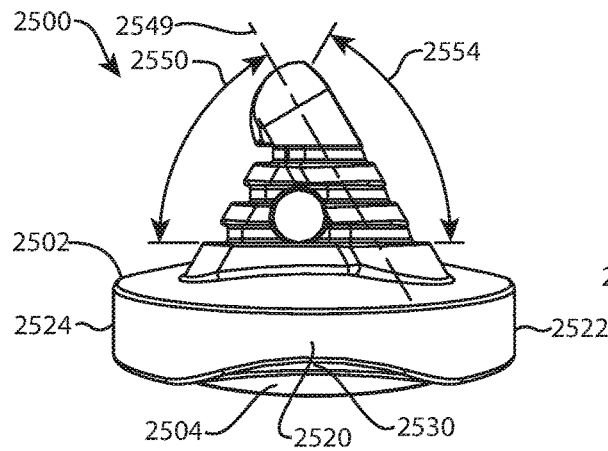
FIG. 4G is an inferior view of the glenoid component of FIG. 4A.
Figure 4H:
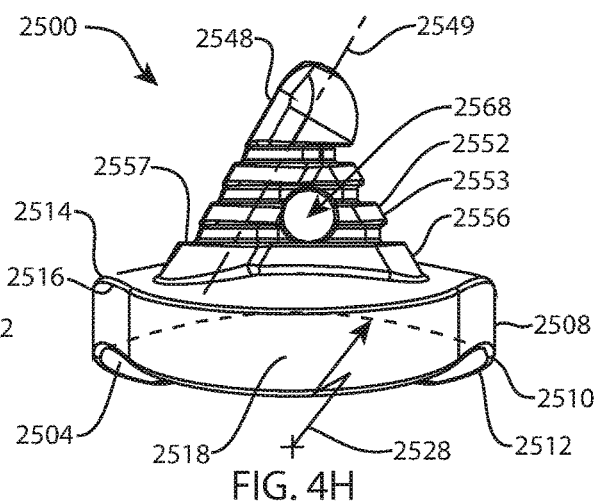
FIG. 4H is a superior view of the glenoid component of FIG. 4A.
Figure 5A:
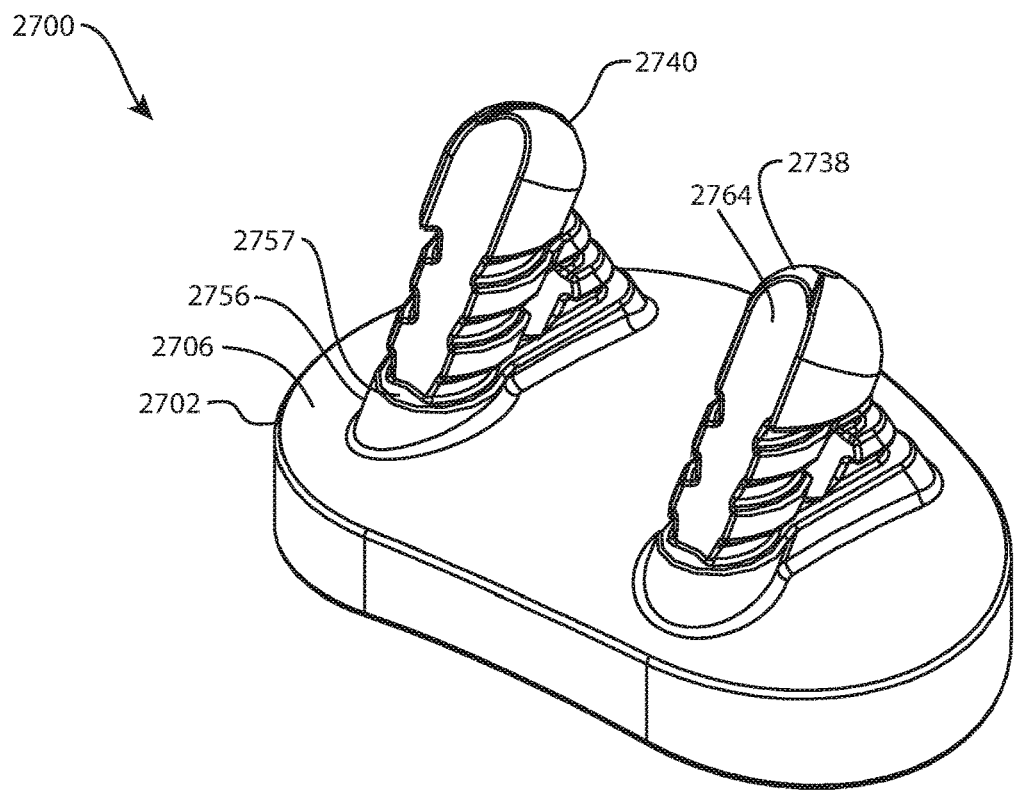
FIG. 5A is an isometric view of yet another left glenoid component.
Figure 5B:
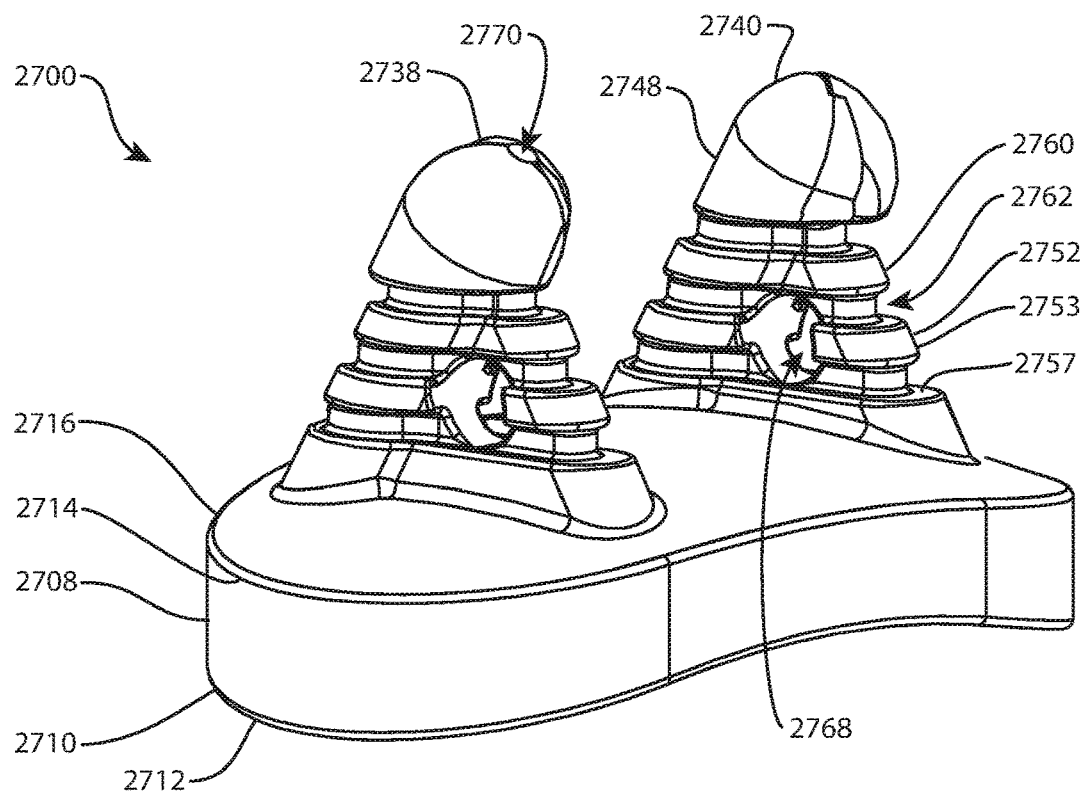
FIG. 5B is an oblique view of the glenoid component of FIG. 5A.
Figure 5C:
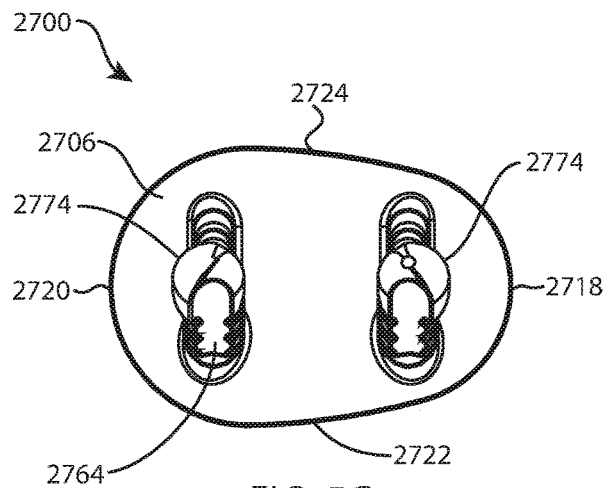
FIG. 5C is a medial view of the glenoid component of FIG. 5A.
Figure 5E:
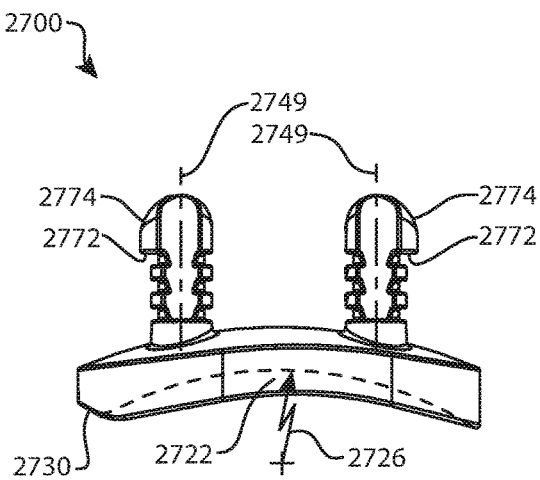
FIG. 5E is an anterior view of the glenoid component of FIG. 5A.
Figure 5D:
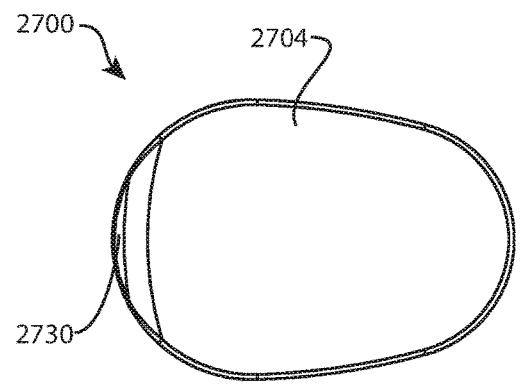
FIG. 5D is a lateral view of the glenoid component of FIG. 5A.
Figure 5F:
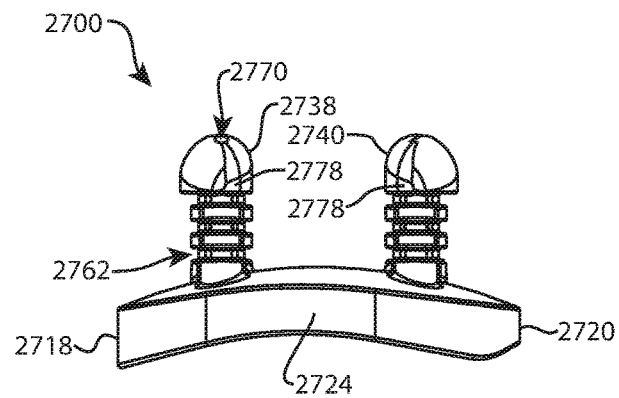
FIG. 5F is a posterior view of the glenoid component of FIG. 5A.
Figure 5G:
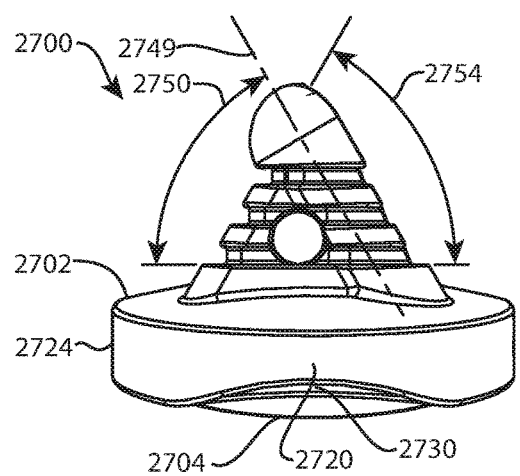
FIG. 5G is an inferior view of the glenoid component of FIG. 5A.
Figure 5H:
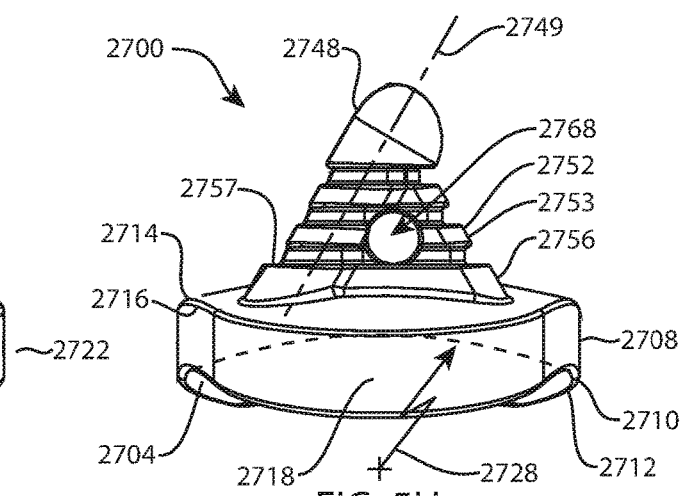
FIG. 5H is a superior view of the glenoid component of FIG. 5A.
Figure 6A:
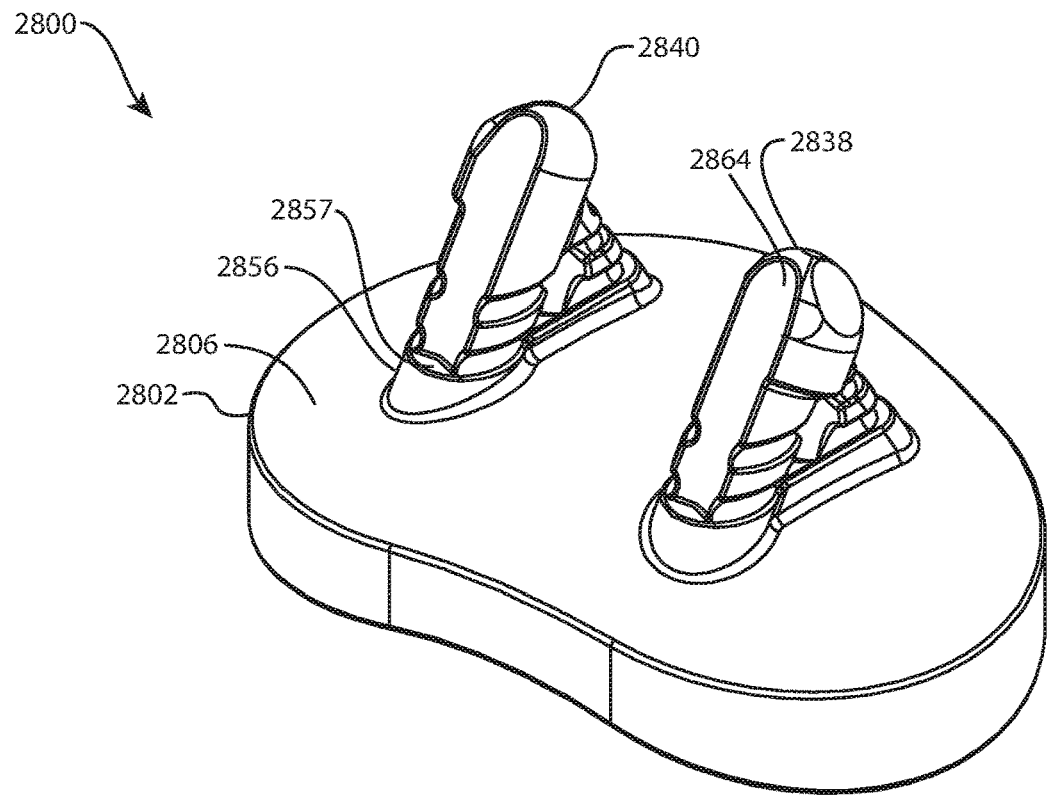
FIG. 6A is an isometric view of yet another left glenoid component.
Figure 6B:
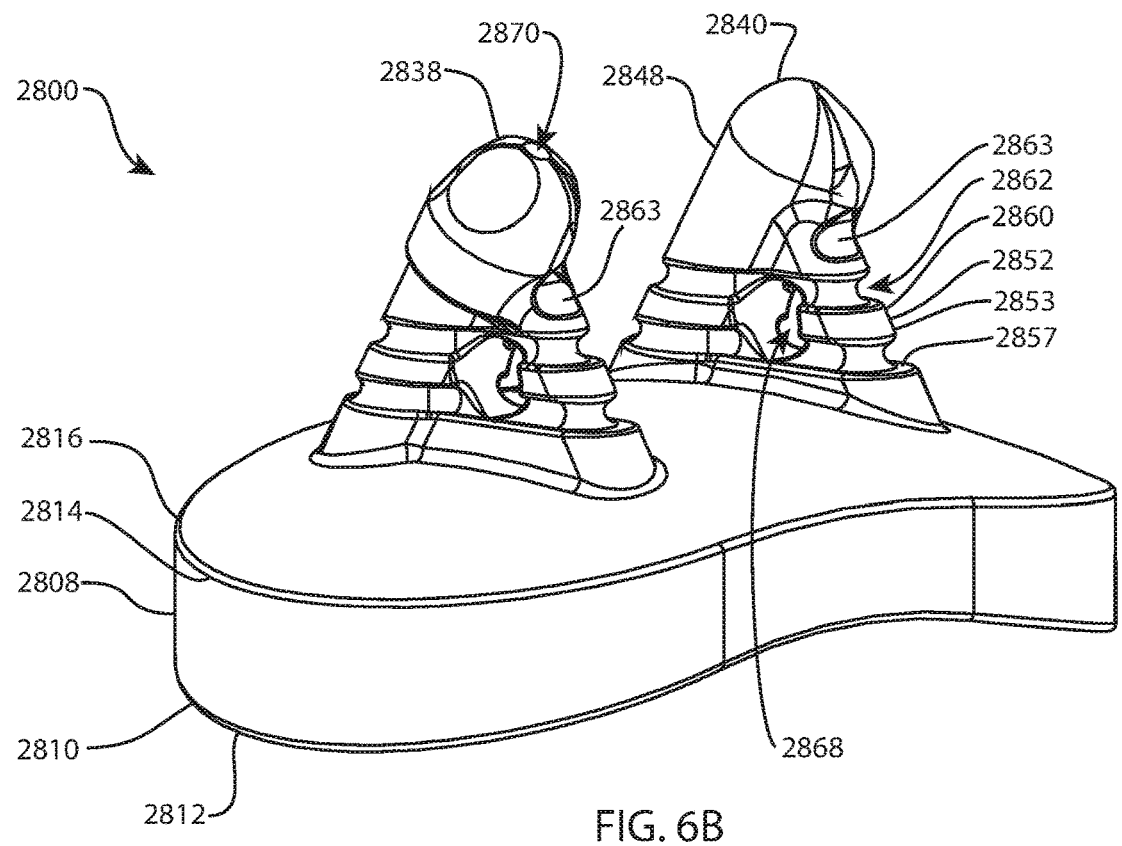
FIG. 6B is an oblique view of the glenoid component of FIG. 6A.
Figure 6C:
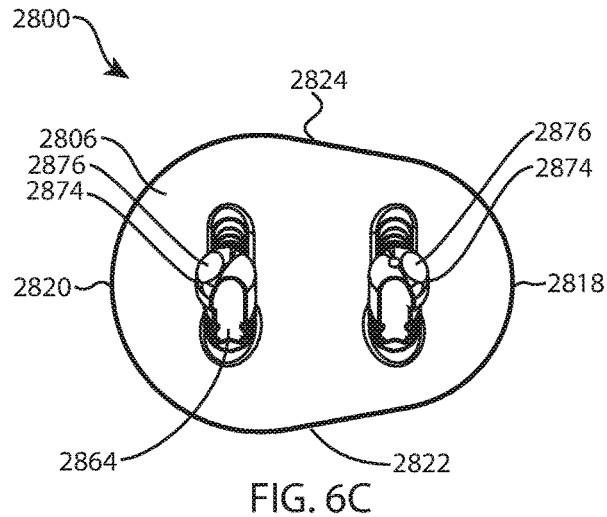
FIG. 6C is a medial view of the glenoid component of FIG. 6A.
Figure 6E:
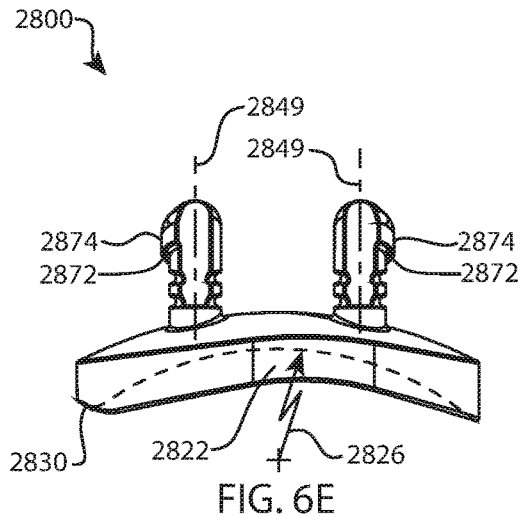
FIG. 6E is an anterior view of the glenoid component of FIG. 6A.
Figure 6D:
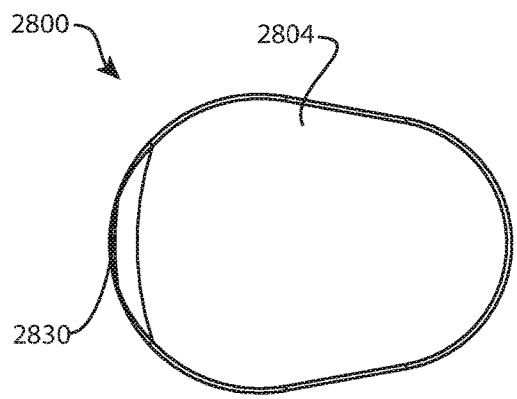
FIG. 6D is a lateral view of the glenoid component of FIG. 6A.
Figure 6F:
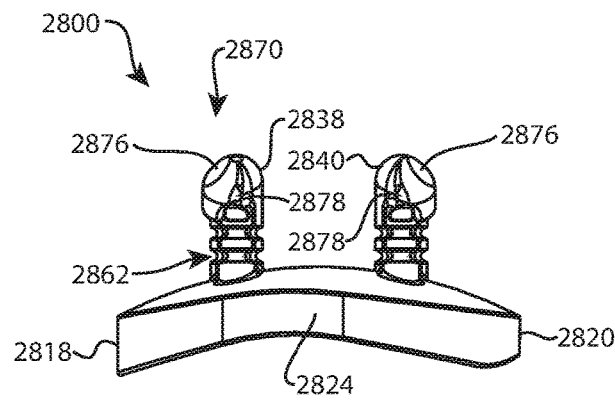
FIG. 6F is a posterior view of the glenoid component of FIG. 6A.
Figure 6G:
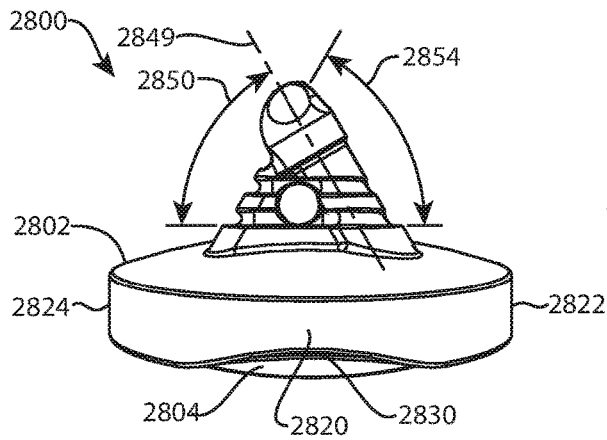
FIG. 6G is an inferior view of the glenoid component of FIG. 6A.
Figure 6H:
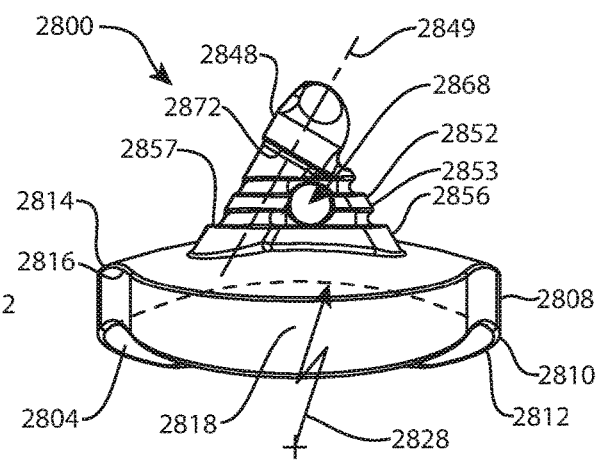
FIG. 6H is a superior view of the glenoid component of FIG. 6A.
Figure 7A:
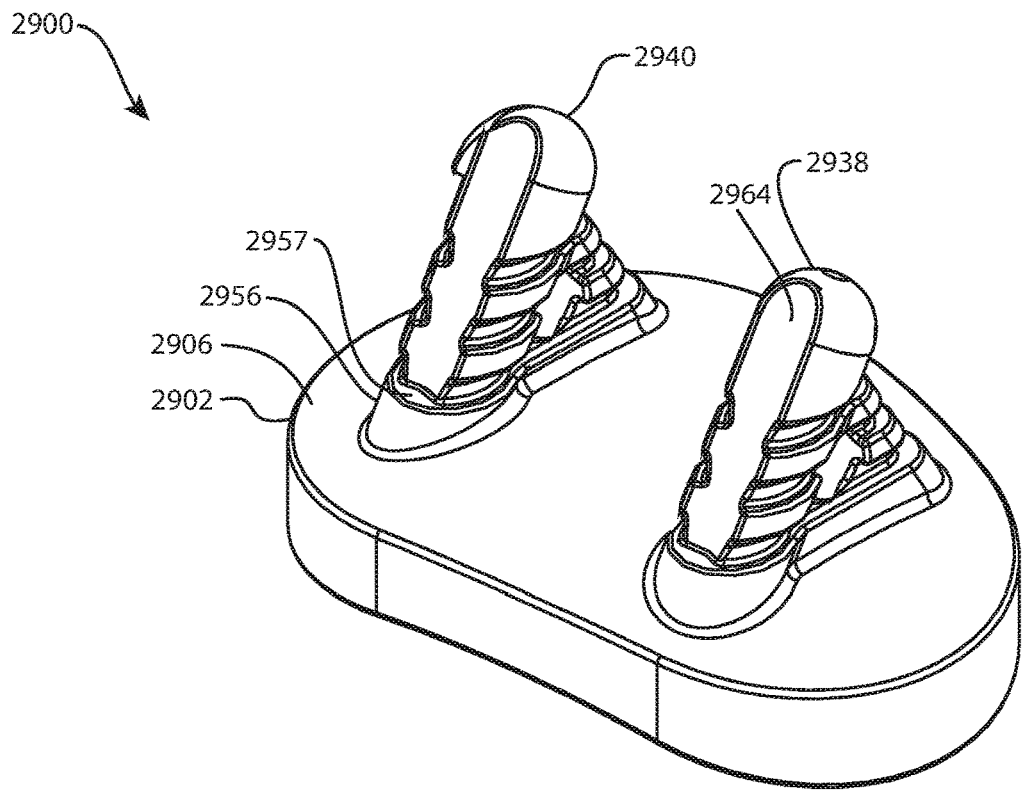
FIG. 7A is an isometric view of yet another left glenoid component.
Figure 7B:
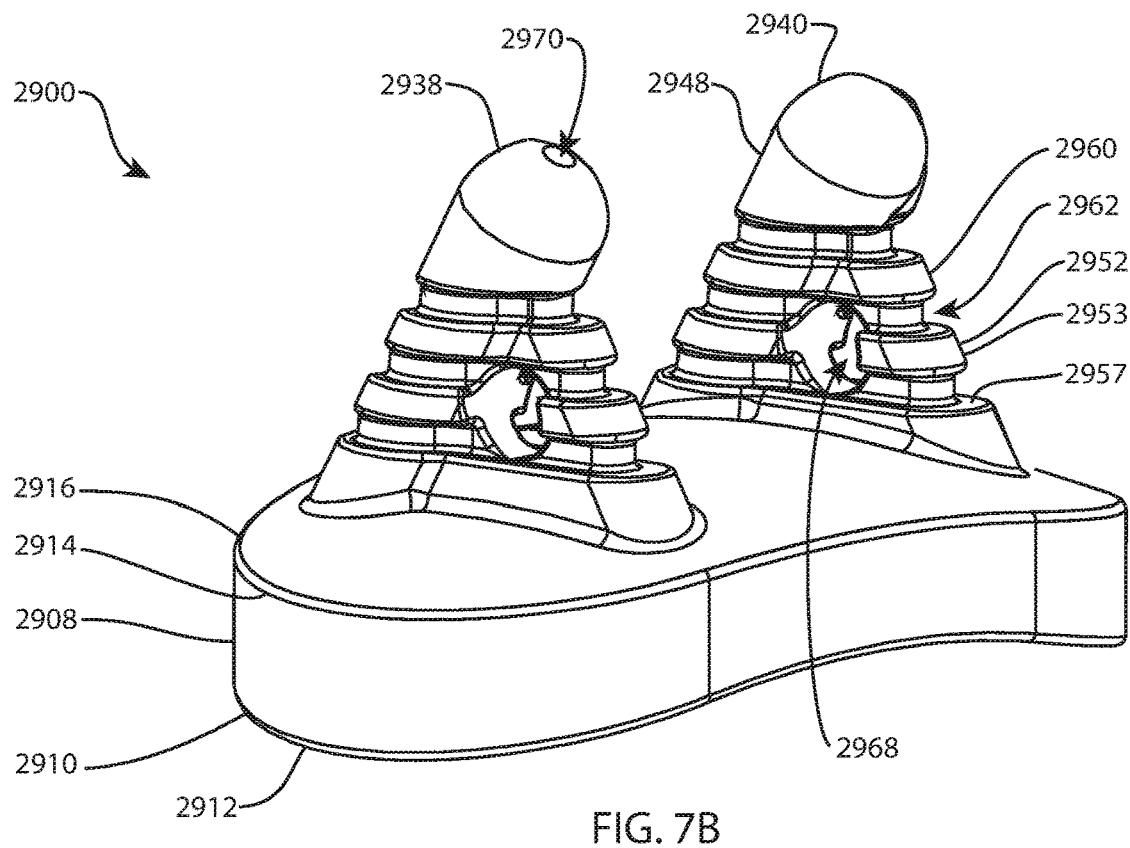
FIG. 7B is an oblique view of the glenoid component of FIG. 7A.
Figure 7C:
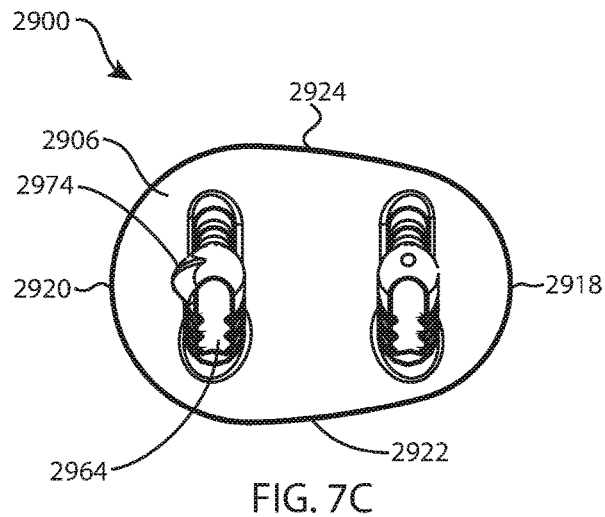
FIG. 7C is a medial view of the glenoid component of FIG. 7A.
Figure 7E:
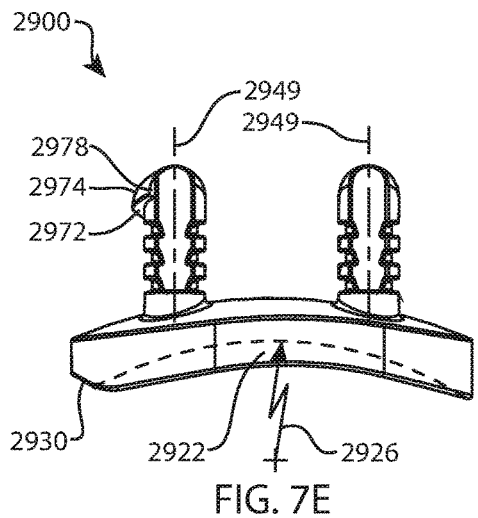
FIG. 7E is an anterior view of the glenoid component of FIG. 7A.
Figure 7D:
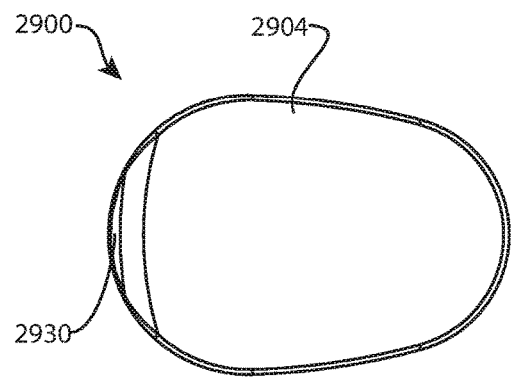
FIG. 7D is a lateral view of the glenoid component of FIG. 7A.
Figure 7F:
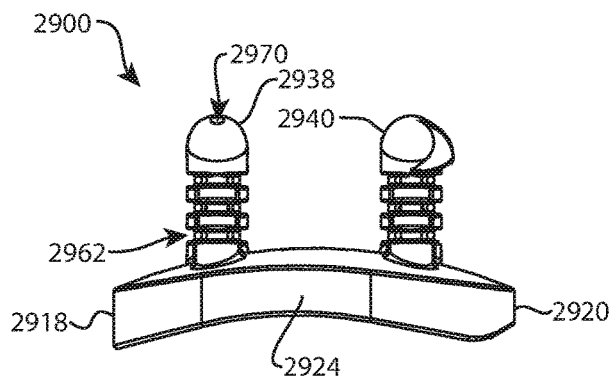
FIG. 7F is a posterior view of the glenoid component of FIG. 7A.
Figure 7G:
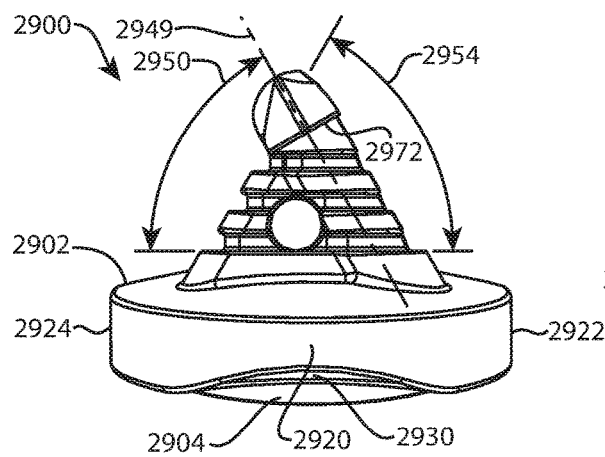
FIG. 7G is an inferior view of the glenoid component of FIG. 7A.
Figure 7H:
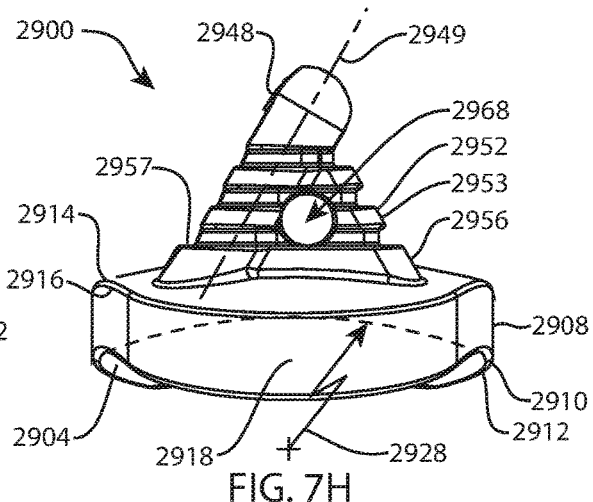
FIG. 7H is a superior view of the glenoid component of FIG. 7A.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. A sagittal plane divides a body into right and left portions. A mid-sagittal plane divides the body into bilaterally symmetric right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

Standard medical terminology relating to shoulder anatomy and shoulder arthroplasty is employed in this specification with the ordinary and customary meanings.

Referring to FIGS. 1A-1H, a glenoid component 800 includes a body 802 with a lateral articular surface 804 and an opposite medial bone-facing surface 806.

A peripheral wall 808 extends around the body 802 between the surfaces 804, 806. A lateral peripheral edge 810 extends around the body 802 where the lateral articular surface 804 intersects the peripheral wall 808. The lateral peripheral edge 810 may be rounded or relieved by a lateral peripheral relief 812, such as a radius, fillet, chamfer, bevel, or the like. A medial peripheral edge 814 extends around the body 802 where the medial bone-facing surface 806 intersects the peripheral wall 808. The medial peripheral edge 814 may be rounded or relieved by a medial peripheral relief 816, such as a radius, fillet, chamfer, bevel, or the like.

The body 802, lateral articular surface 804, medial bone-facing surface 806, peripheral wall 808, lateral peripheral edge 810, lateral peripheral relief 812, medial peripheral edge 814, and/or medial peripheral relief 816 may be divided into a superior portion 818, an inferior portion 820, an anterior portion 822, and a posterior portion 824. The body 802, lateral articular surface 804, and/or medial bone-facing surface 806 may also be divided into a peripheral portion near the peripheral wall 808 and an interior or central portion. In examples other than shoulder glenoid components, where the surgical approach trajectory may be different than the approach described herein, the appropriate medical directional terms may be readily substituted by one of skill in the art.

The lateral articular surface 804 may be concave as shown, planar, or convex in order to complement a natural or prosthetic humeral articular surface. The lateral articular surface 804 may be spherical. The lateral articular surface 804 may be elliptical or ovoid. The lateral articular surface 804 may have a first radius 826 which is dimensionally different from, i.e., larger or smaller than, a second radius 828. The first radius 826 may be a superior-inferior radius, or S-I radius. The second radius 828 may be an anterior-posterior radius, or A-P radius.

The inferior portion 820 of the body 802 may include an inferior chamfer 830 which extends between the lateral articular surface 804 and the peripheral wall 808. The inferior chamfer 830 is a sloping surface, preferably a planar surface, that lowers the profile and thickness of the inferior portion 820 along the lateral peripheral edge 810.

The medial bone-facing surface 806 may be convex as shown, planar, or concave.

The glenoid component 800 includes at least one anchoring element 838 which protrudes outwardly from the medial bone-facing surface 806. The example shown includes a superior anchoring element 838 and an inferior anchoring element 840, although any number of anchoring elements may be present. Each anchoring element may be independently positioned on the medial bone-facing surface 806, and may be independently sized.

Each anchoring element 838, 840 includes a dowel 848, or mast, and a triangular reinforcement plate 852, or sail or buttress.

The dowel 848 projects from the medial bone-facing surface 806 at an angle 850 less than ninety degrees and greater than zero degrees. The angle 850 may be referred to as a dowel angle or a mast angle. The angle 850 may be measured between a central longitudinal axis 849 of the dowel 848 and a plane which is coplanar with the medial bone-facing surface 806, if surface 806 is planar, or a plane which is tangent to the medial bone-facing surface 806, if surface 806 is concave or convex. The plane may be tangent to the medial bone-facing surface 806 at an intersection point between the central longitudinal axis 849 of the dowel 848 and the medial bone-facing surface 806, or at a centroid of the medial bone-facing surface 806. The dowel 848 may project from the anterior portion 822 of the body 802, as shown, or from another portion of the body 802. In the example shown, the dowels 848 of anchoring elements 838, 840 project from peripheral locations in the anterior portion 822 and terminate in medially located free ends. The dowel 848 may have a round fundamental cross sectional shape, as shown, or another shape, such as a rectangle or dovetail. The dowel 848 may include a hole 870, which may receive a radiographic marker.

The reinforcement plate 852 projects from the medial bone-facing surface 806 in the acute angle 850 between the dowel 848 and the medial bone-facing surface 806, and coplanar with the dowel 848. An exposed side 853 of the reinforcement plate 852 projects from the medial bone-facing surface 806 at an angle 854 less than ninety degrees and greater than zero degrees. The angle 854 may be referred to as a reinforcement angle. The angle 854 opens toward the angle 850, and the sum of angles 850 and 854 is greater than zero degrees and less than one hundred eighty degrees. The reinforcement plate 852 intersects the dowel 848 to form a triangular shape with one side formed by the medial bone-facing surface 806, one side formed by the dowel 848, and one side formed by the exposed side 853 of the reinforcement plate 852. The triangular shape may be an acute triangle having three internal angles each less than 90 degrees.

The anchoring elements 838, 840 may include a pedestal 856 or footing where the anchoring element intersects the medial bone-facing surface 806. The pedestal 856 may be present on the dowel 848 or the reinforcement plate 852, or both. The pedestal 856 may enlarge the anchoring element 838, 840 at the medial bone-facing surface 806. The pedestal 856 may terminate medially in a planar face 857 which may establish the plane from which the angles 850, 854 are measured. The planar face 857 may be tangent to the medial bone-facing surface 806.

The anchoring elements 838, 840, including the dowels 848, the reinforcement plates 852, and the pedestals 856, may project outwardly from the medial bone-facing surface 806 orthogonally or at an acute angle when viewed from an anterior (i.e., FIG. 1E) or posterior (i.e., FIG. 1F) direction. The acute angle may be on either side of the anchoring element, i.e., on the superior or inferior side. For example, the acute angle may be on the superior side of the superior anchoring element 838, and on the inferior side of the inferior anchoring element 840, or vice versa.

The anchoring elements 838, 840 may include surface features to improve fixation, or pull-out strength, after implantation. Surface features may be present on one or more of the anchoring elements present on a glenoid component. The surface features may project outwardly or inwardly from the fundamental surface(s) of the anchoring elements 838, 840. The surface features may include notches, grooves, channels, ridges, accordion texture, barbs, threads, shelves, rings, ribs, or perforations. For example, alternating ridges 860 and grooves 862 are shown, as well as fenestrations 868 extending through the anchoring elements 838, 840. The illustrated ridges 860 and grooves 862 are oriented to resist axial pull-out, i.e., forces acting perpendicular to the back side of the glenoid component, or the face 857 described below. The illustrated fenestrations 868 resist forces acting perpendicular to their central longitudinal axes. All of these surface features may facilitate bony ingrowth or bone cement interdigitation.

A particular surface feature may be oriented on an axis parallel to and offset from the corresponding axis of the fundamental surface of the corresponding anchoring element 838 or 840. For example, the dowel 848 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 838, 840 to bend when inserted into the bone tunnel.

The anchoring elements 838, 840 may include at least two surface features, wherein the first surface feature is resistant to forces acting along a first direction, wherein the second surface feature is resistant to forces acting along a second direction, wherein the first and second directions are non-parallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the mast/dowel). The first and second surface features may be intersecting planar surfaces which are side by side on a shelf of an anchoring element.

The anchoring elements 838, 840 may include one or more surface features that are resistant to side-to-side translation of the glenoid component 800, i.e., translation in the superior-inferior and/or anterior-posterior directions. A translation resistant surface feature may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature. The anchoring elements 838, 840 are illustrated with translation resistant surface features which are protruding shelves 858. The shelves 858 may protrude from the superior and/or inferior sides of each dowel 848 to increase the width of the dowel to resist translation. A total of twelve shelves 858 are shown, although any number may be present. The medial and lateral surfaces of the shelves 858 are parallel to the face 857 of the pedestal 856, so that the shelves 858 are oriented to resist axial pull-out, i.e., forces acting perpendicular to the back side of the glenoid component, or the face 857.

A slot 864, or groove or channel, may be present along the dowel, the exposed side 853 of the reinforcement plate 852, or both. In cemented applications of the technology, the bone cement may flow along the slot(s) 864 on the anchoring element.

The glenoid component 800 may be operatively implanted in a scapula 2 (not shown). The scapula 2 includes a glenoid fossa 4, a coracoid process 6, and an acromion process 8. The triangular shape of the anchoring elements 838, 840 matches the conical shape of the glenoid vault more closely than does a central peg or keel, in a superior-inferior view. The dowels 848 are peripherally arranged along the anterior portion 822 in the example shown. This places the pedestal 856 of the anchoring elements into regions of denser subchondral bone for stronger fixation. Medially in the glenoid vault, the side of the dowel 848 and the exposed side 853 of the reinforcement plate 852 may lie adjacent and parallel to the thick cortical walls of the glenoid vault.

Referring to FIGS. 2A-2H, a glenoid component 1000 includes a body 1002 with a lateral articular surface 1004 and an opposite medial bone-facing surface 1006.

A peripheral wall 1008 extends around the body 1002 between the surfaces 1004, 1006. A lateral peripheral edge 1010 extends around the body 1002 where the lateral articular surface 1004 intersects the peripheral wall 1008. The lateral peripheral edge 1010 may be rounded or relieved by a lateral peripheral relief 1012, such as a radius, fillet, chamfer, bevel, or the like. A medial peripheral edge 1014 extends around the body 1002 where the medial bone-facing surface 1006 intersects the peripheral wall 1008. The medial peripheral edge 1014 may be rounded or relieved by a medial peripheral relief 1016, such as a radius, fillet, chamfer, bevel, or the like.

The body 1002, lateral articular surface 1004, medial bone-facing surface 1006, peripheral wall 1008, lateral peripheral edge 1010, lateral peripheral relief 1012, medial peripheral edge 1014, and/or medial peripheral relief 1016 may be divided into a superior portion 1018, an inferior portion 1020, an anterior portion 1022, and a posterior portion 1024. The body 1002, lateral articular surface 1004, and/or medial bone-facing surface 1006 may also be divided into a peripheral portion near the peripheral wall 1008 and an interior or central portion. In examples other than shoulder glenoid components, where the surgical approach trajectory may be different than the approach described herein, the appropriate medical directional terms may be readily substituted by one of skill in the art.

The lateral articular surface 1004 may be concave as shown, planar, or convex in order to complement a natural or prosthetic humeral articular surface. The lateral articular surface 1004 may be spherical. The lateral articular surface 1004 may be elliptical or ovoid. The lateral articular surface 1004 may have a first radius 1026 which is dimensionally different from, i.e., larger or smaller than, a second radius 1028. The first radius 1026 may be a superior-inferior radius, or S-I radius. The second radius 1028 may be an anterior-posterior radius, or A-P radius.

The inferior portion 1020 of the body 1002 may include an inferior chamfer 1030 which extends between the lateral articular surface 1004 and the peripheral wall 1008. The inferior chamfer 1030 is a sloping surface, preferably a planar surface, that lowers the profile and thickness of the inferior portion 1020 along the lateral peripheral edge 1010.

The medial bone-facing surface 1006 may be convex as shown, planar, or concave.

The glenoid component 1000 includes at least one anchoring element 1038 which protrudes outwardly from the medial bone-facing surface 1006. The example shown includes a superior anchoring element 1038 and an inferior anchoring element 1040, although any number of anchoring elements may be present. Each anchoring element may be independently positioned on the medial bone-facing surface 1006, and may be independently sized.

Each anchoring element 1038, 1040 includes a dowel 1048, or mast, and a triangular reinforcement plate 1052, or sail or buttress.

The dowel 1048 projects from the medial bone-facing surface 1006 at an angle 1050 less than ninety degrees and greater than zero degrees. The angle 1050 may be referred to as a dowel angle or a mast angle. The angle 1050 may be measured between a central longitudinal axis 1049 of the dowel 1048 and a plane which is coplanar with the medial bone-facing surface 1006, if surface 1006 is planar, or a plane which is tangent to the medial bone-facing surface 1006, if surface 1006 is concave or convex. The plane may be tangent to the medial bone-facing surface 1006 at an intersection point between the central longitudinal axis 1049 of the dowel 1048 and the medial bone-facing surface 1006, or at a centroid of the medial bone-facing surface 1006. The dowel 1048 may project from the anterior portion 1022 of the body 1002, as shown, or from another portion of the body 1002. In the example shown, the dowels 1048 of anchoring elements 1038, 1040 project from peripheral locations in the anterior portion 1022 and terminate in medially located free ends. The dowel 1048 may have a round fundamental cross sectional shape, as shown, or another shape, such as a rectangle or dovetail. The dowel 1048 may include a hole 1070, which may receive a radiographic marker.

The reinforcement plate 1052 projects from the medial bone-facing surface 1006 in the acute angle 1050 between the dowel 1048 and the medial bone-facing surface 1006, and coplanar with the dowel 1048. An exposed side 1053 of the reinforcement plate 1052 projects from the medial bone-facing surface 1006 at an angle 1054 less than ninety degrees and greater than zero degrees. The angle 1054 may be referred to as a reinforcement angle. The angle 1054 opens toward the angle 1050, and the sum of angles 1050 and 1054 is greater than zero degrees and less than one hundred eighty degrees. The reinforcement plate 1052 intersects the dowel 1048 to form a triangular shape with one side formed by the medial bone-facing surface 1006, one side formed by the dowel 1048, and one side formed by the exposed side 1053 of the reinforcement plate 1052. The triangular shape may be an acute triangle having three internal angles each less than 90 degrees.

The anchoring elements 1038, 1040 may include a pedestal 1056 or footing where the anchoring element intersects the medial bone-facing surface 1006. The pedestal 1056 may be present on the dowel 1048 or the reinforcement plate 1052, or both. The pedestal 1056 may enlarge the anchoring element 1038, 1040 at the medial bone-facing surface 1006. The pedestal 1056 may terminate medially in a planar face 1057 which may establish the plane from which the angles 1050, 1054 are measured. The planar face 1057 may be tangent to the medial bone-facing surface 1006.

The anchoring elements 1038, 1040, including the dowels 1048, the reinforcement plates 1052, and the pedestals 1056, may project outwardly from the medial bone-facing surface 1006 orthogonally or at an acute angle when viewed from an anterior (i.e., FIG. 1E) or posterior (i.e., FIG. 1F) direction. The acute angle may be on either side of the anchoring element, i.e., on the superior or inferior side. For example, the acute angle may be on the superior side of the superior anchoring element 1038, and on the inferior side of the inferior anchoring element 1040, or vice versa.

The anchoring elements 1038, 1040 may include surface features to improve fixation, or pull-out strength, after implantation. Surface features may be present on one or more of the anchoring elements present on a glenoid component. The surface features may project outwardly or inwardly from the fundamental surface(s) of the anchoring elements 1038, 1040. The surface features may include notches, grooves, channels, ridges, accordion texture, barbs, threads, shelves, rings, ribs, or perforations. For example, alternating ridges 1060 and grooves 1062 are shown, as well as fenestrations 1068 extending through the anchoring elements 1038, 1040. The illustrated ridges 1060 and grooves 1062 are oriented to resist axial pull-out, i.e., forces acting perpendicular to the back side of the glenoid component, or the face 1057 described below. The illustrated fenestrations 1068 resist forces acting perpendicular to their central longitudinal axes. All of these surface features may facilitate bony ingrowth or bone cement interdigitation.

A particular surface feature may be oriented on an axis parallel to and offset from the corresponding axis of the fundamental surface of the corresponding anchoring element 1038 or 1040. For example, the dowel 1048 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 1038, 1040 to bend when inserted into the bone tunnel.

The anchoring elements 1038, 1040 may include at least two surface features, wherein the first surface feature is resistant to forces acting along a first direction, wherein the second surface feature is resistant to forces acting along a second direction, wherein the first and second directions are nonparallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the mast/dowel). The first and second surface features may be intersecting planar surfaces which are side by side on a shelf of an anchoring element.

The anchoring elements 1038, 1040 may include one or more surface features that are resistant to pullout forces acting along the central longitudinal axis 1049 of the dowel 1048. The anchoring element 1038 is illustrated with a surface feature which is a protruding planar surface 1072 which faces antero-laterally. The planar surface 1072 may protrude from the superior and/or inferior side of each dowel 1048 to increase the width of the dowel. One planar surface 1072 is shown protruding from the superior side of the dowel 1048 of the superior anchoring element 1038. The planar surface 1072 is perpendicular to the central longitudinal axis 1049 of the dowel 1048.

The anchoring elements 1038, 1040 may include one or more surface features that are resistant to pullout forces acting perpendicular to the central longitudinal axis 1049 of the dowel 1048. The anchoring element 1038 is illustrated with surface features which are protruding planar surfaces 1078. The planar surfaces 1078 may protrude from the anterior and/or posterior side of each dowel 1048 to increase the width of the dowel. Two planar surfaces 1078 are shown, with one planar surface 1078 facing antero-medially, and a second planar surface 1078 is shown facing postero-laterally, both on the superior anchoring element 1038. The planar surfaces 1078 are parallel to the central longitudinal axis 1049 of the dowel 1048.

The anchoring elements 1038, 1040 may include one or more surface features that are resistant to side-to-side translation of the glenoid component 1000, i.e., translation in the superior-inferior and/or anterior-posterior directions. A translation resistant surface feature may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature. The anchoring element 1038 is illustrated with a translation resistant surface feature which is a protruding dowel tip 1074, which is enlarged relative to the fundamental surface of the dowel 1048. The dowel tip 1074 may protrude from the superior, inferior, anterior, and/or posterior side of each dowel 1048, or intermediate positions such as superior-posterior, to increase the width of the dowel to resist translation. One dowel tip 1074 is shown protruding from the superior side of the dowel 1048 of the superior anchoring element 1038. The dowel tip 1074 terminates with the antero-laterally facing planar surface 1072, the antero-medially facing planar surface 1078, and the postero-laterally facing planar surface 1078. The interaction of the dowel tip 1074 and the bone tunnel mouth may cause the anchoring element 1038 to bend toward the anchoring element 1040 as the dowel tip 1074 is inserted in the bone tunnel.

A slot 1064, or groove or channel, may be present along the dowel, the exposed side 1053 of the reinforcement plate 1052, or both. In cemented applications of the technology, the bone cement may flow along the slot(s) 1064 on the anchoring element.

The glenoid component 1000 may be operatively implanted in a scapula 2 (not shown). The scapula 2 includes a glenoid fossa 4, a coracoid process 6, and an acromion process 8. The triangular shape of the anchoring elements 1038, 1040 matches the conical shape of the glenoid vault more closely than does a central peg or keel, in a superior-inferior view. The dowels 1048 are peripherally arranged along the anterior portion 1022 in the example shown. This places the pedestal 1056 of the anchoring elements into regions of denser subchondral bone for stronger fixation. Medially in the glenoid vault, the side of the dowel 1048 and the exposed side 1053 of the reinforcement plate 1052 may lie adjacent and parallel to the thick cortical walls of the glenoid vault.

Referring to FIGS. 3A-3H, a glenoid component 1100 includes a body 1102 with a lateral articular surface 1104 and an opposite medial bone-facing surface 1106.

A peripheral wall 1108 extends around the body 1102 between the surfaces 1104, 1106. A lateral peripheral edge 1110 extends around the body 1102 where the lateral articular surface 1104 intersects the peripheral wall 1108. The lateral peripheral edge 1110 may be rounded or relieved by a lateral peripheral relief 1112, such as a radius, fillet, chamfer, bevel, or the like. A medial peripheral edge 1114 extends around the body 1102 where the medial bone-facing surface 1106 intersects the peripheral wall 1108. The medial peripheral edge 1114 may be rounded or relieved by a medial peripheral relief 1116, such as a radius, fillet, chamfer, bevel, or the like.

The body 1102, lateral articular surface 1104, medial bone-facing surface 1106, peripheral wall 1108, lateral peripheral edge 1110, lateral peripheral relief 1112, medial peripheral edge 1114, and/or medial peripheral relief 1116 may be divided into a superior portion 1118, an inferior portion 1120, an anterior portion 1122, and a posterior portion 1124. The body 1102, lateral articular surface 1104, and/or medial bone-facing surface 1106 may also be divided into a peripheral portion near the peripheral wall 1108 and an interior or central portion. In examples other than shoulder glenoid components, where the surgical approach trajectory may be different than the approach described herein, the appropriate medical directional terms may be readily substituted by one of skill in the art.

The lateral articular surface 1104 may be concave as shown, planar, or convex in order to complement a natural or prosthetic humeral articular surface. The lateral articular surface 1104 may be spherical. The lateral articular surface 1104 may be elliptical or ovoid. The lateral articular surface 1104 may have a first radius 1126 which is dimensionally different from, i.e., larger or smaller than, a second radius 1128. The first radius 1126 may be a superior-inferior radius, or S-I radius. The second radius 1128 may be an anterior-posterior radius, or A-P radius.

The inferior portion 1120 of the body 1102 may include an inferior chamfer 1130 which extends between the lateral articular surface 1104 and the peripheral wall 1108. The inferior chamfer 1130 is a sloping surface, preferably a planar surface, that lowers the profile and thickness of the inferior portion 1120 along the lateral peripheral edge 1110.

The medial bone-facing surface 1106 may be convex as shown, planar, or concave.

The glenoid component 1100 includes at least one anchoring element 1138 which protrudes outwardly from the medial bone-facing surface 1106. The example shown includes a superior anchoring element 1138 and an inferior anchoring element 1140, although any number of anchoring elements may be present. Each anchoring element may be independently positioned on the medial bone-facing surface 1106, and may be independently sized.

Each anchoring element 1138, 1140 includes a dowel 1148, or mast, and a triangular reinforcement plate 1152, or sail or buttress.

The dowel 1148 projects from the medial bone-facing surface 1106 at an angle 1150 less than ninety degrees and greater than zero degrees. The angle 1150 may be referred to as a dowel angle or a mast angle. The angle 1150 may be measured between a central longitudinal axis 1149 of the dowel 1148 and a plane which is coplanar with the medial bone-facing surface 1106, if surface 1106 is planar, or a plane which is tangent to the medial bone-facing surface 1106, if surface 1106 is concave or convex. The plane may be tangent to the medial bone-facing surface 1106 at an intersection point between the central longitudinal axis 1149 of the dowel 1148 and the medial bone-facing surface 1106, or at a centroid of the medial bone-facing surface 1106. The dowel 1148 may project from the anterior portion 1122 of the body 1102, as shown, or from another portion of the body 1102. In the example shown, the dowels 1148 of anchoring elements 1138, 1140 project from peripheral locations in the anterior portion 1122 and terminate in medially located free ends. The dowel 1148 may have a round fundamental cross sectional shape, as shown, or another shape, such as a rectangle or dovetail. The dowel 1148 may include a hole 1170, which may receive a radiographic marker.

The reinforcement plate 1152 projects from the medial bone-facing surface 1106 in the acute angle 1150 between the dowel 1148 and the medial bone-facing surface 1106, and coplanar with the dowel 1148. An exposed side 1153 of the reinforcement plate 1152 projects from the medial bone-facing surface 1106 at an angle 1154 less than ninety degrees and greater than zero degrees. The angle 1154 may be referred to as a reinforcement angle. The angle 1154 opens toward the angle 1150, and the sum of angles 1150 and 1154 is greater than zero degrees and less than one hundred eighty degrees. The reinforcement plate 1152 intersects the dowel 1148 to form a triangular shape with one side formed by the medial bone-facing surface 1106, one side formed by the dowel 1148, and one side formed by the exposed side 1153 of the reinforcement plate 1152. The triangular shape may be an acute triangle having three internal angles each less than 90 degrees.

The anchoring elements 1138, 1140 may include a pedestal 1156 or footing where the anchoring element intersects the medial bone-facing surface 1106. The pedestal 1156 may be present on the dowel 1148 or the reinforcement plate 1152, or both. The pedestal 1156 may enlarge the anchoring element 1138, 1140 at the medial bone-facing surface 1106. The pedestal 1156 may terminate medially in a planar face 1157 which may establish the plane from which the angles 1150, 1154 are measured. The planar face 1157 may be tangent to the medial bone-facing surface 1106.

The anchoring elements 1138, 1140, including the dowels 1148, the reinforcement plates 1152, and the pedestals 1156, may project outwardly from the medial bone-facing surface 1106 orthogonally or at an acute angle when viewed from an anterior (i.e., FIG. 1E) or posterior (i.e., FIG. 1F) direction. The acute angle may be on either side of the anchoring element, i.e., on the superior or inferior side. For example, the acute angle may be on the superior side of the superior anchoring element 1138, and on the inferior side of the inferior anchoring element 1140, or vice versa.

The anchoring elements 1138, 1140 may include surface features to improve fixation, or pull-out strength, after implantation. Surface features may be present on one or more of the anchoring elements present on a glenoid component. The surface features may project outwardly or inwardly from the fundamental surface(s) of the anchoring elements 1138, 1140. The surface features may include notches, grooves, channels, ridges, accordion texture, barbs, threads, shelves, rings, ribs, or perforations. For example, alternating ridges 1160 and grooves 1162 are shown, as well as fenestrations 1168 extending through the anchoring elements 1138, 1140. The illustrated ridges 1160 and grooves 1162 are oriented to resist axial pull-out, i.e., forces acting perpendicular to the back side of the glenoid component, or the face 1157 described below. The illustrated fenestrations 1168 resist forces acting perpendicular to their central longitudinal axes. All of these surface features may facilitate bony ingrowth or bone cement interdigitation.

A particular surface feature may be oriented on an axis parallel to and offset from the corresponding axis of the fundamental surface of the corresponding anchoring element 1138 or 1140. For example, the dowel 1148 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 1138, 1140 to bend when inserted into the bone tunnel.

The anchoring elements 1138, 1140 may include at least two surface features, wherein the first surface feature is resistant to forces acting along a first direction, wherein the second surface feature is resistant to forces acting along a second direction, wherein the first and second directions are nonparallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the mast/dowel). The first and second surface features may be intersecting planar surfaces which are side by side on a shelf of an anchoring element.

The anchoring elements 1138, 1140 may include one or more surface features that are resistant to pullout forces acting along the central longitudinal axis 1149 of the dowel 1148. The anchoring element 1138 is illustrated with a surface feature which is a protruding planar surface 1172 which faces antero-laterally. The planar surface 1172 may protrude from the superior and/or inferior side of each dowel 1148 to increase the width of the dowel. One planar surface 1172 is shown protruding from the superior-posterior side of the dowel 1148 of the superior anchoring element 1138. The planar surface 1172 is perpendicular to the central longitudinal axis 1149 of the dowel 1148.

The anchoring elements 1138, 1140 may include one or more surface features that are resistant to pullout forces acting perpendicular to the central longitudinal axis 1149 of the dowel 1148. The anchoring element 1138 is illustrated with surface features which are protruding planar surfaces 1178. The planar surfaces 1178 may protrude from the anterior and/or posterior side of each dowel 1148 to increase the width of the dowel. Two planar surfaces 1178 are shown, with one planar surface 1178 facing antero-medially, and a second planar surface 1178 is shown facing postero-laterally, both on the superior anchoring element 1138. The planar surfaces 1178 are parallel to the central longitudinal axis 1149 of the dowel 1148.

The anchoring elements 1138, 1140 may include one or more surface features that are resistant to side-to-side translation of the glenoid component 1100, i.e., translation in the superior-inferior and/or anterior-posterior directions. A translation resistant surface feature may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature. The anchoring element 1138 is illustrated with a translation resistant surface feature which is a protruding dowel tip 1174, which is enlarged relative to the fundamental surface of the dowel 1148. The dowel tip 1174 may protrude from the superior and/or inferior side of each dowel 1148 to increase the width of the dowel to resist translation. One dowel tip 1174 is shown protruding from the superior-posterior side of the dowel 1148 of the superior anchoring element 1138. The dowel tip 1174 terminates with the antero-laterally facing planar surface 1172, the antero-medially facing planar surface 1178, and the postero-laterally facing planar surface 1178. The interaction of the dowel tip 1174 and the bone tunnel mouth may cause the anchoring element 1138 to bend toward the anchoring element 1140 as the dowel tip 1174 is inserted in the bone tunnel.

A slot 1164, or groove or channel, may be present along the dowel, the exposed side 1153 of the reinforcement plate 1152, or both. In cemented applications of the technology, the bone cement may flow along the slot(s) 1164 on the anchoring element.

The glenoid component 1100 may be operatively implanted in a scapula 2 (not shown). The scapula 2 includes a glenoid fossa 4, a coracoid process 6, and an acromion process 8. The triangular shape of the anchoring elements 1138, 1140 matches the conical shape of the glenoid vault more closely than does a central peg or keel, in a superior-inferior view. The dowels 1148 are peripherally arranged along the anterior portion 1122 in the example shown. This places the pedestal 1156 of the anchoring elements into regions of denser subchondral bone for stronger fixation. Medially in the glenoid vault, the side of the dowel 1148 and the exposed side 1153 of the reinforcement plate 1152 may lie adjacent and parallel to the thick cortical walls of the glenoid vault.

Referring to FIGS. 4A-4H, a glenoid component 2500 includes a body 2502 with a lateral articular surface 2504 and an opposite medial bone-facing surface 2506.

A peripheral wall 2508 extends around the body 2502 between the surfaces 2504, 2506. A lateral peripheral edge 2510 extends around the body 2502 where the lateral articular surface 2504 intersects the peripheral wall 2508. The lateral peripheral edge 2510 may be rounded or relieved by a lateral peripheral relief 2512, such as a radius, fillet, chamfer, bevel, or the like. A medial peripheral edge 2514 extends around the body 2502 where the medial bone-facing surface 2506 intersects the peripheral wall 2508. The medial peripheral edge 2514 may be rounded or relieved by a medial peripheral relief 2516, such as a radius, fillet, chamfer, bevel, or the like.

The body 2502, lateral articular surface 2504, medial bone-facing surface 2506, peripheral wall 2508, lateral peripheral edge 2510, lateral peripheral relief 2512, medial peripheral edge 2514, and/or medial peripheral relief 2516 may be divided into a superior portion 2518, an inferior portion 2520, an anterior portion 2522, and a posterior portion 2524. The body 2502, lateral articular surface 2504, and/or medial bone-facing surface 2506 may also be divided into a peripheral portion near the peripheral wall 2508 and an interior or central portion. In examples other than shoulder glenoid components, where the surgical approach trajectory may be different than the approach described herein, the appropriate medical directional terms may be readily substituted by one of skill in the art.

The lateral articular surface 2504 may be concave as shown, planar, or convex in order to complement a natural or prosthetic humeral articular surface. The lateral articular surface 2504 may be spherical. The lateral articular surface 2504 may be elliptical or ovoid. The lateral articular surface 2504 may have a first radius 2526 which is dimensionally different from, i.e., larger or smaller than, a second radius 2528. The first radius 2526 may be a superior-inferior radius, or S-I radius. The second radius 2528 may be an anterior-posterior radius, or A-P radius.

The inferior portion 2520 of the body 2502 may include an inferior chamfer 2530 which extends between the lateral articular surface 2504 and the peripheral wall 2508. The inferior chamfer 2530 is a sloping surface, preferably a planar surface, that lowers the profile and thickness of the inferior portion 2520 along the lateral peripheral edge 2510.

The medial bone-facing surface 2506 may be convex as shown, planar, or concave.

The glenoid component 2500 includes at least one anchoring element 2538 which protrudes outwardly from the medial bone-facing surface 2506. The example shown includes a superior anchoring element 2538 and an inferior anchoring element 2540, although any number of anchoring elements may be present. Each anchoring element may be independently positioned on the medial bone-facing surface 2506, and may be independently sized.

Each anchoring element 2538, 2540 includes a dowel 2548, or mast, and a triangular reinforcement plate 2552, or sail or buttress.

The dowel 2548 projects from the medial bone-facing surface 2506 at an angle 2550 less than ninety degrees and greater than zero degrees. The angle 2550 may be referred to as a dowel angle or a mast angle. The angle 2550 may be measured between a central longitudinal axis 2549 of the dowel 2548 and a plane which is coplanar with the medial bone-facing surface 2506, if surface 2506 is planar, or a plane which is tangent to the medial bone-facing surface 2506, if surface 2506 is concave or convex. The plane may be tangent to the medial bone-facing surface 2506 at an intersection point between the central longitudinal axis 2549 of the dowel 2548 and the medial bone-facing surface 2506, or at a centroid of the medial bone-facing surface 2506. The dowel 2548 may project from the anterior portion 2522 of the body 2502, as shown, or from another portion of the body 2502. In the example shown, the dowels 2548 of anchoring elements 2538, 2540 project from peripheral locations in the anterior portion 2522 and terminate in medially located free ends. The dowel 2548 may have a round fundamental cross sectional shape, as shown, or another shape, such as a rectangle or dovetail. The dowel 2548 may include a hole 2570, which may receive a radiographic marker.

The reinforcement plate 2552 projects from the medial bone-facing surface 2506 in the acute angle 2550 between the dowel 2548 and the medial bone-facing surface 2506, and coplanar with the dowel 2548. An exposed side 2553 of the reinforcement plate 2552 projects from the medial bone-facing surface 2506 at an angle 2554 less than ninety degrees and greater than zero degrees. The angle 2554 may be referred to as a reinforcement angle. The angle 2554 opens toward the angle 2550, and the sum of angles 2550 and 2554 is greater than zero degrees and less than one hundred eighty degrees. The reinforcement plate 2552 intersects the dowel 2548 to form a triangular shape with one side formed by the medial bone-facing surface 2506, one side formed by the dowel 2548, and one side formed by the exposed side 2553 of the reinforcement plate 2552. The triangular shape may be an acute triangle having three internal angles each less than 90 degrees.

The anchoring elements 2538, 2540 may include a pedestal 2556 or footing where the anchoring element intersects the medial bone-facing surface 2506. The pedestal 2556 may be present on the dowel 2548 or the reinforcement plate 2552, or both. The pedestal 2556 may enlarge the anchoring element 2538, 2540 at the medial bone-facing surface 2506. The pedestal 2556 may terminate medially in a planar face 2557 which may establish the plane from which the angles 2550, 2554 are measured. The planar face 2557 may be tangent to the medial bone-facing surface 2506.

The anchoring elements 2538, 2540, including the dowels 2548, the reinforcement plates 2552, and the pedestals 2556, may project outwardly from the medial bone-facing surface 2506 orthogonally or at an acute angle when viewed from an anterior (i.e., FIG. 1E) or posterior (i.e., FIG. 1F) direction. The acute angle may be on either side of the anchoring element, i.e., on the superior or inferior side. For example, the acute angle may be on the superior side of the superior anchoring element 2538, and on the inferior side of the inferior anchoring element 2540, or vice versa.

The anchoring elements 2538, 2540 may include surface features to improve fixation, or pull-out strength, after implantation. Surface features may be present on one or more of the anchoring elements present on a glenoid component. The surface features may project outwardly or inwardly from the fundamental surface(s) of the anchoring elements 2538, 2540. The surface features may include notches, grooves, channels, ridges, accordion texture, barbs, threads, shelves, rings, ribs, or perforations. For example, alternating ridges 2560 and grooves 2562 are shown, as well as fenestrations 2568 extending through the anchoring elements 2538, 2540. The illustrated ridges 2560 and grooves 2562 are oriented to resist axial pull-out, i.e., forces acting perpendicular to the back side of the glenoid component, or the face 2557 described below. The illustrated fenestrations 2568 resist forces acting perpendicular to their central longitudinal axes. All of these surface features may facilitate bony ingrowth or bone cement interdigitation.

A particular surface feature may be oriented on an axis parallel to and offset from the corresponding axis of the fundamental surface of the corresponding anchoring element 2538 or 2540. For example, the dowel 2548 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 2538, 2540 to bend when inserted into the bone tunnel.

The anchoring elements 2538, 2540 may include at least two surface features, wherein the first surface feature is resistant to forces acting along a first direction, wherein the second surface feature is resistant to forces acting along a second direction, wherein the first and second directions are nonparallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the mast/dowel). The first and second surface features may be intersecting planar surfaces which are side by side on a shelf of an anchoring element.

The anchoring elements 2538, 2540 may include one or more surface features that are resistant to axial pull-out, i.e., forces acting perpendicular to the back side of the glenoid component, or the face 2557. The anchoring element 2538 is illustrated with a surface feature which is a protruding planar surface 2572 which faces laterally. The planar surface 2572 may protrude from the superior and/or inferior side of each dowel 2548 to increase the width of the dowel. One planar surface 2572 is shown protruding from the superior-posterior side of the dowel 2548 of the superior anchoring element 2538. The planar surface 2572 is parallel to the face 2557 of the pedestal 2556.

The anchoring elements 2538, 2540 may include one or more surface features that are resistant to pullout forces acting perpendicular to the central longitudinal axis 2549 of the dowel 2548. The anchoring element 2538 is illustrated with surface features which are protruding planar surfaces 2578. The planar surfaces 2578 may protrude from the anterior and/or posterior side of each dowel 2548 to increase the width of the dowel. Two planar surfaces 2578 are shown, with one planar surface 2578 facing antero-medially, and a second planar surface 2578 is shown facing postero-laterally, both on the superior anchoring element 2538. The planar surfaces 2578 are parallel to the central longitudinal axis 2549 of the dowel 2548.

The anchoring elements 2538, 2540 may include one or more surface features that are resistant to side-to-side translation of the glenoid component 2500, i.e., translation in the superior-inferior and/or anterior-posterior directions. A translation resistant surface feature may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature. The anchoring element 2538 is illustrated with a translation resistant surface feature which is a protruding dowel tip 2574, which is enlarged relative to the fundamental surface of the dowel 2548. The dowel tip 2574 may protrude from the superior and/or inferior side of each dowel 2548 to increase the width of the dowel to resist translation. One dowel tip 2574 is shown protruding from the superior-posterior side of the dowel 2548 of the superior anchoring element 2538. The dowel tip 2574 terminates with the antero-laterally facing planar surface 2572, the antero-medially facing planar surface 2578, and the postero-laterally facing planar surface 2578. The interaction of the dowel tip 2574 and the bone tunnel mouth may cause the anchoring element 2538 to bend toward the anchoring element 2540 as the dowel tip 2574 is inserted in the bone tunnel.

A slot 2564, or groove or channel, may be present along the dowel, the exposed side 2553 of the reinforcement plate 2552, or both. In cemented applications of the technology, the bone cement may flow along the slot(s) 2564 on the anchoring element.

The glenoid component 2500 may be operatively implanted in a scapula 2 (not shown). The scapula 2 includes a glenoid fossa 4, a coracoid process 6, and an acromion process 8. The triangular shape of the anchoring elements 2538, 2540 matches the conical shape of the glenoid vault more closely than does a central peg or keel, in a superior-inferior view. The dowels 2548 are peripherally arranged along the anterior portion 2522 in the example shown. This places the pedestal 2556 of the anchoring elements into regions of denser subchondral bone for stronger fixation. Medially in the glenoid vault, the side of the dowel 2548 and the exposed side 2553 of the reinforcement plate 2552 may lie adjacent and parallel to the thick cortical walls of the glenoid vault.

Referring to FIGS. 5A-5H, a glenoid component 2700 includes a body 2702 with a lateral articular surface 2704 and an opposite medial bone-facing surface 2706.

A peripheral wall 2708 extends around the body 2702 between the surfaces 2704, 2706. A lateral peripheral edge 2710 extends around the body 2702 where the lateral articular surface 2704 intersects the peripheral wall 2708. The lateral peripheral edge 2710 may be rounded or relieved by a lateral peripheral relief 2712, such as a radius, fillet, chamfer, bevel, or the like. A medial peripheral edge 2714 extends around the body 2702 where the medial bone-facing surface 2706 intersects the peripheral wall 2708. The medial peripheral edge 2714 may be rounded or relieved by a medial peripheral relief 2716, such as a radius, fillet, chamfer, bevel, or the like.

The body 2702, lateral articular surface 2704, medial bone-facing surface 2706, peripheral wall 2708, lateral peripheral edge 2710, lateral peripheral relief 2712, medial peripheral edge 2714, and/or medial peripheral relief 2716 may be divided into a superior portion 2718, an inferior portion 2720, an anterior portion 2722, and a posterior portion 2724. The body 2702, lateral articular surface 2704, and/or medial bone-facing surface 2706 may also be divided into a peripheral portion near the peripheral wall 2708 and an interior or central portion. In examples other than shoulder glenoid components, where the surgical approach trajectory may be different than the approach described herein, the appropriate medical directional terms may be readily substituted by one of skill in the art.

The lateral articular surface 2704 may be concave as shown, planar, or convex in order to complement a natural or prosthetic humeral articular surface. The lateral articular surface 2704 may be spherical. The lateral articular surface 2704 may be elliptical or ovoid. The lateral articular surface 2704 may have a first radius 2726 which is dimensionally different from, i.e., larger or smaller than, a second radius 2728. The first radius 2726 may be a superior-inferior radius, or S-I radius. The second radius 2728 may be an anterior-posterior radius, or A-P radius.

The inferior portion 2720 of the body 2702 may include an inferior chamfer 2730 which extends between the lateral articular surface 2704 and the peripheral wall 2708. The inferior chamfer 2730 is a sloping surface, preferably a planar surface, that lowers the profile and thickness of the inferior portion 2720 along the lateral peripheral edge 2710.

The medial bone-facing surface 2706 may be convex as shown, planar, or concave.

The glenoid component 2700 includes at least one anchoring element 2738 which protrudes outwardly from the medial bone-facing surface 2706. The example shown includes a superior anchoring element 2738 and an inferior anchoring element 2740, although any number of anchoring elements may be present. Each anchoring element may be independently positioned on the medial bone-facing surface 2706, and may be independently sized.

Each anchoring element 2738, 2740 includes a dowel 2748, or mast, and a triangular reinforcement plate 2752, or sail or buttress.

The dowel 2748 projects from the medial bone-facing surface 2706 at an angle 2750 less than ninety degrees and greater than zero degrees. The angle 2750 may be referred to as a dowel angle or a mast angle. The angle 2750 may be measured between a central longitudinal axis 2749 of the dowel 2748 and a plane which is coplanar with the medial bone-facing surface 2706, if surface 2706 is planar, or a plane which is tangent to the medial bone-facing surface 2706, if surface 2706 is concave or convex. The plane may be tangent to the medial bone-facing surface 2706 at an intersection point between the central longitudinal axis 2749 of the dowel 2748 and the medial bone-facing surface 2706, or at a centroid of the medial bone-facing surface 2706. The dowel 2748 may project from the anterior portion 2722 of the body 2702, as shown, or from another portion of the body 2702. In the example shown, the dowels 2748 of anchoring elements 2738, 2740 project from peripheral locations in the anterior portion 2722 and terminate in medially located free ends. The dowel 2748 may have a round fundamental cross sectional shape, as shown, or another shape, such as a rectangle or dovetail. The dowel 2748 may include a hole 2770, which may receive a radiographic marker.

The reinforcement plate 2752 projects from the medial bone-facing surface 2706 in the acute angle 2750 between the dowel 2748 and the medial bone-facing surface 2706, and coplanar with the dowel 2748. An exposed side 2753 of the reinforcement plate 2752 projects from the medial bone-facing surface 2706 at an angle 2754 less than ninety degrees and greater than zero degrees. The angle 2754 may be referred to as a reinforcement angle. The angle 2754 opens toward the angle 2750, and the sum of angles 2750 and 2754 is greater than zero degrees and less than one hundred eighty degrees. The reinforcement plate 2752 intersects the dowel 2748 to form a triangular shape with one side formed by the medial bone-facing surface 2706, one side formed by the dowel 2748, and one side formed by the exposed side 2753 of the reinforcement plate 2752. The triangular shape may be an acute triangle having three internal angles each less than 90 degrees.

The anchoring elements 2738, 2740 may include a pedestal 2756 or footing where the anchoring element intersects the medial bone-facing surface 2706. The pedestal 2756 may be present on the dowel 2748 or the reinforcement plate 2752, or both. The pedestal 2756 may enlarge the anchoring element 2738, 2740 at the medial bone-facing surface 2706. The pedestal 2756 may terminate medially in a planar face 2757 which may establish the plane from which the angles 2750, 2754 are measured. The planar face 2757 may be tangent to the medial bone-facing surface 2706.

The anchoring elements 2738, 2740, including the dowels 2748, the reinforcement plates 2752, and the pedestals 2756, may project outwardly from the medial bone-facing surface 2706 orthogonally or at an acute angle when viewed from an anterior (i.e., FIG. 1E) or posterior (i.e., FIG. 1F) direction. The acute angle may be on either side of the anchoring element, i.e., on the superior or inferior side. For example, the acute angle may be on the superior side of the superior anchoring element 2738, and on the inferior side of the inferior anchoring element 2740, or vice versa.

The anchoring elements 2738, 2740 may include surface features to improve fixation, or pull-out strength, after implantation. Surface features may be present on one or more of the anchoring elements present on a glenoid component. The surface features may project outwardly or inwardly from the fundamental surface(s) of the anchoring elements 2738, 2740. The surface features may include notches, grooves, channels, ridges, accordion texture, barbs, threads, shelves, rings, ribs, or perforations. For example, alternating ridges 2760 and grooves 2762 are shown, as well as fenestrations 2768 extending through the anchoring elements 2738, 2740. The illustrated ridges 2760 and grooves 2762 are oriented to resist axial pull-out, i.e., forces acting perpendicular to the back side of the glenoid component, or the face 2757 described below. The illustrated fenestrations 2768 resist forces acting perpendicular to their central longitudinal axes. All of these surface features may facilitate bony ingrowth or bone cement interdigitation.

A particular surface feature may be oriented on an axis parallel to and offset from the corresponding axis of the fundamental surface of the corresponding anchoring element 2738 or 2740. For example, the dowel 2748 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 2738, 2740 to bend when inserted into the bone tunnel.

The anchoring elements 2738, 2740 may include at least two surface features, wherein the first surface feature is resistant to forces acting along a first direction, wherein the second surface feature is resistant to forces acting along a second direction, wherein the first and second directions are nonparallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the mast/dowel). The first and second surface features may be intersecting planar surfaces which are side by side on a shelf of an anchoring element.

The anchoring elements 2738, 2740 may include one or more surface features that are resistant to axial pull-out, i.e., forces acting perpendicular to the back side of the glenoid component, or the face 2757. The anchoring elements 2738, 2740 are illustrated with surface features which are protruding planar surfaces 2772 which face laterally. The planar surfaces 2772 may protrude from the superior and/or inferior side of each dowel 2748 to increase the width of the dowel. One planar surface 2772 is shown protruding from the superior-posterior side of the dowel 2748 of the superior anchoring element 2738 and a second planar surface 2772 is shown protruding from the inferior-posterior side of the dowel 2748 of the inferior anchoring element 2740. The planar surfaces 2772 are parallel to the face 2757 of the pedestal 2756.

The anchoring elements 2738, 2740 may include one or more surface features that are resistant to pullout forces acting perpendicular to the central longitudinal axis 2749 of the dowel 2748. The anchoring elements 2738, 2740 are illustrated with surface features which are protruding planar surfaces 2778. The planar surfaces 2778 may protrude from the anterior and/or posterior side of each dowel 2748 to increase the width of the dowel. Two planar surfaces 2778 are shown, with one planar surface 2778 facing postero-lateral-inferior on the superior anchoring element 2738, and a second planar surface 2778 is shown facing postero-lateral-superior, on the inferior anchoring element 2740. The planar surfaces 2778 are parallel to the central longitudinal axis 2749 of the dowel 2748.

The anchoring elements 2738, 2740 may include one or more surface features that are resistant to side-to-side translation of the glenoid component 2700, i.e., translation in the superior-inferior and/or anterior-posterior directions. A translation resistant surface feature may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature. The anchoring element 2738 is illustrated with a translation resistant surface feature which is a protruding dowel tip 2774, which is enlarged relative to the fundamental surface of the dowel 2748. The dowel tip 2774 may protrude from the superior and/or inferior side of each dowel 2748 to increase the width of the dowel to resist translation. One dowel tip 2774 is shown protruding from the superior-posterior side of the dowel 2748 of the superior anchoring element 2738, and a second dowel tip 2774 is shown protruding from the inferior-posterior side of the dowel 2748 of the inferior anchoring element 2740. The dowel tip 2774 terminates with the antero-laterally facing planar surface 2772, and the postero-lateral-inferior facing planar surface 2778 or the postero-lateral-superior facing planar surface 2778. The interaction of the dowel tip 2774 and the bone tunnel mouth may cause the anchoring element 2738 to bend toward the anchoring element 2740 as the dowel tip 2774 is inserted in the bone tunnel.

A slot 2764, or groove or channel, may be present along the dowel, the exposed side 2753 of the reinforcement plate 2752, or both. In cemented applications of the technology, the bone cement may flow along the slot(s) 2764 on the anchoring element.

The glenoid component 2700 may be operatively implanted in a scapula 2 (not shown). The scapula 2 includes a glenoid fossa 4, a coracoid process 6, and an acromion process 8. The triangular shape of the anchoring elements 2738, 2740 matches the conical shape of the glenoid vault more closely than does a central peg or keel, in a superior-inferior view. The dowels 2748 are peripherally arranged along the anterior portion 2722 in the example shown. This places the pedestal 2756 of the anchoring elements into regions of denser subchondral bone for stronger fixation. Medially in the glenoid vault, the side of the dowel 2748 and the exposed side 2753 of the reinforcement plate 2752 may lie adjacent and parallel to the thick cortical walls of the glenoid vault.

Referring to FIGS. 6A-6H, a glenoid component 2800 includes a body 2802 with a lateral articular surface 2804 and an opposite medial bone-facing surface 2806.

A peripheral wall 2808 extends around the body 2802 between the surfaces 2804, 2806. A lateral peripheral edge 2810 extends around the body 2802 where the lateral articular surface 2804 intersects the peripheral wall 2808. The lateral peripheral edge 2810 may be rounded or relieved by a lateral peripheral relief 2812, such as a radius, fillet, chamfer, bevel, or the like. A medial peripheral edge 2814 extends around the body 2802 where the medial bone-facing surface 2806 intersects the peripheral wall 2808. The medial peripheral edge 2814 may be rounded or relieved by a medial peripheral relief 2816, such as a radius, fillet, chamfer, bevel, or the like.

The body 2802, lateral articular surface 2804, medial bone-facing surface 2806, peripheral wall 2808, lateral peripheral edge 2810, lateral peripheral relief 2812, medial peripheral edge 2814, and/or medial peripheral relief 2816 may be divided into a superior portion 2818, an inferior portion 2820, an anterior portion 2822, and a posterior portion 2824. The body 2802, lateral articular surface 2804, and/or medial bone-facing surface 2806 may also be divided into a peripheral portion near the peripheral wall 2808 and an interior or central portion. In examples other than shoulder glenoid components, where the surgical approach trajectory may be different than the approach described herein, the appropriate medical directional terms may be readily substituted by one of skill in the art.

The lateral articular surface 2804 may be concave as shown, planar, or convex in order to complement a natural or prosthetic humeral articular surface. The lateral articular surface 2804 may be spherical. The lateral articular surface 2804 may be elliptical or ovoid. The lateral articular surface 2804 may have a first radius 2826 which is dimensionally different from, i.e., larger or smaller than, a second radius 2828. The first radius 2826 may be a superior-inferior radius, or S-I radius. The second radius 2828 may be an anterior-posterior radius, or A-P radius.

The inferior portion 2820 of the body 2802 may include an inferior chamfer 2830 which extends between the lateral articular surface 2804 and the peripheral wall 2808. The inferior chamfer 2830 is a sloping surface, preferably a planar surface, that lowers the profile and thickness of the inferior portion 2820 along the lateral peripheral edge 2810.

The medial bone-facing surface 2806 may be convex as shown, planar, or concave.

The glenoid component 2800 includes at least one anchoring element 2838 which protrudes outwardly from the medial bone-facing surface 2806. The example shown includes a superior anchoring element 2838 and an inferior anchoring element 2840, although any number of anchoring elements may be present. Each anchoring element may be independently positioned on the medial bone-facing surface 2806, and may be independently sized.

Each anchoring element 2838, 2840 includes a dowel 2848, or mast, and a triangular reinforcement plate 2852, or sail or buttress.

The dowel 2848 projects from the medial bone-facing surface 2806 at an angle 2850 less than ninety degrees and greater than zero degrees. The angle 2850 may be referred to as a dowel angle or a mast angle. The angle 2850 may be measured between a central longitudinal axis 2849 of the dowel 2848 and a plane which is coplanar with the medial bone-facing surface 2806, if surface 2806 is planar, or a plane which is tangent to the medial bone-facing surface 2806, if surface 2806 is concave or convex. The plane may be tangent to the medial bone-facing surface 2806 at an intersection point between the central longitudinal axis 2849 of the dowel 2848 and the medial bone-facing surface 2806, or at a centroid of the medial bone-facing surface 2806. The dowel 2848 may project from the anterior portion 2822 of the body 2802, as shown, or from another portion of the body 2802. In the example shown, the dowels 2848 of anchoring elements 2838, 2840 project from peripheral locations in the anterior portion 2822 and terminate in medially located free ends. The dowel 2848 may have a round fundamental cross sectional shape, as shown, or another shape, such as a rectangle or dovetail. The dowel 2848 may include a hole 2870, which may receive a radiographic marker.

The reinforcement plate 2852 projects from the medial bone-facing surface 2806 in the acute angle 2850 between the dowel 2848 and the medial bone-facing surface 2806, and coplanar with the dowel 2848. An exposed side 2853 of the reinforcement plate 2852 projects from the medial bone-facing surface 2806 at an angle 2854 less than ninety degrees and greater than zero degrees. The angle 2854 may be referred to as a reinforcement angle. The angle 2854 opens toward the angle 2850, and the sum of angles 2850 and 2854 is greater than zero degrees and less than one hundred eighty degrees. The reinforcement plate 2852 intersects the dowel 2848 to form a triangular shape with one side formed by the medial bone-facing surface 2806, one side formed by the dowel 2848, and one side formed by the exposed side 2853 of the reinforcement plate 2852. The triangular shape may be an acute triangle having three internal angles each less than 90 degrees.

The anchoring elements 2838, 2840 may include a pedestal 2856 or footing where the anchoring element intersects the medial bone-facing surface 2806. The pedestal 2856 may be present on the dowel 2848 or the reinforcement plate 2852, or both. The pedestal 2856 may enlarge the anchoring element 2838, 2840 at the medial bone-facing surface 2806. The pedestal 2856 may terminate medially in a planar face 2857 which may establish the plane from which the angles 2850, 2854 are measured. The planar face 2857 may be tangent to the medial bone-facing surface 2806.

The anchoring elements 2838, 2840, including the dowels 2848, the reinforcement plates 2852, and the pedestals 2856, may project outwardly from the medial bone-facing surface 2806 orthogonally or at an acute angle when viewed from an anterior (i.e., FIG. 1E) or posterior (i.e., FIG. 1F) direction. The acute angle may be on either side of the anchoring element, i.e., on the superior or inferior side. For example, the acute angle may be on the superior side of the superior anchoring element 2838, and on the inferior side of the inferior anchoring element 2840, or vice versa.

The anchoring elements 2838, 2840 may include surface features to improve fixation, or pull-out strength, after implantation. Surface features may be present on one or more of the anchoring elements present on a glenoid component. The surface features may project outwardly or inwardly from the fundamental surface(s) of the anchoring elements 2838, 2840. The surface features may include notches, grooves, channels, ridges, accordion texture, barbs, threads, shelves, rings, ribs, or perforations. For example, alternating ridges 2860 and grooves 2862 are shown, as well as fenestrations 2868 extending through the anchoring elements 2838, 2840. The illustrated ridges 2860 and grooves 2862 are oriented to resist axial pull-out, i.e., forces acting perpendicular to the back side of the glenoid component, or the face 2857 described below. The illustrated fenestrations 2868 resist forces acting perpendicular to their central longitudinal axes. All of these surface features may facilitate bony ingrowth or bone cement interdigitation.

A particular surface feature may be oriented on an axis parallel to and offset from the corresponding axis of the fundamental surface of the corresponding anchoring element 2838 or 2840. For example, the dowel 2848 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 2838, 2840 to bend when inserted into the bone tunnel.

The anchoring elements 2838, 2840 may include at least two surface features, wherein the first surface feature is resistant to forces acting along a first direction, wherein the second surface feature is resistant to forces acting along a second direction, wherein the first and second directions are nonparallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the mast/dowel). The first and second surface features may be intersecting planar surfaces which are side by side on a shelf of an anchoring element.

The anchoring elements 2838, 2840 may include one or more surface features that are resistant to pullout forces acting along the central longitudinal axis 2849 of the dowel 2848. The anchoring elements 2838, 2840 are illustrated with surface features which are protruding planar surfaces 2872 which face antero-laterally. The planar surfaces 2872 may protrude from the superior and/or inferior sides of each dowel 2848 to increase the width of the dowel. Two planar surfaces 2872 are shown, with a first planar surface 2872 protruding from the superior-posterior side of the dowel 2848 of the superior anchoring element 2838, and a second planar surface 2872 protruding from the inferior-posterior side of the dowel 2848 of the inferior anchoring element 2840. The planar surfaces 2872 are perpendicular to the central longitudinal axis 2849 of the dowel 2848.

The anchoring elements 2838, 2840 may include one or more surface features that are resistant to pullout forces acting perpendicular to the central longitudinal axis 2849 of the dowel 2848. The anchoring elements 2838, 2840 are illustrated with surface features which are protruding planar surfaces 2878. The planar surfaces 2878 may protrude from the anterior and/or posterior side of each dowel 2848 to increase the width of the dowel. Two planar surfaces 2878 are shown, with one planar surface 2878 facing postero-lateral-inferior on the superior anchoring element 2838, and a second planar surface 2878 is shown facing postero-lateral-superior, on the inferior anchoring element 2840. The planar surfaces 2878 are parallel to the central longitudinal axis 2849 of the dowel 2848.

The anchoring elements 2838, 2840 may include one or more surface features that are resistant to side-to-side translation of the glenoid component 2800, i.e., translation in the superior-inferior and/or anterior-posterior directions. A translation resistant surface feature may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature.

The anchoring elements 2838, 2840 may include one or more surface features that are resistant to side-to-side translation of the glenoid component 2800, i.e., translation in the superior-inferior and/or anterior-posterior directions. The anchoring elements 2838, 2840 are illustrated with translation resistant surface features which are protruding dowel tips 2874, which are enlarged relative to the fundamental surface of the dowel 2848. The dowel tips 2874 may protrude from the superior and/or inferior sides of each dowel 2848 to increase the width of the dowel to resist translation. Two dowel tips 2874 are shown, with a first dowel tip 2874 protruding from the superior-posterior side of the dowel 2848 of the superior anchoring element 2838, and a second dowel tip 2874 protruding from the inferior-posterior side of the dowel 2848 of the inferior anchoring element 2840. The dowel tips 2874 terminate with the antero-laterally facing planar surfaces 2872. A beveled surface 2876 may be present near the medial free end of the dowel tip 2874. Two beveled surfaces 2876 are shown, with a first beveled surface 2876 facing superior-posterior on the superior anchoring element 2838, and a second beveled surface 2876 facing inferior-posterior on the inferior anchoring element 2840. The beveled surface(s) 2876 may reduce the force required to initially insert the dowel tips 2874 in the corresponding bone tunnels, and the interaction of the beveled surfaces 2876 and the bone tunnel mouths may cause the anchoring elements 2838, 2840 to bend toward each other as the dowel tips 2874 are inserted in the bone tunnels.

A slot 2864, or groove or channel, may be present along the dowel, the exposed side 2853 of the reinforcement plate 2852, or both. In cemented applications of the technology, the bone cement may flow along the slot(s) 2864 on the anchoring element.

The glenoid component 2800 may be operatively implanted in a scapula 2 (not shown). The scapula 2 includes a glenoid fossa 4, a coracoid process 6, and an acromion process 8. The triangular shape of the anchoring elements 2838, 2840 matches the conical shape of the glenoid vault more closely than does a central peg or keel, in a superior-inferior view. The dowels 2848 are peripherally arranged along the anterior portion 2822 in the example shown. This places the pedestal 2856 of the anchoring elements into regions of denser subchondral bone for stronger fixation. Medially in the glenoid vault, the side of the dowel 2848 and the exposed side 2853 of the reinforcement plate 2852 may lie adjacent and parallel to the thick cortical walls of the glenoid vault.

A notch 2863 may be present on the exposed side 2853 of the reinforcement plate 2852 adjacent to the dowel 2848. The notch 2863 provides relief in the anchoring elements 2838, 2840 to avoid impingement with the bone tunnel (or socket).

Referring to FIGS. 7A-7H, a glenoid component 2900 includes a body 2902 with a lateral articular surface 2904 and an opposite medial bone-facing surface 2906.

A peripheral wall 2908 extends around the body 2902 between the surfaces 2904, 2906. A lateral peripheral edge 2910 extends around the body 2902 where the lateral articular surface 2904 intersects the peripheral wall 2908. The lateral peripheral edge 2910 may be rounded or relieved by a lateral peripheral relief 2912, such as a radius, fillet, chamfer, bevel, or the like. A medial peripheral edge 2914 extends around the body 2902 where the medial bone-facing surface 2906 intersects the peripheral wall 2908. The medial peripheral edge 2914 may be rounded or relieved by a medial peripheral relief 2916, such as a radius, fillet, chamfer, bevel, or the like.

The body 2902, lateral articular surface 2904, medial bone-facing surface 2906, peripheral wall 2908, lateral peripheral edge 2910, lateral peripheral relief 2912, medial peripheral edge 2914, and/or medial peripheral relief 2916 may be divided into a superior portion 2918, an inferior portion 2920, an anterior portion 2922, and a posterior portion 2924. The body 2902, lateral articular surface 2904, and/or medial bone-facing surface 2906 may also be divided into a peripheral portion near the peripheral wall 2908 and an interior or central portion. In examples other than shoulder glenoid components, where the surgical approach trajectory may be different than the approach described herein, the appropriate medical directional terms may be readily substituted by one of skill in the art.

The lateral articular surface 2904 may be concave as shown, planar, or convex in order to complement a natural or prosthetic humeral articular surface. The lateral articular surface 2904 may be spherical. The lateral articular surface 2904 may be elliptical or ovoid. The lateral articular surface 2904 may have a first radius 2926 which is dimensionally different from, i.e., larger or smaller than, a second radius 2928. The first radius 2926 may be a superior-inferior radius, or S-I radius. The second radius 2928 may be an anterior-posterior radius, or A-P radius.

The inferior portion 2920 of the body 2902 may include an inferior chamfer 2930 which extends between the lateral articular surface 2904 and the peripheral wall 2908. The inferior chamfer 2930 is a sloping surface, preferably a planar surface, that lowers the profile and thickness of the inferior portion 2920 along the lateral peripheral edge 2910.

The medial bone-facing surface 2906 may be convex as shown, planar, or concave.

The glenoid component 2900 includes at least one anchoring element 2938 which protrudes outwardly from the medial bone-facing surface 2906. The example shown includes a superior anchoring element 2938 and an inferior anchoring element 2940, although any number of anchoring elements may be present. Each anchoring element may be independently positioned on the medial bone-facing surface 2906, and may be independently sized.

Each anchoring element 2938, 2940 includes a dowel 2948, or mast, and a triangular reinforcement plate 2952, or sail or buttress.

The dowel 2948 projects from the medial bone-facing surface 2906 at an angle 2950 less than ninety degrees and greater than zero degrees. The angle 2950 may be referred to as a dowel angle or a mast angle. The angle 2950 may be measured between a central longitudinal axis 2949 of the dowel 2948 and a plane which is coplanar with the medial bone-facing surface 2906, if surface 2906 is planar, or a plane which is tangent to the medial bone-facing surface 2906, if surface 2906 is concave or convex. The plane may be tangent to the medial bone-facing surface 2906 at an intersection point between the central longitudinal axis 2949 of the dowel 2948 and the medial bone-facing surface 2906, or at a centroid of the medial bone-facing surface 2906. The dowel 2948 may project from the anterior portion 2922 of the body 2902, as shown, or from another portion of the body 2902. In the example shown, the dowels 2948 of anchoring elements 2938, 2940 project from peripheral locations in the anterior portion 2922 and terminate in medially located free ends. The dowel 2948 may have a round fundamental cross sectional shape, as shown, or another shape, such as a rectangle or dovetail. The dowel 2948 may include a hole 2970, which may receive a radiographic marker.

The reinforcement plate 2952 projects from the medial bone-facing surface 2906 in the acute angle 2950 between the dowel 2948 and the medial bone-facing surface 2906, and coplanar with the dowel 2948. An exposed side 2953 of the reinforcement plate 2952 projects from the medial bone-facing surface 2906 at an angle 2954 less than ninety degrees and greater than zero degrees. The angle 2954 may be referred to as a reinforcement angle. The angle 2954 opens toward the angle 2950, and the sum of angles 2950 and 2954 is greater than zero degrees and less than one hundred eighty degrees. The reinforcement plate 2952 intersects the dowel 2948 to form a triangular shape with one side formed by the medial bone-facing surface 2906, one side formed by the dowel 2948, and one side formed by the exposed side 2953 of the reinforcement plate 2952. The triangular shape may be an acute triangle having three internal angles each less than 90 degrees.

The anchoring elements 2938, 2940 may include a pedestal 2956 or footing where the anchoring element intersects the medial bone-facing surface 2906. The pedestal 2956 may be present on the dowel 2948 or the reinforcement plate 2952, or both. The pedestal 2956 may enlarge the anchoring element 2938, 2940 at the medial bone-facing surface 2906. The pedestal 2956 may terminate medially in a planar face 2957 which may establish the plane from which the angles 2950, 2954 are measured. The planar face 2957 may be tangent to the medial bone-facing surface 2906.

The anchoring elements 2938, 2940, including the dowels 2948, the reinforcement plates 2952, and the pedestals 2956, may project outwardly from the medial bone-facing surface 2906 orthogonally or at an acute angle when viewed from an anterior (i.e., FIG. 1E) or posterior (i.e., FIG. 1F) direction. The acute angle may be on either side of the anchoring element, i.e., on the superior or inferior side. For example, the acute angle may be on the superior side of the superior anchoring element 2938, and on the inferior side of the inferior anchoring element 2940, or vice versa.

The anchoring elements 2938, 2940 may include surface features to improve fixation, or pull-out strength, after implantation. Surface features may be present on one or more of the anchoring elements present on a glenoid component. The surface features may project outwardly or inwardly from the fundamental surface(s) of the anchoring elements 2938, 2940. The surface features may include notches, grooves, channels, ridges, accordion texture, barbs, threads, shelves, rings, ribs, or perforations. For example, alternating ridges 2960 and grooves 2962 are shown, as well as fenestrations 2968 extending through the anchoring elements 2938, 2940. The illustrated ridges 2960 and grooves 2962 are oriented to resist axial pull-out, i.e., forces acting perpendicular to the back side of the glenoid component, or the face 2957 described below. The illustrated fenestrations 2968 resist forces acting perpendicular to their central longitudinal axes. All of these surface features may facilitate bony ingrowth or bone cement interdigitation.

A particular surface feature may be oriented on an axis parallel to and offset from the corresponding axis of the fundamental surface of the corresponding anchoring element 2938 or 2940. For example, the dowel 2948 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 2938, 2940 to bend when inserted into the bone tunnel.

The anchoring elements 2938, 2940 may include at least two surface features, wherein the first surface feature is resistant to forces acting along a first direction, wherein the second surface feature is resistant to forces acting along a second direction, wherein the first and second directions are nonparallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the mast/dowel). The first and second surface features may be intersecting planar surfaces which are side by side on a shelf of an anchoring element.

The anchoring elements 2938, 2940 may include one or more surface features that are resistant to pullout forces acting along the central longitudinal axis 2949 of the dowel 2948. The anchoring element 2940 is illustrated with a surface feature which is a protruding planar surface 2972 which faces antero-laterally. The planar surface 2972 may protrude from the superior and/or inferior sides of each dowel 2948 to increase the width of the dowel. A planar surface 2972 is shown protruding from the inferior side of the dowel 2948 of the inferior anchoring element 2940. The planar surface 2972 is perpendicular to the central longitudinal axis 2949 of the dowel 2948.

The anchoring elements 2938, 2940 may include one or more surface features that are resistant to pullout forces acting perpendicular to the central longitudinal axis 2949 of the dowel 2948. The anchoring element 2940 is illustrated with a surface feature which is a protruding planar surface 2978. The planar surface 2978 may protrude from the anterior and/or posterior side of each dowel 2948 to increase the width of the dowel. A planar surface 2978 is shown facing antero-medial on the inferior anchoring element 2940. The planar surface 2978 is parallel to the central longitudinal axis 2949 of the dowel 2948.

The anchoring elements 2938, 2940 may include one or more surface features that are resistant to side-to-side translation of the glenoid component 2900, i.e translation in the superior-inferior and/or anterior-posterior directions. A translation resistant surface feature may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature. The anchoring element 2940 is illustrated with a translation resistant surface feature which is protruding dowel tip 2974, which is enlarged relative to the fundamental surface of the dowel 2948. The dowel tip 2974 may protrude from the superior and/or inferior sides of each dowel 2948 to increase the width of the dowel to resist translation. A dowel tip 2974 is shown protruding from the inferior side of the dowel 2948 of the inferior anchoring element 2940. The dowel tip 2974 terminates with the antero-laterally facing planar surface 2972.

A slot 2964, or groove or channel, may be present along the dowel, the exposed side 2953 of the reinforcement plate 2952, or both. In cemented applications of the technology, the bone cement may flow along the slot(s) 2964 on the anchoring element.

The glenoid component 2900 may be operatively implanted in a scapula 2 (not shown). The scapula 2 includes a glenoid fossa 4, a coracoid process 6, and an acromion process 8. The triangular shape of the anchoring elements 2938, 2940 matches the conical shape of the glenoid vault more closely than does a central peg or keel, in a superior-inferior view. The dowels 2948 are peripherally arranged along the anterior portion 2922 in the example shown. This places the pedestal 2956 of the anchoring elements into regions of denser subchondral bone for stronger fixation. Medially in the glenoid vault, the side of the dowel 2948 and the exposed side 2953 of the reinforcement plate 2952 may lie adjacent and parallel to the thick cortical walls of the glenoid vault.

Referring to FIGS. 8A-13J, a prosthetic implant includes an articulating surface and a bone facing surface, where the bone facing surface includes multiple anchoring elements projecting from the bone-facing surface. The implant may be a monolithic device, or it may be constructed of multiple parts that when assembled, provide for the same overall construct with similar working properties as a monolithic device. The implant may be made of polyethylene, pyrocarbon, metal, or any other material commonly used in orthopedic devices, or may be a combination of these materials.

The bone facing anchoring elements lie along roughly parallel axes. When inserted into the prepared bone, the anchoring elements deform slightly to provide an interference fit and resist pull-out. Note that it is not just a portion of the anchoring element that deforms, such as a projecting barb or rib, but the primary or longest axis of the anchoring element which deforms to aid in fixation. In other words, the long axis of the anchoring element bends as the anchoring element deforms macroscopically.

A key advantage of glenoid implants with anchoring elements deforming along a long axis (or longest dimension) is immediate stability. Even if used with bone cement, this design provides static fixation before cement has hardened.

In one embodiment, two of the anchoring elements deform within the same plane, either toward or away from each other. The plane contains the central longitudinal axes of the anchoring elements. A third anchoring element deforms in a plane perpendicular to the other two anchoring elements. This second plane contains the central longitudinal axis of the third anchoring element. Additional deforming anchoring elements may be included in other non-orthogonal planes.

The two deforming anchoring elements that deform within the same plane provide resistance to motion in a hypothetical X and Y plane (or 2 dimensions): the plane in which they converge or diverge, and a plane perpendicular to that plane which resists pull-out. Addition of the third anchoring element that deforms in a plane perpendicular to the other two anchoring elements provides resistance to motion in a hypothetical Z plane (or 3rd dimension) as well.

The deforming anchoring elements, when inserted into bone, provide static resistance to movement in these planes. Addition of a barb, shelf, or otherwise outward projection or inward recess on one or more of the anchoring elements provides additional pull-out resistance.

The deforming anchoring elements are roughly parallel to each other so they can be inserted as a unit along a single trajectory, but they are not necessarily all the same length.

In another embodiment, the implant may include two deforming anchoring elements lying in a single plane, with at least one more anchoring element which does not deform, but provides resistance to motion in another plane.

In another embodiment, the device may include two non-deforming anchoring elements lying in a single plane, with at least one more anchoring element which deforms in any other plane.

Glenoid implants with anchoring elements deforming along a long axis (or longest dimension) may have one or more of the following prominent attributes:
  Two or more deforming anchoring elements in a glenoid component which converge or diverge from each other to enhance fixation.
  Deforming anchoring elements in one plane with another anchoring element to provide resistance to movement in another non-parallel plane.
  Deforming anchoring elements that deform in multiple non parallel planes.
  Non-deforming anchoring elements in one plane with a deforming anchoring element in another plane.

In an embodiment, an implant has two deforming anchoring elements.

In another embodiment, an implant has two deforming anchoring elements plus a third static anchoring element that is non-deforming.

In yet another embodiment, an implant has three deforming anchoring elements, wherein two of the anchoring elements deform in a first plane, wherein a third anchoring element deforms in a separate (non parallel) second plane. The second plane may be orthogonal to the first plane, but could be any other plane.

In yet another embodiment, an implant has three or more anchoring elements, with two or more non-deforming anchoring elements oriented along parallel axes, wherein the parallel axes define a first plane, with one or more deforming anchoring element(s) which deforms in a different plane than the first plane.

In yet another embodiment, any of the preceding implants has anchoring elements that are not orthogonal to the backside of the implant. In other words, the anchoring elements extends outwardly from the bone-facing surface at an acute angle instead of a 90 degree angle.

In yet another embodiment, any of the preceding implants has anchoring elements of varied lengths.

In yet another embodiment, any of the preceding implants has transverse projections or indentations to provide additional resistance to pull-out.

In yet another embodiment, an implant has anchoring elements that are all oriented along parallel axes, which when inserted deform so that the axes are no longer parallel. In some embodiments, after insertion, the axes may be curved instead of straight.

In yet another embodiment, an implant has anchoring elements that are all oriented along non-parallel axes, which when inserted deform so that two or more of the axes become parallel.

In yet another embodiment, an implant has anchoring elements that are all oriented along non-parallel axes, which when inserted deform so that at least one of the axes has a different orientation than before insertion.

Referring to FIGS. 8A-8K, a glenoid component 3000 includes a body 3002 with a lateral articular surface 3004 and an opposite medial bone-facing surface 3006.

A peripheral wall 3008 extends around the body 3002 between the surfaces 3004, 3006. A lateral peripheral edge 3010 extends around the body 3002 where the lateral articular surface 3004 intersects the peripheral wall 3008. The lateral peripheral edge 3010 may be rounded or relieved by a lateral peripheral relief 3012, such as a radius, fillet, chamfer, bevel, or the like. A medial peripheral edge 3014 extends around the body 3002 where the medial bone-facing surface 3006 intersects the peripheral wall 3008. The medial peripheral edge 3014 may be rounded or relieved by a medial peripheral relief 3016, such as a radius, fillet, chamfer, bevel, or the like.

The body 3002, lateral articular surface 3004, medial bone-facing surface 3006, peripheral wall 3008, lateral peripheral edge 3010, lateral peripheral relief 3012, medial peripheral edge 3014, and/or medial peripheral relief 3016 may be divided into a superior portion 3018, an inferior portion 3020, an anterior portion 3022, and a posterior portion 3024. The body 3002, lateral articular surface 3004, and/or medial bone-facing surface 3006 may also be divided into a peripheral portion near the peripheral wall 3008 and an interior or central portion. In examples other than shoulder glenoid components, where the surgical approach trajectory may be different than the approach described herein, the appropriate medical directional terms may be readily substituted by one of skill in the art.

Figure 8A:
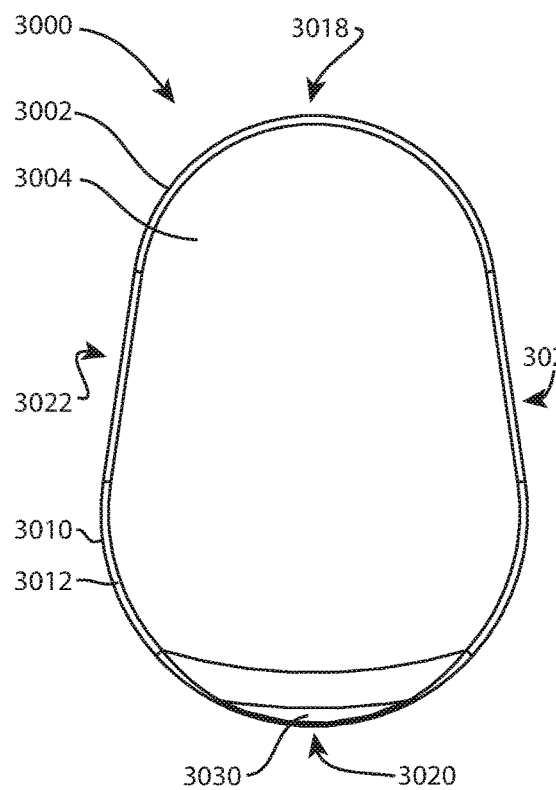
FIG. 8A is a lateral view of a glenoid component.
Figure 8B:
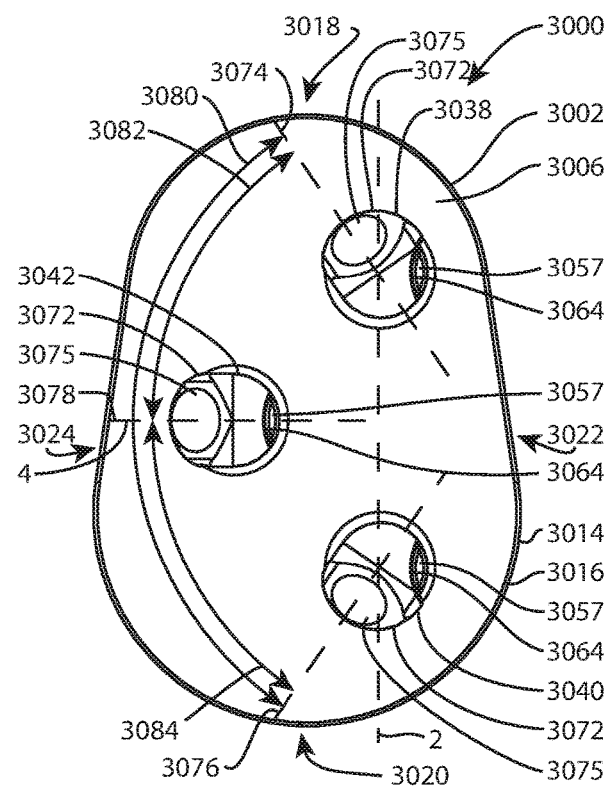
FIG. 8B is a medial view of the glenoid component of FIG. 8A.
Figures 8C, 8D:
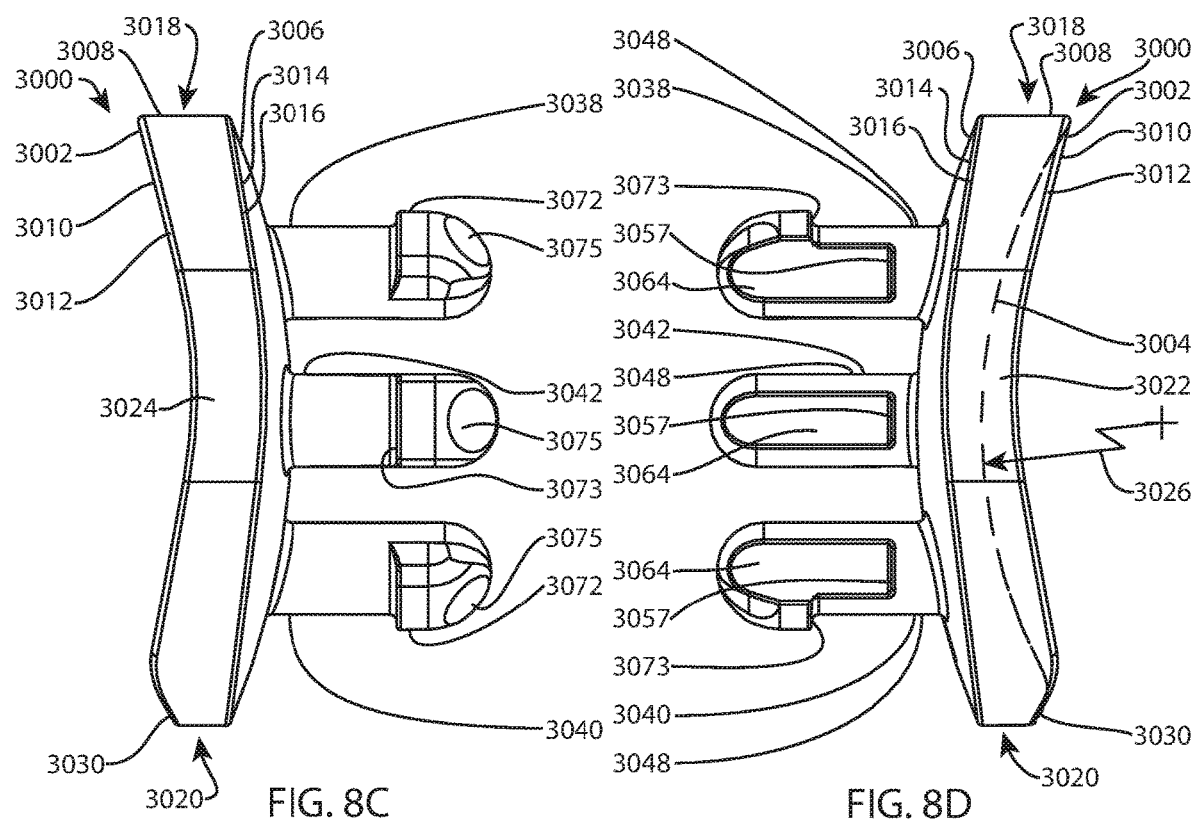
FIG. 8C is a posterior view of the glenoid component of FIG. 8A.
FIG. 8D is an anterior view of the glenoid component of FIG. 8A.
Figure 8E:
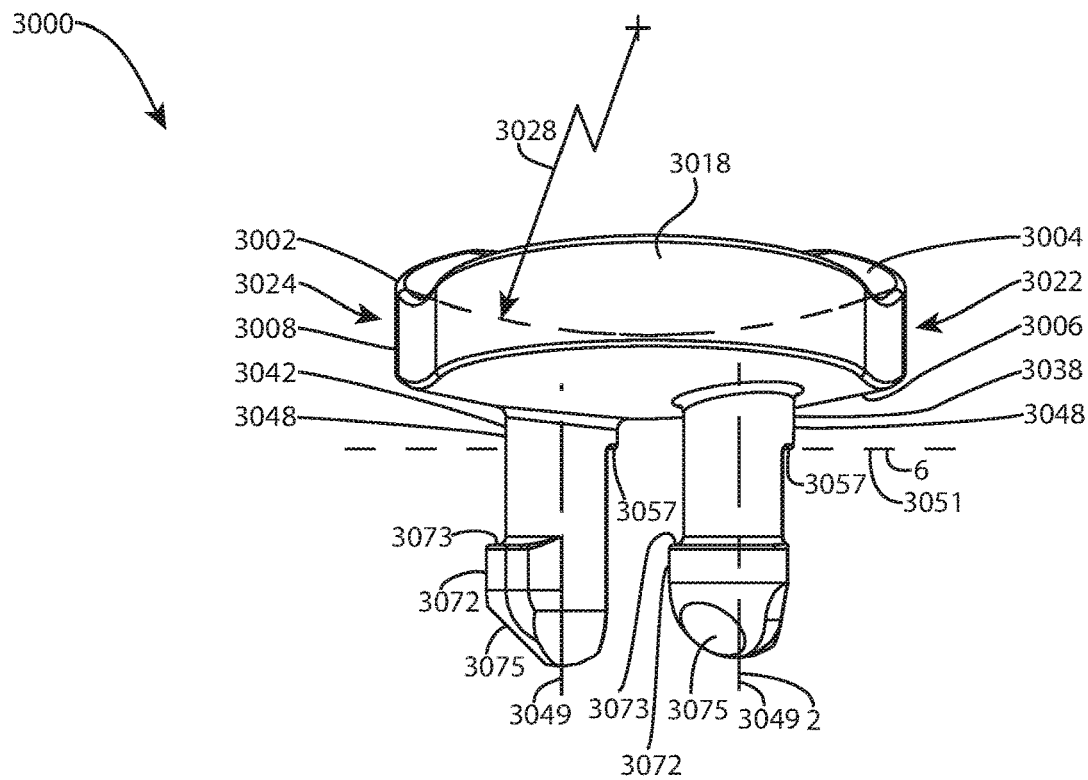
FIG. 8E is a superior view of the glenoid component of FIG. 8A.

The lateral articular surface 3004 may be concave, as shown best in FIGS. 8D and 8E, planar, or convex in order to complement a natural or prosthetic humeral articular surface. The lateral articular surface 3004 may be spherical, elliptical, or ovoid. The lateral articular surface 3004 may have a first radius 3026 which is dimensionally different from, i.e., larger or smaller than, a second radius 3028. The first radius 3026 may be a superior-inferior radius, or S-I radius. The second radius 3028 may be an anterior-posterior radius, or A-P radius.

The inferior portion 3020 of the body 3002 may include an inferior chamfer 3030 which extends between the lateral articular surface 3004 and the peripheral wall 3008. The inferior chamfer 3030 is a sloping surface, preferably a planar surface, that lowers the profile and thickness of the inferior portion 3020 along the lateral peripheral edge 3010.

The medial bone-facing surface 3006 may be convex as shown, planar, or concave.

The glenoid component 3000 includes at least one anchoring element 3038 which protrudes outwardly from the medial bone-facing surface 3006. The example shown includes a superior anchoring element 3038, an inferior anchoring element 3040, and a middle anchoring element 3042, although any number of anchoring elements may be present. Each anchoring element may be independently positioned on the medial bone-facing surface 3006, and may be independently sized.

Figure 8F:
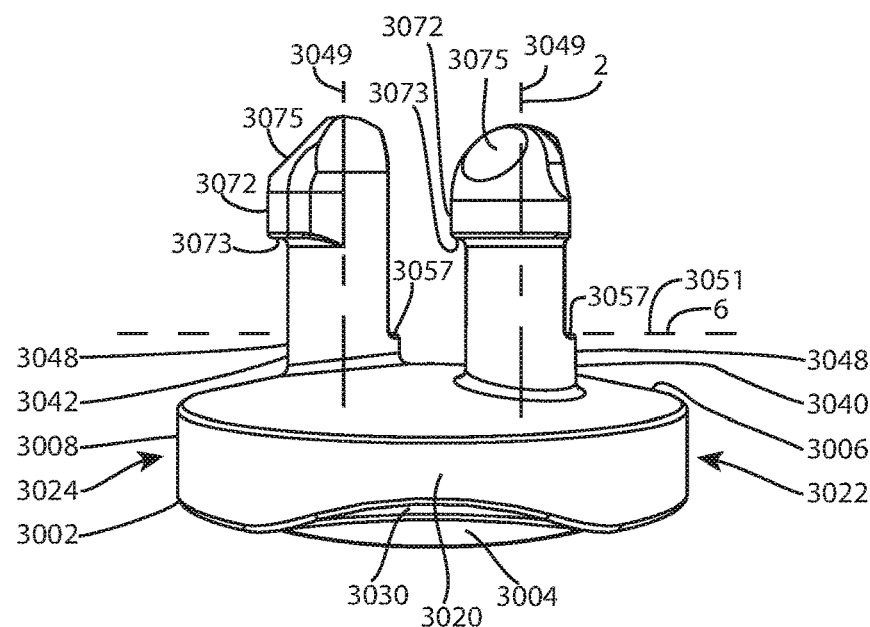
FIG. 8F is an inferior view of the glenoid component of FIG. 8A.

Each anchoring element 3038, 3040, 3042 includes a dowel 3048. Each dowel 3048 includes a central longitudinal axis 3049. The axes 3049 of the dowels 3048 may be parallel within a tolerance of ten degrees, eight degrees, six degrees, four degrees, two degrees, or one degree. Referring to FIGS. 8B, 8E, and 8F, the axes 3049 of the dowels 3048 of the anchoring elements 3038, 3040 lie on the first plane 2. The axis 3049 of the dowel 3048 of the anchoring element 3042 lies on the second plane 4. The first and second planes 2, 4 are represented as lines since they are viewed on edge.

A plane 3051 may be coplanar with the medial bone-facing surface 3006, if surface 3006 is planar, or tangent to the medial bone-facing surface 3006, if surface 3006 is concave or convex. The plane 3051 may be tangent to the medial bone-facing surface 3006 at an intersection point between the central longitudinal axis 3049 of the dowel 3048 and the medial bone-facing surface 3006, or at a centroid of the medial bone-facing surface 3006. The dowel 3048 may project from the anterior portion 3022 of the body 3002, as shown for the anchoring elements 3038, 3040, or from another portion of the body 3002; the dowel 3048 of the middle anchoring element 3042 is shown projecting from the posterior portion 3024 of the body 3002. The dowel 3048 may have a round fundamental cross sectional shape, as shown, or another shape, such as a rectangle or dovetail. The dowel 3048 may include a hole, which may receive a radiographic marker.

The anchoring elements 3038, 3040, including the dowels 3048, may project outwardly from the medial bone-facing surface 3006 orthogonally as shown in FIGS. 8C and 8D or at an acute angle when viewed from an anterior direction (FIG. 8D) or a posterior direction (FIG. 8C). The acute angle may be on either side of the anchoring element, i.e., on the superior or inferior side. For example, the acute angle may be on the superior side of the superior anchoring element 3038, and on the inferior side of the inferior anchoring element 3040 so that the anchoring elements 3038, 3040 diverge as they extend medially, or vice versa so that the anchoring elements 3038, 3040 converge as they extend medially.

A slot 3064, or groove or channel, may be present along the dowel 3048. Anterior slots 3064 are shown on the dowels 3048 of the anchoring elements 3038, 3040, 3042. In cemented applications of the technology, the bone cement may flow along the slot 3064. The slot 3064 may terminate laterally in a planar face 3057 which may establish the plane 3051. The planar face 3057 may be tangent to the medial bone-facing surface 3006.

The anchoring elements 3038, 3040, 3042 may include surface features to improve fixation, or pull-out strength, after implantation. The surface features may facilitate bony ingrowth or bone cement interdigitation. Surface features may be present on one or more of the anchoring elements present on a glenoid component. The surface features may project outwardly or inwardly from the fundamental surface(s) of the anchoring elements 3038, 3040, 3042. The surface features may include notches, grooves, channels, ridges, accordion texture, barbs, threads, shelves, rings, ribs, or perforations.

A particular surface feature may be oriented on an axis parallel to and offset from the corresponding axis of the fundamental surface of the corresponding anchoring element 3038 or 3040. For example, the dowel 3048 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 3038, 3040 to bend when inserted into the bone tunnel.

The anchoring elements 3038, 3040 may include at least two surface features, wherein the first surface feature is resistant to forces acting along a first direction, wherein the second surface feature is resistant to forces acting along a second direction, wherein the first and second directions are nonparallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the dowel). The first and second surface features may be intersecting planar surfaces which are side by side on a shelf of an anchoring element.

The anchoring elements 3038, 3040 may include one or more surface features that are resistant to side-to-side translation of the glenoid component 3000, i.e., translation in the superior-inferior and/or anterior-posterior directions. A translation resistant surface feature may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature.

The free end of the dowel 3048 of each anchoring element 3038, 3040, 3042 includes an enlarged portion 3072 that protrudes to one side of the dowel. A shelf 3073 is formed between the enlarged portion 3072 and the normal sized dowel 3048. A bevel 3075 may be present at the free end of the enlarged portion 3072. The enlarged portion 3072 may protrude to any side of the dowel 3048. Referring to FIG.

8B, the enlarged portion 3072 of the superior anchoring element 3038 protrudes along a first direction indicated by dashed line 3074, the enlarged portion 3072 of the inferior anchoring element 3040 protrudes along a second direction indicated by dashed line 3076, and the enlarged portion 3072 of the middle anchoring element 3042 protrudes along a third direction indicated by dashed line 3078. Line 3074 extends in an anterior-inferior to posterior-superior direction. Line 3076 extends in an anterior-superior to posterior-inferior direction. Lines 3074 and 3076 form an angle 3080. Line 3078 extends in an anterior-posterior direction. Lines 3074 and 3078 form an angle 3082. Lines 3076 and 3078 form an angle 3084. Line 3078 may bisect the angle 3080 between lines 3074 and 3076. During insertion, as each dowel 3048 enters the corresponding bone hole, the enlarged portion 3072 (specifically the bevel 3075 if present) pushes against the corresponding side of the bone hole. The bone resists, forcing the free end of the dowel 3048 to deflect so that the dowel 3048 bends along its axis 3049. The illustrated arrangement of enlarged portions 3072 causes anchoring elements 3038, 3040 to bend toward each other in the first plane 2 and urges the anterior side of the anchoring elements 3038, 3040, 3042 toward the corresponding wall of the bone hole. Since all of the anchoring elements 3038, 3040, 3042 are urged anteriorly in the illustrated arrangement, the entire glenoid component 3000 is urged anteriorly as well. The anchoring element 3042 may bend in the second plane 4, and may prevent the glenoid component 3000 from rocking in the second plane 4. In other words, rocking or rotating in an anterior-posterior direction about an axis that extends substantially in a superior-inferior direction, or experiencing anterior or posterior lift-off or lever-out.

Figure 8K:
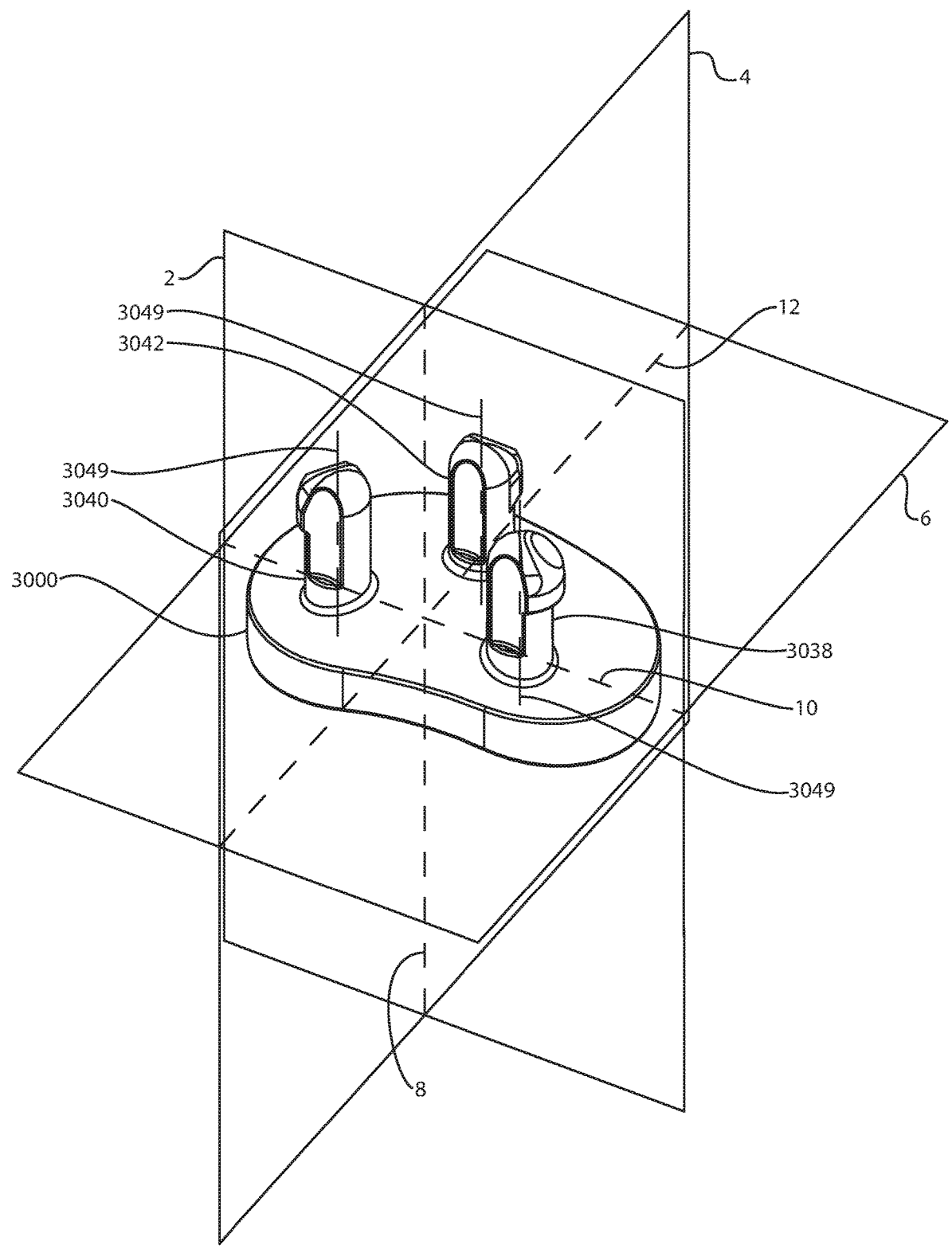
FIG. 8K is an isometric view of the glenoid component of FIG. 8A superimposed on a set of three mutually perpendicular planes.

Referring to FIG. 8K, the glenoid component 3000 is shown in an isometric view superimposed on a set of three mutually perpendicular planes. A first plane 2 contains the central longitudinal axes 3049 of the superior and inferior anchoring elements 3038 and 3040. A second plane 4 contains the central longitudinal axis 3049 of the middle anchoring element 3042. The second plane 4 is perpendicular to the first plane 2. The first and second planes 2, 4 intersect along dashed line 8. A third plane 6 may contain at least one point of the medial bone-facing surface 3006, or may be the plane 3051 or may contain the planar face 3057. The third plane 6 is perpendicular to the first plane 2 and the second plane 4. The first and third planes 2, 6 intersect along dashed line 10. The second and third planes 4, 6 intersect along dashed line 12. FIG. 8K pertains to each of the glenoid components 3000, 3100, 3200, 3300, 3400 disclosed in this application. The first, second, and third planes 2, 4, 6, and the dashed lines 8, 10, 12 also pertain to each of the glenoid components disclosed in this application. However, the orientation of the first plane 2 varies among the embodiments as discussed below.

In the context of a glenoid component, the first plane 2, the second plane 4, and the third plane 6 correspond at least generally to anatomical reference directions and planes. The first plane 2 may extend in a superior-inferior direction, and may correspond to the coronal plane or the scapular plane. The second plane may extend in an anterior-posterior direction, and may correspond to the transverse plane. The third plane may extend tangent to the glenoid articular surface, or may be parallel to the sagittal plane.

The anchoring elements 3038 and 3042 deflect in the first plane 2 and the anchoring element 3042 deflects in the second plane 4. When the anchoring elements 3038 and 3042 deflect, they provide resistance to motion in the first plane 2 and the second plane 4. More specifically, the anchoring elements 3038 and 3042 provide resistance to pull-out in the second plane 4.

Referring to FIGS. 9A-9J, another glenoid component 3100 includes a body 3102 with a lateral articular surface 3104 and an opposite medial bone-facing surface 3106.

A peripheral wall 3108 extends around the body 3102 between the surfaces 3104, 3106. A lateral peripheral edge 3110 extends around the body 3102 where the lateral articular surface 3104 intersects the peripheral wall 3108. The lateral peripheral edge 3110 may be rounded or relieved by a lateral peripheral relief 3112, such as a radius, fillet, chamfer, bevel, or the like. A medial peripheral edge 3114 extends around the body 3102 where the medial bone-facing surface 3106 intersects the peripheral wall 3108. The medial peripheral edge 3114 may be rounded or relieved by a medial peripheral relief 3116, such as a radius, fillet, chamfer, bevel, or the like.

The body 3102, lateral articular surface 3104, medial bone-facing surface 3106, peripheral wall 3108, lateral peripheral edge 3110, lateral peripheral relief 3112, medial peripheral edge 3114, and/or medial peripheral relief 3116 may be divided into a superior portion 3118, an inferior portion 3120, an anterior portion 3122, and a posterior portion 3124. The body 3102, lateral articular surface 3104, and/or medial bone-facing surface 3106 may also be divided into a peripheral portion near the peripheral wall 3108 and an interior or central portion. In examples other than shoulder glenoid components, where the surgical approach trajectory may be different than the approach described herein, the appropriate medical directional terms may be readily substituted by one of skill in the art.

Figure 9E:
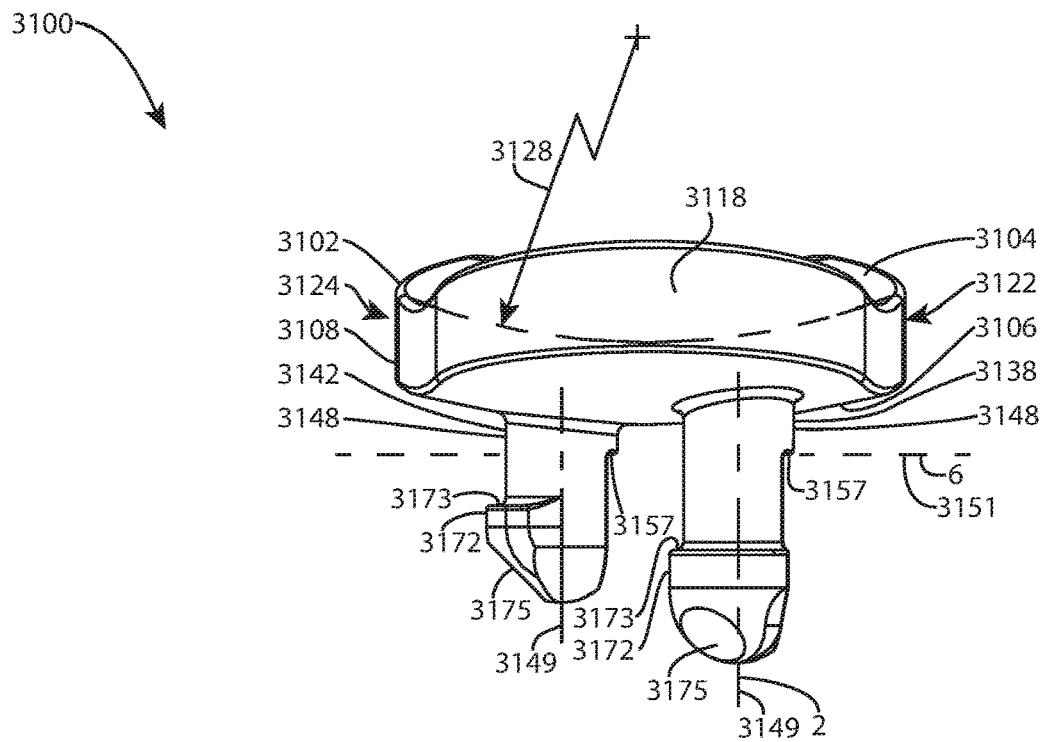
FIG. 9E is a superior view of the glenoid component of FIG. 9A.

The lateral articular surface 3104 may be concave, as shown best in FIGS. 9D and 9E, planar, or convex in order to complement a natural or prosthetic humeral articular surface. The lateral articular surface 3104 may be spherical, elliptical, or ovoid. The lateral articular surface 3104 may have a first radius 3126 which is dimensionally different from, i.e., larger or smaller than, a second radius 3128. The first radius 3126 may be a superior-inferior radius, or S-I radius. The second radius 3128 may be an anterior-posterior radius, or A-P radius.

The inferior portion 3120 of the body 3102 may include an inferior chamfer 3130 which extends between the lateral articular surface 3104 and the peripheral wall 3108. The inferior chamfer 3130 is a sloping surface, preferably a planar surface, that lowers the profile and thickness of the inferior portion 3120 along the lateral peripheral edge 3110.

The medial bone-facing surface 3106 may be convex as shown, planar, or concave.

The glenoid component 3100 includes at least one anchoring element 3138 which protrudes outwardly from the medial bone-facing surface 3106. The example shown includes a superior anchoring element 3138, an inferior anchoring element 3140, and a middle anchoring element 3142, although any number of anchoring elements may be present. Each anchoring element may be independently positioned on the medial bone-facing surface 3106, and may be independently sized.

Figure 9F:
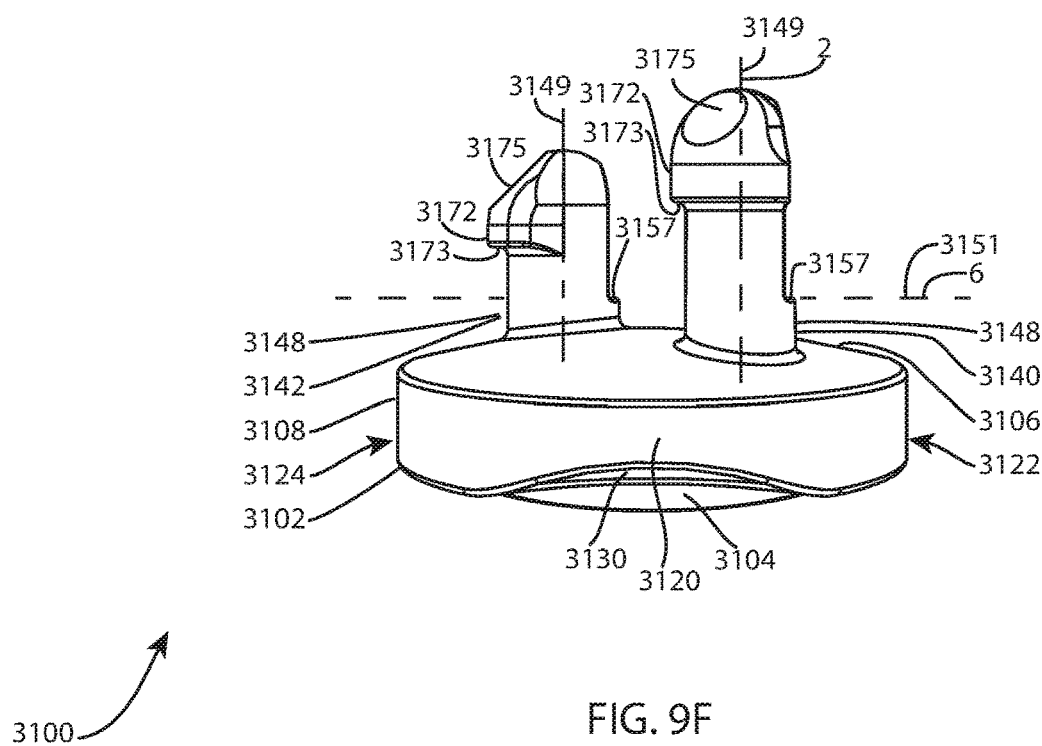
FIG. 9F is an inferior view of the glenoid component of FIG. 9A.

Each anchoring element 3138, 3140, 3142 includes a dowel 3148. Each dowel 3148 includes a central longitudinal axis 3149. The axes 3149 of the dowels 3148 may be parallel within a tolerance of ten degrees, eight degrees, six degrees, four degrees, two degrees, or one degree. Referring to FIGS. 9B, 9E, and 9F, the axes 3149 of the dowels 3148 of the anchoring elements 3138, 3140 lie on the first plane 2. The axis 3149 of the dowel 3148 of the anchoring element 3142 lies on the second plane 4. The first and second planes 2, 4 are represented as lines since they are viewed on edge.

A plane 3151 may be coplanar with the medial bone-facing surface 3106, if surface 3106 is planar, or tangent to the medial bone-facing surface 3106, if surface 3106 is concave or convex. The plane 3151 may be tangent to the medial bone-facing surface 3106 at an intersection point between the central longitudinal axis 3149 of the dowel 3148 and the medial bone-facing surface 3106, or at a centroid of the medial bone-facing surface 3106. The dowel 3148 may project from the anterior portion 3122 of the body 3102, as shown for the anchoring elements 3138, 3140, or from another portion of the body 3102; the dowel 3148 of the middle anchoring element 3142 is shown projecting from the interior portion of the body 3102. The dowel 3148 may have a round fundamental cross sectional shape, as shown, or another shape, such as a rectangle or dovetail. The dowel 3148 may include a hole, which may receive a radiographic marker.

The anchoring elements 3138, 3140, including the dowels 3148, may project outwardly from the medial bone-facing surface 3106 orthogonally as shown in FIGS. 9C and 9D or at an acute angle when viewed from an anterior direction (FIG. 9D) or a posterior direction (FIG. 9C). The acute angle may be on either side of the anchoring element, i.e., on the superior or inferior side. For example, the acute angle may be on the superior side of the superior anchoring element 3138, and on the inferior side of the inferior anchoring element 3140 so that the anchoring elements 3138, 3140 diverge as they extend medially, or vice versa so that the anchoring elements 3138, 3140 converge as they extend medially.

A slot 3164, or groove or channel, may be present along the dowel 3148. Anterior slots 3164 are shown on the dowels 3148 of the anchoring elements 3138, 3140, 3142. In cemented applications of the technology, the bone cement may flow along the slot 3164. The slot 3164 may terminate laterally in a planar face 3157 which may establish the plane 3151. The planar face 3157 may be tangent to the medial bone-facing surface 3106.

The anchoring elements 3138, 3140, 3142 may include surface features to improve fixation, or pull-out strength, after implantation. The surface features may facilitate bony ingrowth or bone cement interdigitation. Surface features may be present on one or more of the anchoring elements present on a glenoid component. The surface features may project outwardly or inwardly from the fundamental surface(s) of the anchoring elements 3138, 3140, 3142. The surface features may include notches, grooves, channels, ridges, accordion texture, barbs, threads, shelves, rings, ribs, or perforations.

A particular surface feature may be oriented on an axis parallel to and offset from the corresponding axis of the fundamental surface of the corresponding anchoring element 3138 or 3140. For example, the dowel 3148 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 3138, 3140 to bend when inserted into the bone tunnel.

The anchoring elements 3138, 3140 may include at least two surface features, wherein the first surface feature is resistant to forces acting along a first direction, wherein the second surface feature is resistant to forces acting along a second direction, wherein the first and second directions are nonparallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the dowel). The first and second surface features may be intersecting planar surfaces which are side by side on a shelf of an anchoring element.

The anchoring elements 3138, 3140 may include one or more surface features that are resistant to side-to-side translation of the glenoid component 3100, i.e., translation in the superior-inferior and/or anterior-posterior directions. A translation resistant surface feature may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature.

The free end of the dowel 3148 of each anchoring element 3138, 3140, 3142 includes an enlarged portion 3172 that protrudes to one side of the dowel. A shelf 3173 is formed between the enlarged portion 3172 and the normal sized dowel 3148. A bevel 3175 may be present at the free end of the enlarged portion 3172. The enlarged portion 3172 may protrude to any side of the dowel 3148. Referring to FIG. 9B, the enlarged portion 3172 of the superior anchoring element 3138 protrudes along a first direction indicated by dashed line 3174, the enlarged portion 3172 of the inferior anchoring element 3140 protrudes along a second direction indicated by dashed line 3176, and the enlarged portion 3172 of the middle anchoring element 3142 protrudes along a third direction indicated by dashed line 3178. Line 3174 extends in an anterior-inferior to posterior-superior direction. Line 3176 extends in an anterior-superior to posterior-inferior direction. Lines 3174 and 3176 form an angle 3180. Line 3178 extends in an anterior-posterior direction. Lines 3174 and 3178 form an angle 3182. Lines 3176 and 3178 form an angle 3184. Line 3178 may bisect the angle 3180 between lines 3174 and 3176. During insertion, as each dowel 3148 enters the corresponding bone hole, the enlarged portion 3172 (specifically the bevel 3175 if present) pushes against the corresponding side of the bone hole. The bone resists, forcing the free end of the dowel 3148 to deflect so that the dowel 3148 bends along its axis 3149. The illustrated arrangement of enlarged portions 3172 causes anchoring elements 3138, 3140 to bend toward each other in the first plane 2 and urges the anterior side of the anchoring elements 3138, 3140, 3142 toward the corresponding wall of the bone hole. Since all of the anchoring elements 3138, 3140, 3142 are urged anteriorly in the illustrated arrangement, the entire glenoid component 3100 is urged anteriorly as well. The anchoring element 3142 may bend in the second plane 4, and may prevent the glenoid component 3100 from rocking in the second plane 4. In other words, rocking or rotating in an anterior-posterior direction about an axis that extends substantially in a superior-inferior direction, or experiencing anterior or posterior lift-off or lever-out.

Referring to FIGS. 10A-10J, yet another glenoid component 3200 includes a body 3202 with a lateral articular surface 3204 and an opposite medial bone-facing surface 3206.

A peripheral wall 3208 extends around the body 3202 between the surfaces 3204, 3206. A lateral peripheral edge 3210 extends around the body 3202 where the lateral articular surface 3204 intersects the peripheral wall 3208. The lateral peripheral edge 3210 may be rounded or relieved by a lateral peripheral relief 3212, such as a radius, fillet, chamfer, bevel, or the like. A medial peripheral edge 3214 extends around the body 3202 where the medial bone-facing surface 3206 intersects the peripheral wall 3208. The medial peripheral edge 3214 may be rounded or relieved by a medial peripheral relief 3216, such as a radius, fillet, chamfer, bevel, or the like.

The body 3202, lateral articular surface 3204, medial bone-facing surface 3206, peripheral wall 3208, lateral peripheral edge 3210, lateral peripheral relief 3212, medial peripheral edge 3214, and/or medial peripheral relief 3216 may be divided into a superior portion 3218, an inferior portion 3220, an anterior portion 3222, and a posterior portion 3224. The body 3202, lateral articular surface 3204, and/or medial bone-facing surface 3206 may also be divided into a peripheral portion near the peripheral wall 3208 and an interior or central portion. In examples other than shoulder glenoid components, where the surgical approach trajectory may be different than the approach described herein, the appropriate medical directional terms may be readily substituted by one of skill in the art.

Figure 10A:
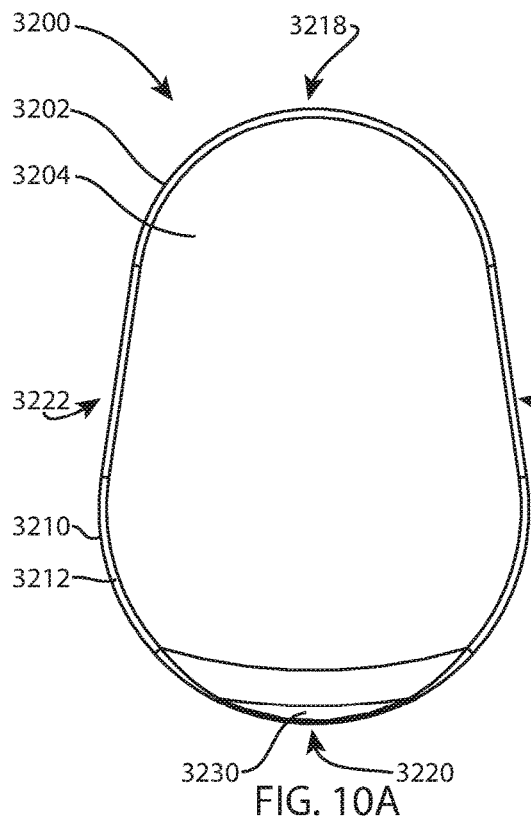
FIG. 10A is a lateral view of yet another glenoid component.
Figure 10B:
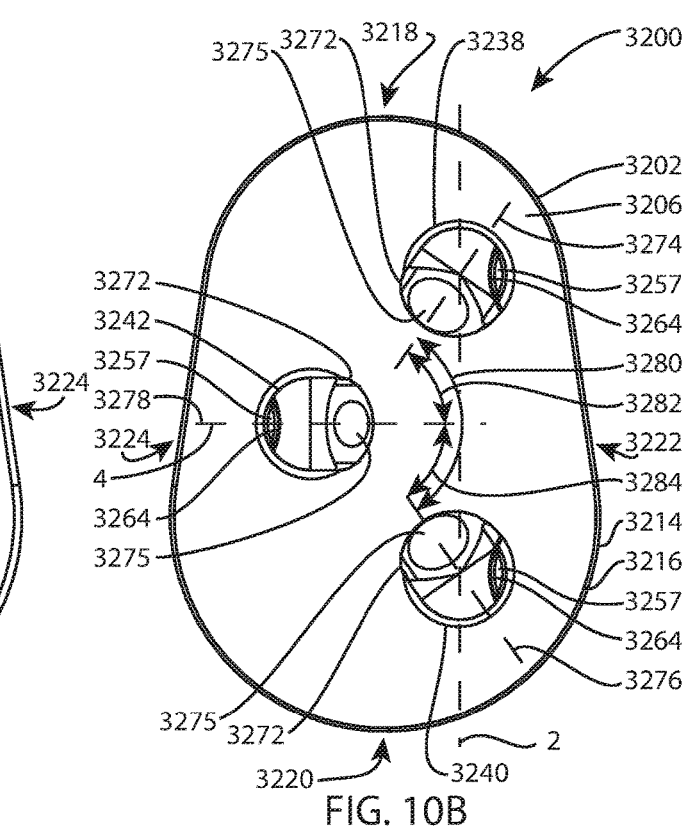
FIG. 10B is a medial view of the glenoid component of FIG. 10A.
Figure 10C:
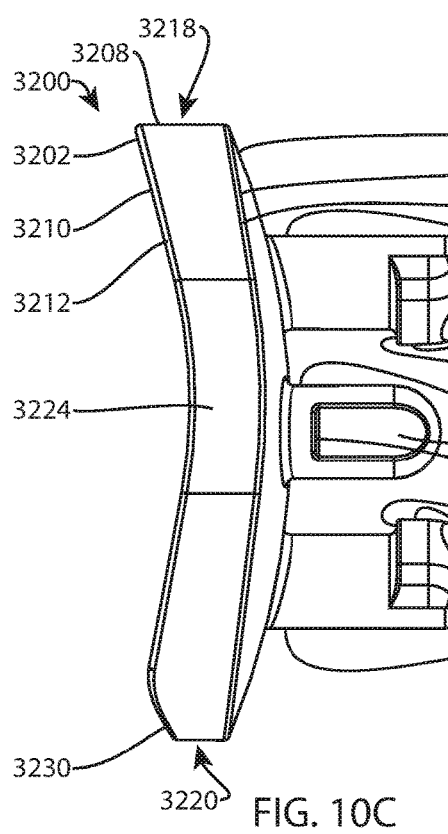
FIG. 10C is a posterior view of the glenoid component of FIG. 10A.
Figure 10D:
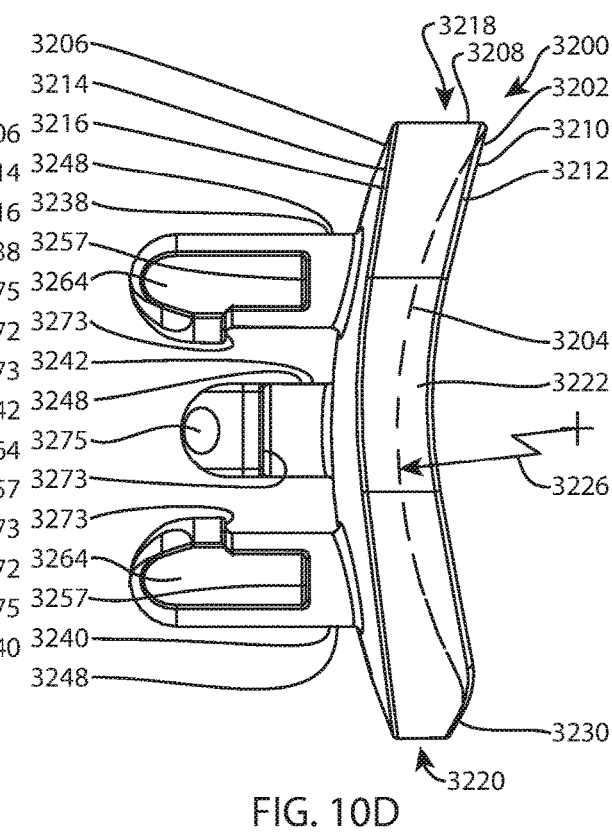
FIG. 10D is an anterior view of the glenoid component of FIG. 10A.
Figure 10E:
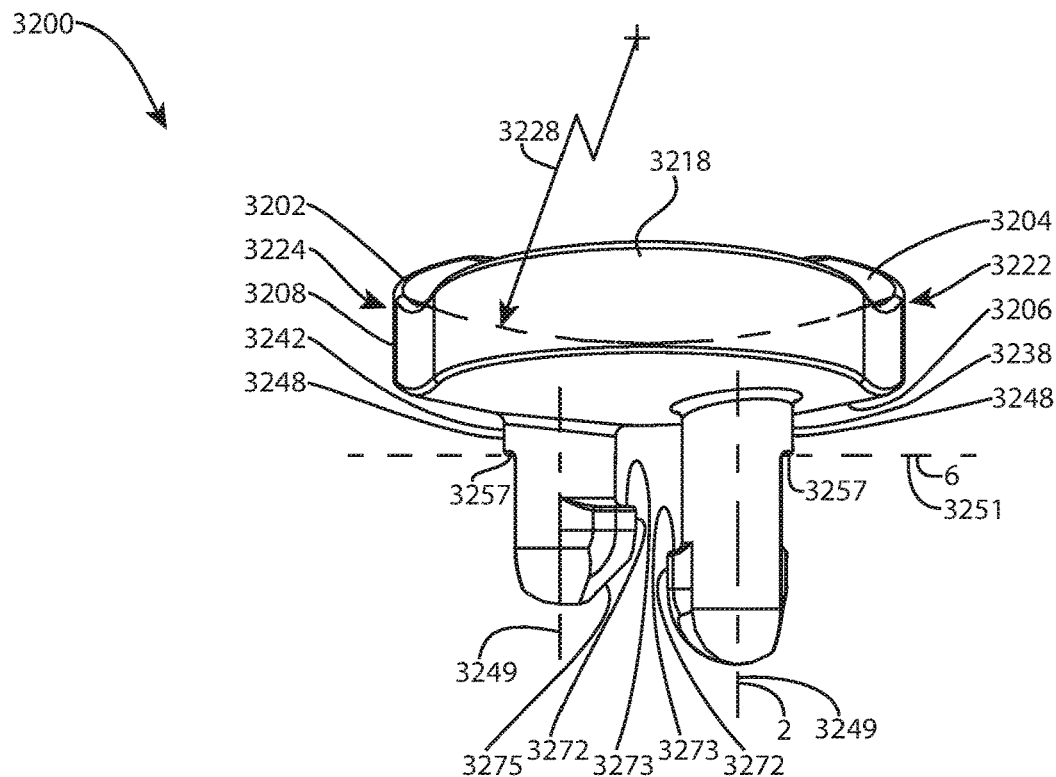
FIG. 10E is a superior view of the glenoid component of FIG. 10A.

The lateral articular surface 3204 may be concave, as shown best in FIGS. 10D and 10E, planar, or convex in order to complement a natural or prosthetic humeral articular surface. The lateral articular surface 3204 may be spherical, elliptical, or ovoid. The lateral articular surface 3204 may have a first radius 3226 which is dimensionally different from, i.e., larger or smaller than, a second radius 3228. The first radius 3226 may be a superior-inferior radius, or S-I radius. The second radius 3228 may be an anterior-posterior radius, or A-P radius.

The inferior portion 3220 of the body 3202 may include an inferior chamfer 3230 which extends between the lateral articular surface 3204 and the peripheral wall 3208. The inferior chamfer 3230 is a sloping surface, preferably a planar surface, that lowers the profile and thickness of the inferior portion 3220 along the lateral peripheral edge 3210.

The medial bone-facing surface 3206 may be convex as shown, planar, or concave.

The glenoid component 3200 includes at least one anchoring element 3238 which protrudes outwardly from the medial bone-facing surface 3206. The example shown includes a superior anchoring element 3238, an inferior anchoring element 3240, and a middle anchoring element 3242, although any number of anchoring elements may be present. Each anchoring element may be independently positioned on the medial bone-facing surface 3206, and may be independently sized.

Figure 10F:
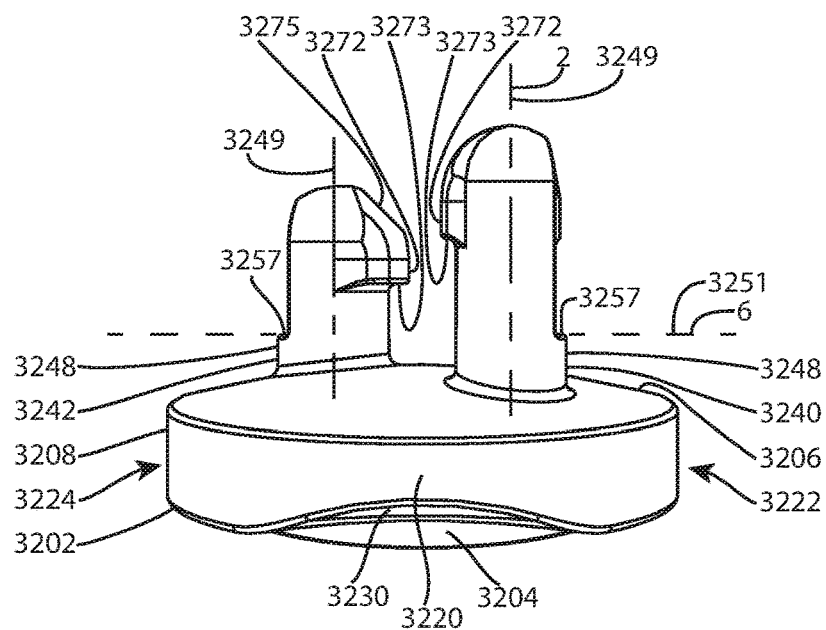
FIG. 10F is an inferior view of the glenoid component of FIG. 10A.

Each anchoring element 3238, 3240, 3242 includes a dowel 3248. Each dowel 3248 includes a central longitudinal axis 3249. The axes 3249 of the dowels 3248 may be parallel within a tolerance of ten degrees, eight degrees, six degrees, four degrees, two degrees, or one degree. Referring to FIGS. 10B, 10E, and 10F, the axes 3249 of the dowels 3248 of the anchoring elements 3238, 3240 lie on the first plane 2. The axis 3249 of the dowel 3248 of the anchoring element 3242 lies on the second plane 4. The first and second planes 2, 4 are represented as lines since they are viewed on edge.

A plane 3251 may be coplanar with the medial bone-facing surface 3206, if surface 3206 is planar, or tangent to the medial bone-facing surface 3206, if surface 3206 is concave or convex. The plane 3251 may be tangent to the medial bone-facing surface 3206 at an intersection point between the central longitudinal axis 3249 of the dowel 3248 and the medial bone-facing surface 3206, or at a centroid of the medial bone-facing surface 3206. The dowel 3248 may project from the anterior portion 3222 of the body 3202, as shown for the anchoring elements 3238, 3240, or from another portion of the body 3202; the dowel 3248 of the middle anchoring element 3242 is shown projecting from the posterior portion 3224 of the body 3202. The dowel 3248 may have a round fundamental cross sectional shape, as shown, or another shape, such as a rectangle or dovetail. The dowel 3248 may include a hole, which may receive a radiographic marker.

The anchoring elements 3238, 3240, including the dowels 3248, may project outwardly from the medial bone-facing surface 3206 orthogonally as shown in FIGS. 10C and 10D or at an acute angle when viewed from an anterior direction (FIG. 10D) or a posterior direction (FIG. 10C). The acute angle may be on either side of the anchoring element, i.e., on the superior or inferior side. For example, the acute angle may be on the superior side of the superior anchoring element 3238, and on the inferior side of the inferior anchoring element 3240 so that the anchoring elements 3238, 3240 diverge as they extend medially, or vice versa so that the anchoring elements 3238, 3240 converge as they extend medially.

A slot 3264, or groove or channel, may be present along the dowel 3248. Anterior slots 3264 are shown on the dowels 3248 of the anchoring elements 3238, 3240, 3242. In cemented applications of the technology, the bone cement may flow along the slot 3264. The slot 3264 may terminate laterally in a planar face 3257 which may establish the plane 3251 from which the angle 3250 is measured. The planar face 3257 may be tangent to the medial bone-facing surface 3206.

The anchoring elements 3238, 3240, 3242 may include surface features to improve fixation, or pull-out strength, after implantation. The surface features may facilitate bony ingrowth or bone cement interdigitation. Surface features may be present on one or more of the anchoring elements present on a glenoid component. The surface features may project outwardly or inwardly from the fundamental surface(s) of the anchoring elements 3238, 3240, 3242. The surface features may include notches, grooves, channels, ridges, accordion texture, barbs, threads, shelves, rings, ribs, or perforations.

A particular surface feature may be oriented on an axis parallel to and offset from the corresponding axis of the fundamental surface of the corresponding anchoring element 3238 or 3240. For example, the dowel 3248 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 3238, 3240 to bend when inserted into the bone tunnel.

The anchoring elements 3238, 3240 may include at least two surface features, wherein the first surface feature is resistant to forces acting along a first direction, wherein the second surface feature is resistant to forces acting along a second direction, wherein the first and second directions are nonparallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the dowel). The first and second surface features may be intersecting planar surfaces which are side by side on a shelf of an anchoring element.

The anchoring elements 3238, 3240 may include one or more surface features that are resistant to side-to-side translation of the glenoid component 3200, i.e., translation in the superior-inferior and/or anterior-posterior directions. A translation resistant surface features may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature.

The free end of the dowel 3248 of each anchoring element 3238, 3240, 3242 includes an enlarged portion 3272 that protrudes to one side of the dowel. A shelf 3273 is formed between the enlarged portion 3272 and the normal sized dowel 3248. A bevel 3275 may be present at the free end of the enlarged portion 3272. The enlarged portion 3272 may protrude to any side of the dowel 3248. Referring to FIG. 10B, the enlarged portion 3272 of the superior anchoring element 3238 protrudes along a first direction indicated by dashed line 3274, the enlarged portion 3272 of the inferior anchoring element 3240 protrudes along a second direction indicated by dashed line 3276, and the enlarged portion 3272 of the middle anchoring element 3242 protrudes along a third direction indicated by dashed line 3278. Line 3274 extends in an anterior-superior to posterior-inferior direction. Line 3276 extends in an anterior-inferior to posterior-superior direction. Lines 3274 and 3276 form an angle 3280. Line 3278 extends in an anterior-posterior direction. Lines 3274 and 3278 form an angle 3282. Lines 3276 and 3278 form an angle 3284. Line 3278 may bisect the angle 3280 between lines 3274 and 3276. During insertion, as each dowel 3248 enters the corresponding bone hole, the enlarged portion 3272 (specifically the bevel 3275 if present) pushes against the corresponding side of the bone hole. The bone resists, forcing the free end of the dowel 3248 to deflect so that the dowel 3248 bends along its axis 3249. The illustrated arrangement of enlarged portions 3272 causes anchoring elements 3238, 3240 to bend away from each other in the first plane 2 and urges the anterior side of the anchoring elements 3238, 3240 toward the corresponding wall of the bone hole. However, the posterior side of anchoring element 3242 is urged toward the corresponding wall of the bone hole. In this arrangement, the anchoring elements 3238, 3240, 3242 tend to diverge during insertion. The anchoring element 3242 may bend in the second plane 4, and may prevent the glenoid component 3200 from rocking in the second plane 4. In other words, rocking or rotating in an anterior-posterior direction about an axis that extends substantially in a superior-inferior direction, or experiencing anterior or posterior lift-off or lever-out.

Referring to FIGS. 11A-11K, yet another glenoid component 3300 includes a body 3302 with a lateral articular surface 3304 and an opposite medial bone-facing surface 3306.

A peripheral wall 3308 extends around the body 3302 between the surfaces 3304, 3306. A lateral peripheral edge 3310 extends around the body 3302 where the lateral articular surface 3304 intersects the peripheral wall 3308. The lateral peripheral edge 3310 may be rounded or relieved by a lateral peripheral relief 3312, such as a radius, fillet, chamfer, bevel, or the like. A medial peripheral edge 3314 extends around the body 3302 where the medial bone-facing surface 3306 intersects the peripheral wall 3308. The medial peripheral edge 3314 may be rounded or relieved by a medial peripheral relief 3316, such as a radius, fillet, chamfer, bevel, or the like.

The body 3302, lateral articular surface 3304, medial bone-facing surface 3306, peripheral wall 3308, lateral peripheral edge 3310, lateral peripheral relief 3312, medial peripheral edge 3314, and/or medial peripheral relief 3316 may be divided into a superior portion 3318, an inferior portion 3320, an anterior portion 3322, and a posterior portion 3324. The body 3302, lateral articular surface 3304, and/or medial bone-facing surface 3306 may also be divided into a peripheral portion near the peripheral wall 3308 and an interior or central portion. In examples other than shoulder glenoid components, where the surgical approach trajectory may be different than the approach described herein, the appropriate medical directional terms may be readily substituted by one of skill in the art.

The lateral articular surface 3304 may be concave, as shown best in FIGS. 11D and 11E, planar, or convex in order to complement a natural or prosthetic humeral articular surface. The lateral articular surface 3304 may be spherical, elliptical, or ovoid. The lateral articular surface 3304 may have a first radius 3326 which is dimensionally different from, i.e., larger or smaller than, a second radius 3328. The first radius 3326 may be a superior-inferior radius, or S-I radius. The second radius 3328 may be an anterior-posterior radius, or A-P radius.

The inferior portion 3320 of the body 3302 may include an inferior chamfer 3330 which extends between the lateral articular surface 3304 and the peripheral wall 3308. The inferior chamfer 3330 is a sloping surface, preferably a planar surface, that lowers the profile and thickness of the inferior portion 3320 along the lateral peripheral edge 3310.

The medial bone-facing surface 3306 may be convex as shown, planar, or concave.

The glenoid component 3300 includes at least one anchoring element 3338 which protrudes outwardly from the medial bone-facing surface 3306. The example shown includes a superior anchoring element 3338, an inferior anchoring element 3340, and a middle anchoring element 3342, although any number of anchoring elements may be present. Each anchoring element may be independently positioned on the medial bone-facing surface 3306, and may be independently sized.

Each anchoring element 3338, 3340, 3342 includes a dowel 3348. Each dowel 3348 includes a central longitudinal axis 3349. The axes 3349 of the dowels 3348 may be parallel within a tolerance of ten degrees, eight degrees, six degrees, four degrees, two degrees, or one degree. Referring to FIGS. 11E-11G, the axes 3349 of the dowels 3348 of the anchoring elements 3338, 3340 lie on the first plane 2. The axis 3349 of the dowel 3348 of the anchoring element 3342 lies on the second plane 4. The first and second planes 2, 4 are represented as lines since they are viewed on edge.

In this example, each dowel 3348 projects from the medial bone-facing surface 3306 at an acute angle 3350 which is less than ninety degrees and greater than zero degrees, when viewed from a superior direction or an inferior direction. See FIGS. 11E and 11F. The angle 3350 may be referred to as a dowel angle. The angle 3350 may be measured between the central longitudinal axis 3349 of the dowel 3348 and a plane 3351. The plane 3351 may be coplanar with the medial bone-facing surface 3306, if surface 3306 is planar, or tangent to the medial bone-facing surface 3306, if surface 3306 is concave or convex. The plane 3351 may be tangent to the medial bone-facing surface 3306 at an intersection point between the central longitudinal axis 3349 of the dowel 3348 and the medial bone-facing surface 3306, or at a centroid of the medial bone-facing surface 3306. The dowel 3348 may project from the anterior portion 3322 of the body 3302, as shown for the anchoring elements 3338, 3340, or from another portion of the body 3302; the dowel 3348 of the middle anchoring element 3342 is shown projecting from the interior portion of the body 3302. In the example shown, the dowels 3348 of anchoring elements 3338, 3340 project from peripheral locations in the anterior portion 3322 and terminate in medially (centrally) located free ends. The dowel 3348 of anchoring element 3342 projects from an interior location and terminates in a posteriorly located free end. The dowel 3348 may have a round fundamental cross sectional shape, as shown, or another shape, such as a rectangle or dovetail. The dowel 3348 may include a hole 3370, which may receive a radiographic marker.

The anchoring elements 3338, 3340, including the dowels 3348, may project outwardly from the medial bone-facing surface 3306 orthogonally as shown in FIGS. 11C and 11D or at an acute angle when viewed from an anterior direction (FIG. 11D) or a posterior direction (FIG. 11C). The acute angle may be on either side of the anchoring element, i.e., on the superior or inferior side. For example, the acute angle may be on the superior side of the superior anchoring element 3338, and on the inferior side of the inferior anchoring element 3340 so that the anchoring elements 3338, 3340 diverge as they extend medially, or vice versa so that the anchoring elements 3338, 3340 converge as they extend medially.

A slot 3364, or groove or channel, may be present along the dowel 3348. Anterior slots 3364 are shown on the dowels 3348 of the anchoring elements 3338, 3340, 3342. In cemented applications of the technology, the bone cement may flow along the slot 3364. The slot 3364 may terminate laterally in a planar face 3357 which may establish the plane 3351 from which the angle 3350 is measured. The planar face 3357 may be tangent to the medial bone-facing surface 3306.

The anchoring elements 3338, 3340, 3342 may include surface features to improve fixation, or pull-out strength, after implantation. The surface features may facilitate bony ingrowth or bone cement interdigitation. Surface features may be present on one or more of the anchoring elements present on a glenoid component. The surface features may project outwardly or inwardly from the fundamental surface(s) of the anchoring elements 3338, 3340, 3342. The surface features may include notches, grooves, channels, ridges, accordion texture, barbs, threads, shelves, rings, ribs, or perforations. For example, grooves 3362 are shown on the superior and inferior sides of the dowels 3348 of the anchoring elements 3338, 3340. The illustrated grooves 3362 are oriented to resist forces acting perpendicular to the back side of the glenoid component, or the face 3357. In other words, the grooves 3362 extend parallel to the planar face 3357 when viewed from a superior or inferior direction. See FIGS. 11E and 11F.

A particular surface feature may be oriented on an axis parallel to and offset from the corresponding axis of the fundamental surface of the corresponding anchoring element 3338 or 3340. For example, the dowel 3348 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 3338, 3340 to bend when inserted into the bone tunnel.

The anchoring elements 3338, 3340 may include at least two surface features, wherein the first surface feature is resistant to forces acting along a first direction, wherein the second surface feature is resistant to forces acting along a second direction, wherein the first and second directions are nonparallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the dowel). The first and second surface features may be intersecting planar surfaces which are side by side on a shelf of an anchoring element.

The anchoring elements 3338, 3340 may include one or more surface features that are resistant to side-to-side translation of the glenoid component 3300, i.e., translation in the superior-inferior and/or anterior-posterior directions. A translation resistant surface features may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature.

The free end of the dowel 3348 of each anchoring element 3338, 3340, 3342 includes an enlarged portion 3372 that protrudes to one side of the dowel. A shelf 3373 is formed between the enlarged portion 3372 and the normal sized dowel 3348. A bevel 3375 may be present at the free end of the enlarged portion 3372. The enlarged portion 3372 may protrude to any side of the dowel 3348. Referring to FIG. 11G, the enlarged portion 3372 of the superior anchoring element 3338 protrudes along a first direction indicated by dashed line 3374, the enlarged portion 3372 of the inferior anchoring element 3340 protrudes along a second direction indicated by dashed line 3376, and the enlarged portion 3372 of the middle anchoring element 3342 protrudes along a third direction indicated by dashed line 3378. Line 3374 extends in an anterior-inferior to posterior-superior direction. Line 3376 extends in an anterior-superior to posterior-inferior direction. Lines 3374 and 3376 form an angle 3380. Line 3378 extends in an anterior-posterior direction. Lines 3374 and 3378 form an angle 3382. Lines 3376 and 3378 form an angle 3384. Line 3378 may bisect the angle 3380 between lines 3374 and 3376. During insertion, as each dowel 3348 enters the corresponding bone hole, the enlarged portion 3372 (specifically the bevel 3375 if present) pushes against the corresponding side of the bone hole. The bone resists, forcing the free end of the dowel 3348 to deflect so that the dowel 3348 bends along its axis 3349. The illustrated arrangement of enlarged portions 3372 causes anchoring elements 3338, 3340 to bend toward each other in the first plane 2 and urges the anterior side of the anchoring elements 3338, 3340, 3342 toward the corresponding wall of the bone hole. Since all of the anchoring elements 3338, 3340, 3342 are urged anteriorly in the illustrated arrangement, the entire glenoid component 3300 is urged anteriorly as well. The anchoring element 3342 may bend in the second plane 4, and may prevent the glenoid component 3300 from rocking in the second plane 4. In other words, rocking or rotating in an anterior-posterior direction about an axis that extends substantially in a superior-inferior direction, or experiencing anterior or posterior lift-off or lever-out.

Referring to FIGS. 12A-12K, yet another glenoid component 3400 includes a body 3402 with a lateral articular surface 3404 and an opposite medial bone-facing surface 3406.

A peripheral wall 3408 extends around the body 3402 between the surfaces 3404, 3406. A lateral peripheral edge 3410 extends around the body 3402 where the lateral articular surface 3404 intersects the peripheral wall 3408. The lateral peripheral edge 3410 may be rounded or relieved by a lateral peripheral relief 3412, such as a radius, fillet, chamfer, bevel, or the like. A medial peripheral edge 3414 extends around the body 3402 where the medial bone-facing surface 3406 intersects the peripheral wall 3408. The medial peripheral edge 3414 may be rounded or relieved by a medial peripheral relief 3416, such as a radius, fillet, chamfer, bevel, or the like.

The body 3402, lateral articular surface 3404, medial bone-facing surface 3406, peripheral wall 3408, lateral peripheral edge 3410, lateral peripheral relief 3412, medial peripheral edge 3414, and/or medial peripheral relief 3416 may be divided into a superior portion 3418, an inferior portion 3420, an anterior portion 3422, and a posterior portion 3424. The body 3402, lateral articular surface 3404, and/or medial bone-facing surface 3406 may also be divided into a peripheral portion near the peripheral wall 3408 and an interior or central portion. In examples other than shoulder glenoid components, where the surgical approach trajectory may be different than the approach described herein, the appropriate medical directional terms may be readily substituted by one of skill in the art.

Figure 12E:
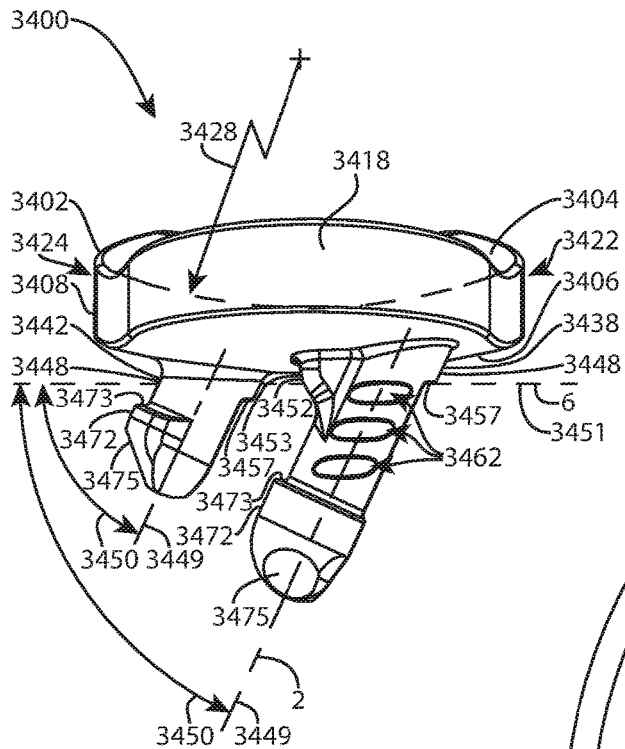
FIG. 12E is a superior view of the glenoid component of FIG. 12A.

The lateral articular surface 3404 may be concave, as shown best in FIGS. 12D and 12E, planar, or convex in order to complement a natural or prosthetic humeral articular surface. The lateral articular surface 3404 may be spherical, elliptical, or ovoid. The lateral articular surface 3404 may have a first radius 3426 which is dimensionally different from, i.e., larger or smaller than, a second radius 3428. The first radius 3426 may be a superior-inferior radius, or S-I radius. The second radius 3428 may be an anterior-posterior radius, or A-P radius.

The inferior portion 3420 of the body 3402 may include an inferior chamfer 3430 which extends between the lateral articular surface 3404 and the peripheral wall 3408. The inferior chamfer 3430 is a sloping surface, preferably a planar surface, that lowers the profile and thickness of the inferior portion 3420 along the lateral peripheral edge 3410.

The medial bone-facing surface 3406 may be convex as shown, planar, or concave.

The glenoid component 3400 includes at least one anchoring element 3438 which protrudes outwardly from the medial bone-facing surface 3406. The example shown includes a superior anchoring element 3438, an inferior anchoring element 3440, and a middle anchoring element 3442, although any number of anchoring elements may be present. Each anchoring element may be independently positioned on the medial bone-facing surface 3406, and may be independently sized.

Figure 12G:
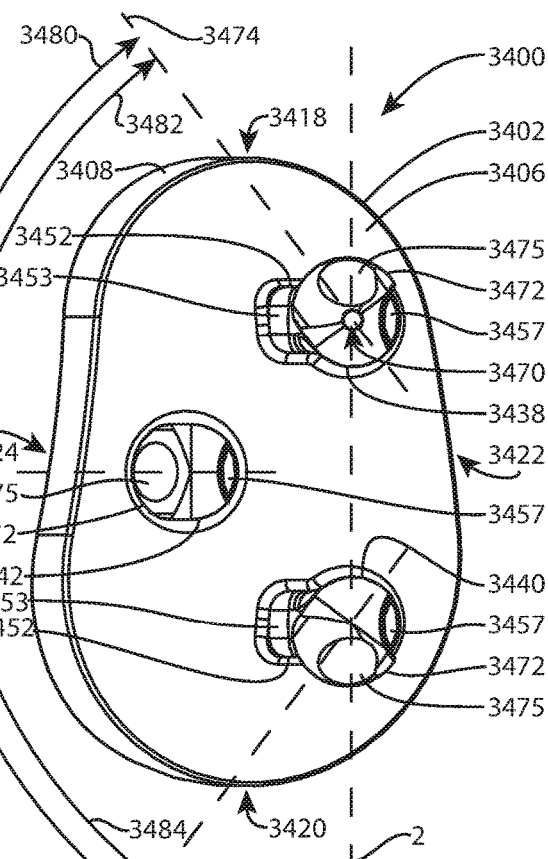
FIG. 12G is a medial-posterior view of the glenoid component of FIG. 12A.
Figure 12F:
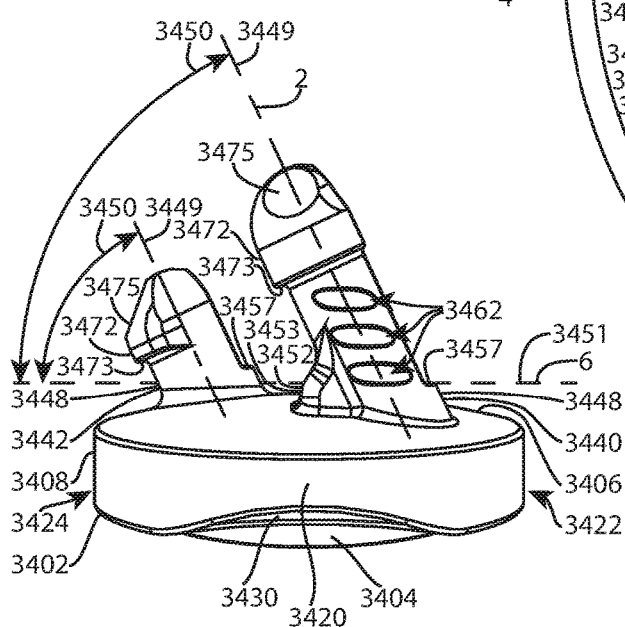
FIG. 12F is an inferior view of the glenoid component of FIG. 12A.

Each anchoring element 3438, 3440 includes a dowel 3448 and a reinforcement plate 3452, or buttress. The middle anchoring element 3442 includes a dowel 3448. Each dowel 3448 includes a central longitudinal axis 3449. The axes 3449 of the dowels 3448 may be parallel within a tolerance of ten degrees, eight degrees, six degrees, four degrees, two degrees, or one degree. Referring to FIGS. 12E-12G, the axes 3449 of the dowels 3448 of the anchoring elements 3438, 3440 lie on the first plane 2. The axis 3449 of the dowel 3448 of the anchoring element 3442 lies on the second plane 4. The first and second planes 2, 4 are represented as lines since they are viewed on edge.

In this example, each dowel 3448 projects from the medial bone-facing surface 3406 at an acute angle 3450 which is less than ninety degrees and greater than zero degrees, when viewed from a superior direction or an inferior direction. See FIGS. 12E and 12F. The angle 3450 may be referred to as a dowel angle. The angle 3450 may be measured between the central longitudinal axis 3449 of the dowel 3448 and a plane 3451. The plane 3451 may be coplanar with the medial bone-facing surface 3406, if surface 3406 is planar, or tangent to the medial bone-facing surface 3406, if surface 3406 is concave or convex. The plane 3451 may be tangent to the medial bone-facing surface 3406 at an intersection point between the central longitudinal axis 3449 of the dowel 3448 and the medial bone-facing surface 3406, or at a centroid of the medial bone-facing surface 3406. The dowel 3448 may project from the anterior portion 3422 of the body 3402, as shown for the anchoring elements 3438, 3440, or from another portion of the body 3402; the dowel 3448 of the middle anchoring element 3442 is shown projecting from the interior portion of the body 3402. In the example shown, the dowels 3448 of anchoring elements 3438, 3440 project from peripheral locations in the anterior portion 3422 and terminate in medially located free ends. The dowel 3448 of anchoring element 3442 projects from an interior location and terminates in a posteriorly located free end. The dowel 3448 may have a round fundamental cross sectional shape, as shown, or another shape, such as a rectangle or dovetail. The dowel 3448 may include a hole 3470, which may receive a radiographic marker.

The reinforcement plate 3452 projects from the medial bone-facing surface 3406 in the acute angle 3450 between the dowel 3448 and the medial bone-facing surface 3406, and coplanar with the dowel 3448. An exposed side 3453 of the reinforcement plate 3452 faces generally posteriorly in this example. One side of the reinforcement plate 3452 is formed by the medial bone-facing surface 3406, one side is formed by the dowel 3448, and one side is formed by the exposed side 3453. The plate 3452 may be narrower than the dowel 3448 as shown.

The anchoring elements 3438, 3440, including the dowels 3448, the reinforcement plates 3452, and the pedestals 3456, may project outwardly from the medial bone-facing surface 3406 orthogonally as shown in FIGS. 12C and 12D or at an acute angle when viewed from an anterior direction (FIG. 12D) or a posterior direction (FIG. 12C). The acute angle may be on either side of the anchoring element, i.e., on the superior or inferior side. For example, the acute angle may be on the superior side of the superior anchoring element 3438, and on the inferior side of the inferior anchoring element 3440 so that the anchoring elements 3438, 3440 diverge as they extend medially, or vice versa so that the anchoring elements 3438, 3440 converge as they extend medially.

A slot 3464, or groove or channel, may be present along the dowel 3448. Anterior slots 3464 are shown on the dowels 3448 of the anchoring elements 3438, 3440, 3442. In cemented applications of the technology, the bone cement may flow along the slot 3464. The slot 3464 may terminate laterally in a planar face 3457 which may establish the plane 3451 from which the angle 3450 is measured. The planar face 3457 may be tangent to the medial bone-facing surface 3406.

The anchoring elements 3438, 3440, 3442 may include surface features to improve fixation, or pull-out strength, after implantation. The surface features may facilitate bony ingrowth or bone cement interdigitation. Surface features may be present on one or more of the anchoring elements present on a glenoid component. The surface features may project outwardly or inwardly from the fundamental surface(s) of the anchoring elements 3438, 3440, 3442. The surface features may include notches, grooves, channels, ridges, accordion texture, barbs, threads, shelves, rings, ribs, or perforations. For example, grooves 3462 are shown on the superior and inferior sides of the dowels 3448 of the anchoring elements 3438, 3440. The illustrated grooves 3462 are oriented to resist forces acting perpendicular to the back side of the glenoid component, or the face 3457. In other words, the grooves 3462 extend parallel to the planar face 3457 when viewed from a superior or inferior direction. See FIGS. 12E and 12F.

A particular surface feature may be oriented on an axis parallel to and offset from the corresponding axis of the fundamental surface of the corresponding anchoring element 3438 or 3440. For example, the dowel 3448 and its associated surface feature may both be cylindrical, each of which has a central longitudinal axis, wherein the two axes are parallel to and offset from each other. This arrangement may provide a tighter fit of the surface feature in the bone tunnel, and may cause the superior anchoring elements 3438, 3440 to bend when inserted into the bone tunnel.

The anchoring elements 3438, 3440 may include at least two surface features, wherein the first surface feature is resistant to forces acting along a first direction, wherein the second surface feature is resistant to forces acting along a second direction, wherein the first and second directions are nonparallel to each other, i.e., they intersect or are skew. The first and second surface features may be on two separate anchoring elements, spaced apart on a single anchoring element, or so close together as to interact with each other on a single anchoring element. Preferably, the first and second surface features are on a single anchoring element, or on a single structure of an anchoring element (such as the dowel). The first and second surface features may be intersecting planar surfaces which are side by side on a shelf of an anchoring element.

The anchoring elements 3438, 3440 may include one or more surface features that are resistant to side-to-side translation of the glenoid component 3400, i.e., translation in the superior-inferior and/or anterior-posterior directions. A translation resistant surface features may be a portion of the anchoring element with larger width or diameter to more tightly fit the bone tunnel in which the glenoid component is inserted. An anchoring element for use with bone cement may have a unilateral translation resistant surface feature that projects to one side, or is built up on one side, and may be associated with a portion with reduced width or diameter to provide a pathway for bone cement to flow around at least the reduced portion of the anchoring element to form an effective cement mantle. The reduced portion may be beside or opposite (contralateral) to the unilateral translation resistant surface feature.

The free end of the dowel 3448 of each anchoring element 3438, 3440, 3442 includes an enlarged portion 3472 that protrudes to one side of the dowel. A shelf 3473 is formed between the enlarged portion 3472 and the normal sized dowel 3448. A bevel 3475 may be present at the free end of the enlarged portion 3472. The enlarged portion 3472 may protrude to any side of the dowel 3448. Referring to FIG. 12G, the enlarged portion 3472 of the superior anchoring element 3438 protrudes along a first direction indicated by dashed line 3474, the enlarged portion 3472 of the inferior anchoring element 3440 protrudes along a second direction indicated by dashed line 3476, and the enlarged portion 3472 of the middle anchoring element 3442 protrudes along a third direction indicated by dashed line 3478. Line 3474 extends in an anterior-inferior to posterior-superior direction. Line 3476 extends in an anterior-superior to posterior-inferior direction. Lines 3474 and 3476 form an angle 3480. Line 3478 extends in an anterior-posterior direction. Lines 3474 and 3478 form an angle 3482. Lines 3476 and 3478 form an angle 3484. Line 3478 may bisect the angle 3480 between lines 3474 and 3476. During insertion, as each dowel 3448 enters the corresponding bone hole, the enlarged portion 3472 (specifically the bevel 3475 if present) pushes against the corresponding side of the bone hole. The bone resists, forcing the free end of the dowel 3448 to deflect so that the dowel 3448 bends along its axis 3449. The illustrated arrangement of enlarged portions 3472 causes anchoring elements 3438, 3440 to bend toward each other in the first plane 2 and urges the anterior side of the anchoring elements 3438, 3440, 3442 toward the corresponding wall of the bone hole. Since all of the anchoring elements 3438, 3440, 3442 are urged anteriorly in the illustrated arrangement, the entire glenoid component 3400 is urged anteriorly as well. The anchoring element 3442 may bend in the second plane 4, and may prevent the glenoid component 3400 from rocking in the second plane 4. In other words, rocking or rotating in an anterior-posterior direction about an axis that extends substantially in a superior-inferior direction, or experiencing anterior or posterior lift-off or lever-out.

Referring to FIGS. 13A-13J, yet more glenoid components 3500, 3600, 3700, 3800, 3900 are shown. FIGS. 13A-13H show the glenoid components 3500, 3600, 3700, 3800 in cross section, taken across the anterior-posterior width of the glenoid component. FIGS. 13I and 13J show lateral views of the glenoid components 3600, 3900.

Referring to FIGS. 13A and 13C, glenoid component 3500 includes a body 3502 with a lateral articular surface 3504 and an opposite medial bone-facing surface 3506.

A peripheral wall 3508 extends around the body 3502 between the surfaces 3504, 3506. A lateral peripheral edge 3510 extends around the body 3502 where the lateral articular surface 3504 intersects the peripheral wall 3508. The lateral peripheral edge 3510 may be rounded or relieved by a lateral peripheral relief, such as a radius, fillet, chamfer, bevel, or the like. A medial peripheral edge 3514 extends around the body 3502 where the medial bone-facing surface 3506 intersects the peripheral wall 3508. The medial peripheral edge 3514 may be rounded or relieved by a medial peripheral relief, such as a radius, fillet, chamfer, bevel, or the like.

The body 3502, lateral articular surface 3504, medial bone-facing surface 3506, peripheral wall 3508, lateral peripheral edge 3510, lateral peripheral relief, if present, medial peripheral edge 3514, and/or medial peripheral relief, if present, may be divided into a superior portion, an inferior portion, an anterior portion 3522, and a posterior portion 3524. The body 3502, lateral articular surface 3504, and/or medial bone-facing surface 3506 may also be divided into a peripheral portion near the peripheral wall 3508 and an interior or central portion. In examples other than shoulder glenoid components, where the surgical approach trajectory may be different than the approach described herein, the appropriate medical directional terms may be readily substituted by one of skill in the art.

The lateral articular surface 3504 may be concave as shown, planar, or convex in order to complement a natural or prosthetic humeral articular surface. The lateral articular surface 3504 may be spherical. The lateral articular surface 3504 may be elliptical or ovoid. The lateral articular surface 3504 may have a first radius which is dimensionally different from, i.e., larger or smaller than, a second radius. The first radius may be a superior-inferior radius, or S-I radius. The second radius may be an anterior-posterior radius, or A-P radius.

The medial bone-facing surface 3506 may be planar as shown, convex, or concave.

FIG. 13C illustrates an optional anchoring element 3538 protruding from the medial bone-facing surface. The anchoring element 3538 is omitted from FIG. 13A for clarity. The anchoring element 3538 may incorporate characteristics of the anchoring elements disclosed herein, and may for example be identical to any of the anchoring elements disclosed herein, including groups of multiple anchoring elements.

The glenoid component 3500 illustrates a peripheral wall 3508 that is perpendicular to the medial bone-facing surface 3506. In other words, the peripheral wall 3508 extends parallel to a polar axis of the glenoid component 3500, which by design is the same as the polar axis of the glenoid socket into which the glenoid component will be implanted. In this arrangement, when the glenoid component 3500 is viewed from a lateral or medial direction, the lateral peripheral edge 3510 and the medial peripheral edge 3514 are the same size and shape and are superimposed over each other. While glenoid components 800, 1000, 1100, 2500, 2700, 2800, 2900, 3000, 3100, 3200, 3300, 3400 are shown with convex rather than planar bone-facing sides, they all illustrate peripheral walls and lateral and medial peripheral edges according to the same principle. The peripheral walls of these glenoid components may extend perpendicular to a plane that is tangent to the bone-facing side at the intersection of the bone-facing side and the glenoid component polar axis. When the glenoid components 800, 1000, 1100, 2500, 2700, 2800, 2900, 3000, 3100, 3200, 3300, 3400 are viewed from a lateral or medial direction, the respective lateral and medial peripheral edges are the same size and shape and are superimposed on each other.

Referring to FIG. 13C, the dashed line 3580 represents edge loading applied to the posterior portion 3524 of the lateral peripheral edge 3510. The edge load may be normal to the lateral articular surface 3504 at that location. The posterior portion 3524 of the medial peripheral edge 3514 acts as a fulcrum about which the glenoid component 3500 tends to rotate (in a counterclockwise direction in this example) according to the principles of a first class lever. The dashed line 3582 is perpendicular to the line 3580 and extends antero-medially to the medial bone-facing surface 3506. The dashed line 3584 extends from the intersection of the line 3582 and the medial bone-facing surface 3506, perpendicular to the line 3582 and parallel to the line 3580. The line 3584 may represent a fixation force that counteracts the edge loading along line 3580 to keep the glenoid component 3500 secured in place in a glenoid socket. Alternatively, the line 3584 may represent an anterior tensile lift-off force. The edge loading along line 3580 and the lift-off force along line 3584 may form a force couple about the posterior portion 3524 of the medial peripheral edge 3514.

Stability of the glenoid component 3500 may be enhanced by positioning an anchoring element (or a portion thereof) anterior to the intersection of the lines 3582, 3584 and the medial bone-facing surface 3506, positioning the posterior portion 3524 of the medial peripheral edge 3514 posterior to the line 3580, or both.

Referring to FIGS. 13B, 13E, 13G, and 13I, glenoid component 3600 illustrates a modification of glenoid component 3500 in which the medial bone-facing surface 3606 has been enlarged relative to the lateral articular surface 3604 to move the posterior portion 3624 of the medial peripheral edge 3614 posteriorly and to move the anterior portion 3622 of the medial peripheral edge 3614 anteriorly. The peripheral wall 3608 in this example tapers inwardly from the medial peripheral edge 3614 to the lateral peripheral edge 3610. These design changes may be made only to the anterior and posterior portions 3622, 3624, or they may be made all around the periphery of the glenoid component 3600 including the superior and inferior portions (FIG. 13I). The medial bone-facing surface 3606 and the medial peripheral edge 3614 may be enlarged by a constant increment all around the periphery of the glenoid component 3600 (FIG. 13I), or the increment may be variable around the periphery (glenoid component 3900, FIG. 13J). Any of the glenoid components disclosed herein may be modified in this manner.

Referring to FIG. 13E, the dashed line 3680 represents edge loading applied to the posterior portion 3624 of the lateral peripheral edge 3610. The dashed line 3682 is perpendicular to the line 3680 and extends antero-medially to the medial bone-facing surface 3606. The posterior portion 3624 of the medial peripheral edge 3614 no longer acts as a fulcrum according to the principles of a first class lever, because the posterior portion 3624 of the medial peripheral edge 3614 is posterior to the line 3680, while the edge load along line 3680 and corresponding fixation force or lift off force parallel to line 3680 at the anterior end of line 3682 are both anterior to the posterior portion 3624 of the medial peripheral edge 3614.

Referring to FIG. 13G, the dashed line 3682 forms an angle 3686 with the medial bone-facing surface 3606. The posterior peripheral wall 3608 forms an angle 3688 with the dashed line 3690. The dashed line 3690 is perpendicular to the medial bone-facing surface 3606 and may represent the unmodified peripheral wall 3508 of glenoid component 3500 or the peripheral wall of any of the glenoid components 800, 1000, 1100, 2500, 2700, 2800, 2900, 3000, 3100, 3200, 3300, 3400 disclosed herein. Stability of the glenoid component 3600 may be enhanced in designs where the angle 3688 is greater than the angle 3686.

Referring to FIG. 13I, a lateral view of the glenoid component 3600 illustrates a design in which the medial bone-facing surface 3606 has been enlarged relative to the lateral articular surface 3604 all around the periphery of the glenoid component 3600 including the superior and inferior portions 3618, 3620. The medial bone-facing surface 3606 has a larger area than the lateral articular surface 3604. In the lateral view, the medial bone-facing surface 3606 extends past the lateral articular surface 3604 in the anterior, posterior, superior, and inferior directions, and in between (i.e., antero-superior, antero-inferior, postero-superior, and postero-inferior). The medial peripheral edge 3614 has a larger perimeter than the lateral peripheral edge 3610. The lateral peripheral edge 3610 is circumscribed by the medial peripheral edge 3614.

Referring to FIG. 13J, a lateral view of glenoid component 3900 illustrates a design in which the medial bone-facing surface has been enlarged relative to the lateral articular surface 3904 by a variable increment all around the periphery of the glenoid component 3900 including the superior and inferior portions 3918, 3920. The increment is larger along the anterior and posterior portions 3922, 3924 and smaller along the superior and inferior portions 3918, 3920. The increment can vary in the opposite way, so that the increment is larger along the superior and inferior portions 3918, 3920 and smaller along the anterior and posterior portions 3922, 3924. The increment can vary in other ways as well. For example, the increment may be zero at selected locations around the periphery of the glenoid component 3900. FIG. 13J shows an example in which the medial bone-facing surface 3906 has a larger area than the lateral articular surface 3904. In the lateral view, the medial bone-facing surface 3906 extends past the lateral articular surface 3904 in the anterior, posterior, superior, and inferior directions (more so in the anterior and posterior directions), and in between (i.e., antero-superior, antero-inferior, postero-superior, and postero-inferior). The medial peripheral edge 3914 has a larger perimeter than the lateral peripheral edge 3910. The lateral peripheral edge 3910 is circumscribed by the medial peripheral edge 3914.

Referring to FIG. 13D, glenoid component 3700 illustrates a modification of glenoid component 3500 in which the medial bone-facing surface 3706 has been enlarged relative to the lateral articular surface 3704 to move the posterior portion 3724 of the medial peripheral edge 3714 posteriorly and to move the anterior portion 3722 of the medial peripheral edge 3714 anteriorly. The peripheral wall 3708 in this example steps inwardly from the medial peripheral edge 3714 to the lateral peripheral edge 3710. The glenoid component 3700 may be described as having a flange 3715 along the anterior and posterior portions 3722, 3724 at the medial peripheral edge 3714. These design changes may be made only to the anterior and posterior portions 3722, 3724, or they may be made all around the periphery of the glenoid component 3700 including the superior and inferior portions, in which case the flange 3715 would extend all around the periphery of the glenoid component 3700. The medial bone-facing surface 3706 and the medial peripheral edge 3714 may be enlarged by a constant increment all around the periphery of the glenoid component 3700, or the increment may be variable around the periphery. Any of the glenoid components disclosed herein may be modified in this manner.

Referring to FIGS. 13F and 13H, glenoid component 3800 illustrates the principles established in the preceding discussion of glenoid components 3500, 3600, 700, 3900 in a glenoid component with a convex medial bone-facing surface 3806 instead of a planar medial bone-facing surface. Glenoid component 3800 may represent a modification of any one of glenoid components 800, 1000, 1100, 2500, 2700, 2800, 2900, 3000, 3100, 3200, 3300, 3400 according to these principles. The medial bone-facing surface 3806 has been enlarged relative to the lateral articular surface 3804 to move the posterior portion 3824 of the medial peripheral edge 3814 posteriorly and to move the anterior portion 3822 of the medial peripheral edge 3814 anteriorly. The peripheral wall 3808 in this example tapers inwardly from the medial peripheral edge 3814 to the lateral peripheral edge 3810. These design changes may be made only to the anterior and posterior portions 3822, 3824, or they may be made all around the periphery of the glenoid component 3800 including the superior and inferior portions. The medial bone-facing surface 3806 and the medial peripheral edge 3814 may be enlarged by a constant increment all around the periphery of the glenoid component 3800, or the increment may be variable around the periphery.

FIG. 13F illustrates an optional anchoring element 3838 protruding from the medial bone-facing surface 3806. The anchoring element 3838 is omitted from FIG. 13H for clarity. The anchoring element 3838 may incorporate characteristics of the anchoring elements disclosed herein, and may for example be identical to any of the anchoring elements disclosed herein, including groups of multiple anchoring elements.

Referring to FIG. 13F, the dashed line 3880 represents edge loading applied to the posterior portion 3824 of the lateral peripheral edge 3810. The edge load may be normal to the lateral articular surface 3804 at that location. The dashed line 3882 is perpendicular to the line 3880 and extends antero-medially to the medial bone-facing surface 3806. In this example, the line 3882 intersects the medial bone-facing surface 3806 at the anterior aspect of the anchoring element 3838. A fixation force may extend from the intersection of the line 3882 and the medial bone-facing surface 3806, parallel to the line 3880. The fixation force may counteracts the edge loading along line 3880 to keep the glenoid component 3800 secured in place in a glenoid socket. Alternatively, an anterior tensile lift-off force may act at the same location instead of the fixation force. The posterior portion 3824 of the medial peripheral edge 3814 is posterior to the line 3880 and therefore does not act as a fulcrum according to the principles of a first class lever.

The dashed line 3880' also represents edge loading applied to the posterior portion 3824 of the lateral peripheral edge 3810. The dashed line 3882' is perpendicular to the line 3880 and extends antero-medially to the medial bone-facing surface 3806. In this example, the line 3882' intersects the medial bone-facing surface 3806 at the anterior portion 3822 of the medial peripheral edge 3814. A fixation force may extend from the intersection of the line 3882' and the medial bone-facing surface 3806, parallel to the line 3880'. The fixation force may counteracts the edge loading along line 3880' to keep the glenoid component 3800 secured in place in a glenoid socket. Alternatively, an anterior tensile lift-off force may act at the same location instead of the fixation force. The posterior portion 3824 of the medial peripheral edge 3814 is posterior to the line 3880' and therefore does not act as a fulcrum according to the principles of a first class lever.

Referring to FIG. 13H, the dashed line 3882' forms an angle 3886 with the medial bone-facing surface 3806. The posterior peripheral wall 3808 forms an angle 3888 with the dashed line 3890. The dashed line 3890 may be normal to the lateral articular surface 3804 at the posterior portion 3824 of the lateral peripheral edge 3810. Stability of the glenoid component 3800 may be enhanced in designs where the angle 3888 is greater than the angle 3886.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. An arthroplasty system comprising:
a first arthroplasty prosthesis comprising a body and an anchoring element protruding from the body;
wherein the body comprises an articular surface and a bone-facing surface opposite the articular surface;
wherein the anchoring element comprises a dowel having an enlarged tip portion that protrudes unilaterally from one side of the dowel along a first direction;
wherein the dowel protrudes from the bone-facing surface at an acute first angle and comprises a central longitudinal axis.

2. The system of claim 1, wherein the dowel comprises a first surface feature and a second surface feature, wherein the first surface feature is resistant to forces acting along a first trajectory, the second surface feature is resistant to forces acting along a second trajectory, and the first and second trajectories intersect or are skew, and wherein the first trajectory is perpendicular to the bone-facing surface and the second trajectory is parallel to the central longitudinal axis of the dowel.

3. The system of claim 2, wherein the first surface feature is a ridge extending across the dowel parallel to the bone-facing surface, wherein the second surface feature is a protruding planar surface extending across the dowel perpendicular to the central longitudinal axis of the dowel.

4. The system of claim 1, wherein the enlarged tip portion is enlarged relative to a remainder of the dowel between the enlarged tip portion and the bone-facing surface.

5. The system of claim 4, wherein the enlarged tip portion causes the anchoring element to bend as the first arthroplasty prosthesis is inserted into engagement with a bone.

6. The system of claim 5, wherein the anchoring element is a first anchoring element, wherein the first arthroplasty prosthesis comprises a second anchoring element, wherein the enlarged tip portion causes the first anchoring element to bend toward the second anchoring element as the first arthroplasty prosthesis is inserted into engagement with a bone.

7. The system of claim 1, wherein:
the anchoring element comprises a first anchoring element comprising a first dowel having a first enlarged tip portion that protrudes unilaterally from one side of the first dowel along the first direction; and
the first arthroplasty prosthesis further comprises a second anchoring element comprising a second dowel having a second enlarged tip portion that protrudes unilaterally from one side of the second dowel along a second direction;
wherein, an angle formed between the first direction of the first enlarged tip portion and the second direction of the second enlarged tip portion is obtuse.

8. An arthroplasty system comprising:
a first arthroplasty prosthesis comprising a body and an anchoring element protruding from the body;
wherein the body comprises an articular surface and a bone-facing surface opposite the articular surface;
wherein the anchoring element comprises a dowel that protrudes from the bone-facing surface along a first central longitudinal axis, and wherein the dowel comprises an enlarged tip portion, the enlarged tip portion comprising a cylindrical shape having a second central longitudinal axis that is offset from the first central longitudinal axis of the dowel.

9. The system of claim 8, wherein the dowel comprises a first surface feature and a second surface feature, the first surface feature is resistant to forces acting along a first trajectory that is perpendicular to the bone-facing surface, the second surface feature is resistant to forces acting along a second trajectory that is at an acute angle to the bone-facing surface and parallel to the first central longitudinal axis of the dowel, and the first and second trajectories intersect or are skew.

10. The system of claim 9, wherein the first surface feature is a ridge extending across the dowel parallel to the bone-facing surface, wherein the second surface feature is a protruding planar surface extending across the dowel perpendicular to the first central longitudinal axis of the dowel.

11. The system of claim 8, wherein the enlarged tip portion is enlarged relative to a remainder of the dowel between the enlarged tip portion and the bone-facing surface.

12. The system of claim 11, wherein the enlarged tip portion causes the anchoring element to bend as the first arthroplasty prosthesis is inserted into engagement with a bone.

13. The system of claim 12, wherein the anchoring element is a first anchoring element, wherein the first arthroplasty prosthesis comprises a second anchoring element, wherein the enlarged tip portion causes the first anchoring element to bend toward the second anchoring element as the first arthroplasty prosthesis is inserted into engagement with the bone.

14. The system of claim 8, wherein:
the anchoring element comprises a first anchoring element comprising a first dowel having a first enlarged tip portion that protrudes unilaterally from one side of the first dowel along a first direction; and
the first arthroplasty prosthesis further comprises a second anchoring element comprising a second dowel having a second enlarged tip portion that protrudes unilaterally from one side of the second dowel along a second direction;
wherein, an angle formed between the first direction of the first enlarged tip portion and the second direction of the second enlarged tip portion is obtuse.

15. An arthroplasty system comprising:
a first arthroplasty prosthesis comprising a body and a first anchoring element, a second anchoring element, and a third anchoring element protruding from the body;
wherein the body comprises an articular surface and a bone-facing surface opposite the articular surface;
wherein:
the first anchoring element comprises a first dowel that protrudes from the bone-facing surface and comprises a first central longitudinal axis and a first enlarged tip portion, wherein the first enlarged tip portion protrudes asymmetrically from the first dowel along a first direction with respect to the first central longitudinal axis of the first dowel;
the second anchoring element comprises a second dowel that protrudes from the bone-facing surface and comprises a second central longitudinal axis and a second enlarged tip portion, wherein the second enlarged tip portion protrudes asymmetrically from the second dowel along a second direction with respect to the second central longitudinal axis of the second dowel;
the third anchoring element comprises a third dowel that protrudes from the bone-facing surface and comprises a third central longitudinal axis and a third enlarged tip portion, wherein the third enlarged tip portion protrudes asymmetrically from the third dowel along a third direction with respect to the third central longitudinal axis of the third dowel; and
wherein each of the first direction, the second direction, and the third direction are different from each other.

16. The system of claim 15, wherein:
the first dowel comprises a first surface feature and a second surface feature, the first surface feature is resistant to forces acting along a first trajectory that is perpendicular to the bone-facing surface, the second surface feature is resistant to forces acting along a second trajectory that is parallel to the first central longitudinal axis of the first dowel, and the first and second trajectories intersect or are skew;
the second dowel comprises a third surface feature and a fourth surface feature, the third surface feature is resistant to forces acting along a third trajectory that is perpendicular to the bone-facing surface, the fourth surface feature is resistant to forces acting along a fourth trajectory that is parallel to the second central longitudinal axis of the second dowel, and the third and fourth trajectories intersect or are skew; and
the third dowel comprises a fifth surface feature and a sixth surface feature, the fifth surface feature is resistant to forces acting along a fifth trajectory that is perpendicular to the bone-facing surface, the sixth surface feature is resistant to forces acting along a sixth trajectory that is parallel to the third central longitudinal axis of the third dowel, and the fifth and sixth trajectories intersect or are skew.

17. The system of claim 16, wherein:
the first surface feature is a first ridge extending across the first dowel parallel to the bone-facing surface, wherein the second surface feature is a first protruding planar surface extending across the first dowel perpendicular to the first central longitudinal axis of the first dowel;
the third surface feature is a second ridge extending across the second dowel parallel to the bone-facing surface, wherein the fourth surface feature is a second protruding planar surface extending across the second dowel perpendicular to the second central longitudinal axis of the second dowel; and
the fifth surface feature is a third ridge extending across the third dowel parallel to the bone-facing surface, wherein the sixth surface feature is a third protruding planar surface extending across the third dowel perpendicular to the third central longitudinal axis of the third dowel.

18. The system of claim 15, wherein:
the first enlarged tip portion is enlarged relative to a remainder of the first dowel between the first enlarged tip portion and the bone-facing surface;
the second enlarged tip portion is enlarged relative to a remainder of the second dowel between the second enlarged tip portion and the bone-facing surface; and
the third enlarged tip portion is enlarged relative to a remainder of the third dowel between the third enlarged tip portion and the bone-facing surface.

19. The system of claim 18, wherein:
the first enlarged tip portion causes the first anchoring element to bend as the first arthroplasty prosthesis is inserted into engagement with a bone;
the second enlarged tip portion causes the second anchoring element to bend as the first arthroplasty prosthesis is inserted into engagement with the bone; and
the third enlarged tip portion causes the third anchoring element to bend as the first arthroplasty prosthesis is inserted into engagement with the bone.

20. The system of claim 19, wherein the first enlarged tip portion causes the first anchoring element to bend toward the second anchoring element as the first arthroplasty prosthesis is inserted into engagement with the bone.

21. An arthroplasty system comprising:
a first arthroplasty prosthesis comprising a body and first and second anchoring elements protruding from the body;
wherein the body comprises an articular surface and a bone-facing surface opposite the articular surface;
wherein the first anchoring element comprises a first dowel that protrudes from the bone-facing surface along a first central longitudinal axis, wherein the first dowel comprises a first enlarged tip portion that protrudes unilaterally from one side of the first dowel along a first direction, wherein the first enlarged tip portion has a second central longitudinal axis that is offset from the first central longitudinal axis of the first dowel;
wherein the second anchoring element comprises a second dowel having a second enlarged tip portion that protrudes unilaterally from one side of the second dowel along a second direction;

wherein an angle formed between the first direction of the first enlarged tip portion and the second direction of the second enlarged tip portion is obtuse.

22. The system of claim 21, wherein the first dowel comprises first and second surface features, wherein the first surface feature is a ridge extending across the first dowel parallel to the bone-facing surface, wherein the second surface feature is a protruding planar surface extending across the first dowel perpendicular to the first central longitudinal axis of the first dowel.

23. The system of claim 21, wherein the first enlarged tip portion is enlarged relative to a remainder of the first dowel between the first enlarged tip portion and the bone-facing surface.

24. The system of claim 23, wherein the first enlarged tip portion causes the first anchoring element to bend as the first arthroplasty prosthesis is inserted into engagement with a bone.

25. The system of claim 24, wherein the first enlarged tip portion causes the first anchoring element to bend toward the second anchoring element as the first arthroplasty prosthesis is inserted into engagement with the bone.

\* \* \* \* \*